United States Patent
Falcone et al.

(10) Patent No.: US 9,480,541 B2
(45) Date of Patent: Nov. 1, 2016

(54) SELF-LIGATING ORTHODONTIC BRACKETS

(71) Applicants: Matthew James Falcone, Parlin, NJ (US); Neil Verma, Long Island City, NY (US); Sivaramakrishnan Krishnamoorthy, Albertson, NY (US); Tieming Ruan, Setauket, NY (US); Calvin Ng, Hollis, NY (US); David A. Zdurne, Lancaster, PA (US)

(72) Inventors: Matthew James Falcone, Parlin, NJ (US); Neil Verma, Long Island City, NY (US); Sivaramakrishnan Krishnamoorthy, Albertson, NY (US); Tieming Ruan, Setauket, NY (US); Calvin Ng, Hollis, NY (US); David A. Zdurne, Lancaster, PA (US)

(73) Assignee: DENTSPLY International Inc., York, PA (US)

( * ) Notice: Subject to any disclaimer, the term of this patent is extended or adjusted under 35 U.S.C. 154(b) by 9 days.

(21) Appl. No.: 14/050,330

(22) Filed: Oct. 9, 2013

(65) Prior Publication Data

US 2014/0212828 A1    Jul. 31, 2014

Related U.S. Application Data

(60) Provisional application No. 61/711,381, filed on Oct. 9, 2012, provisional application No. 61/768,317, filed on Feb. 22, 2013.

(51) Int. Cl.
*A61C 7/28* (2006.01)
*A61C 7/30* (2006.01)
*A61C 7/14* (2006.01)
*A61C 7/20* (2006.01)
*A61C 7/12* (2006.01)

(52) U.S. Cl.
CPC ............... *A61C 7/30* (2013.01); *A61C 7/125* (2013.01); *A61C 7/14* (2013.01); *A61C 7/20* (2013.01); *A61C 7/285* (2013.01); *A61C 7/287* (2013.01)

(58) Field of Classification Search
CPC .................................................. A61C 7/287
See application file for complete search history.

(56) References Cited

U.S. PATENT DOCUMENTS

| 4,149,314 A |   | 4/1979 | Nonnenmann |
|---|---|---|---|
| 4,209,906 A |   | 7/1980 | Fujita |
| 4,492,573 A | * | 1/1985 | Hanson ............... A61C 7/287 433/11 |
| 5,267,854 A |   | 12/1993 | Schmitt |

(Continued)

FOREIGN PATENT DOCUMENTS

| CN | 102462555 A | 5/2012 |
|---|---|---|
| EP | 1287789 A2 | 5/2003 |

(Continued)

OTHER PUBLICATIONS

PCT/US2013/064184 International Search Report.
(Continued)

*Primary Examiner* — Ralph Lewis
(74) *Attorney, Agent, or Firm* — David A. Zdurne; Douglas J. Hurq; Leana Levin

(57) ABSTRACT

The present invention employs a self-ligating orthodontic bracket comprising a body having a pair of laterally spaced gingival tie wings and a pair of laterally spaced occlusal tie wings, the gingival and occlusal tie wings projecting from a labial surface of the body; an arch wire slot extending mesially-distally across the body and between the gingival and occlusal tie wings to accommodate an arch wire; a free-sliding, controlled-locking, or pivoting clip wherein the clip allows placement and removal of the arch wire when in the open position and prevents the displacement of the arch wire from the bracket member when in the closed position.

12 Claims, 30 Drawing Sheets

(56) References Cited

U.S. PATENT DOCUMENTS

| | | | |
|---|---|---|---|
| 5,269,681 A | 12/1993 | Degnam | |
| 5,630,715 A * | 5/1997 | Voudouris | A61C 7/287 433/13 |
| 5,906,486 A * | 5/1999 | Hanson | A61C 7/287 433/10 |
| 5,908,293 A | 6/1999 | Voudouris | |
| 6,071,119 A * | 6/2000 | Christoff | A61C 7/287 433/13 |
| 6,168,428 B1 * | 1/2001 | Voudouris | A61C 7/285 433/11 |
| 6,368,105 B1 * | 4/2002 | Voudouris | A61C 7/282 433/11 |
| 6,843,651 B2 * | 1/2005 | Orikasa | A61C 7/287 433/13 |
| 7,442,039 B2 * | 10/2008 | Opin | A61C 7/02 433/10 |
| 7,695,277 B1 | 4/2010 | Stevens | |
| 7,717,706 B2 * | 5/2010 | Forster | A61C 7/287 433/11 |
| 2004/0157186 A1 | 8/2004 | Abels et al. | |
| 2006/0228662 A1 * | 10/2006 | Lokar | A61C 7/287 433/8 |
| 2008/0241782 A1 | 10/2008 | Abels et al. | |
| 2012/0052459 A1 | 3/2012 | Bingmin et al. | |
| 2012/0135364 A1 * | 5/2012 | Tuneberg | A61C 7/287 433/9 |

FOREIGN PATENT DOCUMENTS

| | | |
|---|---|---|
| EP | 181639 A1 | 2/2007 |
| EP | 1810640 A1 | 7/2007 |
| EP | 2189077 A1 | 5/2010 |
| EP | 2425798 A2 | 7/2012 |
| WO | 2010000883 A1 | 7/2010 |
| WO | 2012036096 A1 | 3/2012 |
| WO | 2012056408 A1 | 5/2012 |

OTHER PUBLICATIONS

PCT/US2013/064184 PCT Written Opinion.

* cited by examiner

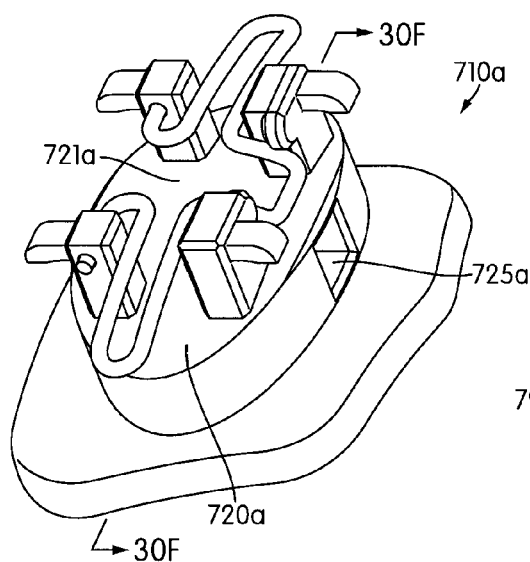
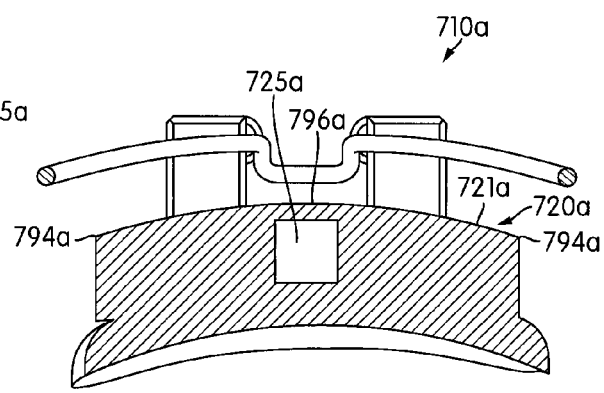
FIG. 30E    FIG. 30F
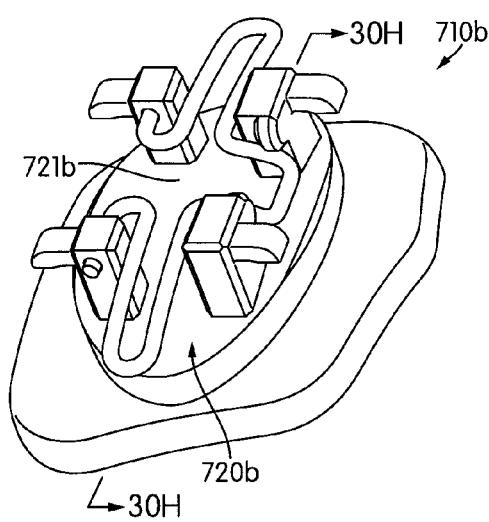
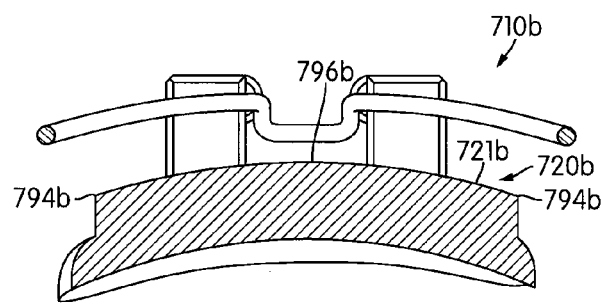
FIG. 30G    FIG. 30H

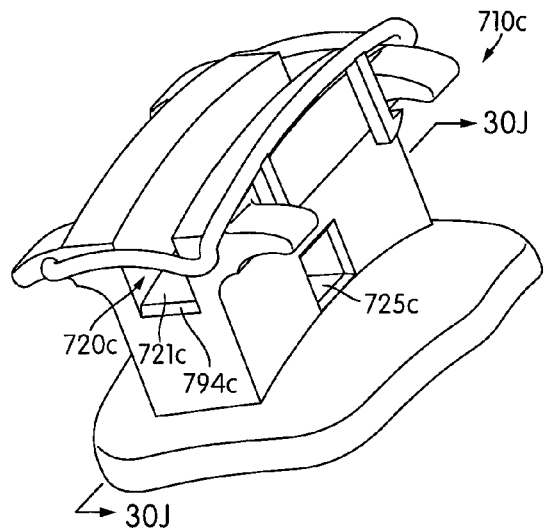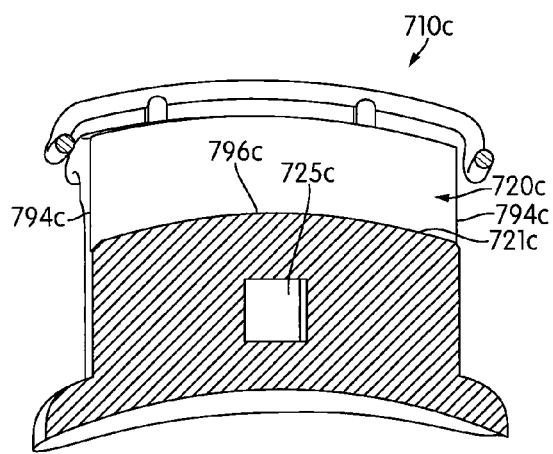
FIG. 30I  FIG. 30J
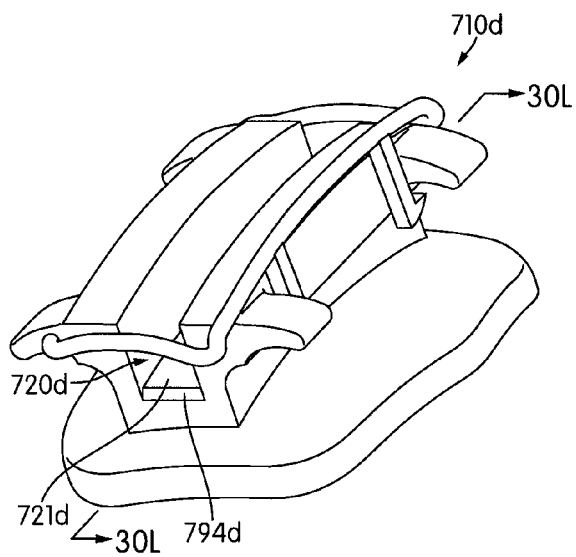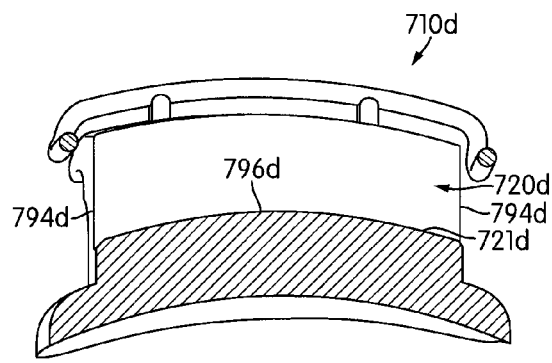
FIG. 30K  FIG. 30L

SELF-LIGATING ORTHODONTIC BRACKETS

RELATED APPLICATIONS

This patent application claims the benefit of and priority to U.S. Provisional Patent Application Ser. No. 61/711,381, filed on Oct. 9, 2012 and U.S. Provisional Patent Application Ser. No. 61/768,317, filed on Feb. 22, 2013, which are herein incorporated by reference for all purposes.

FIELD OF INVENTION

The present invention is directed to the field of orthodontics, and specifically to the field of orthodontic bracket assemblies.

SUMMARY OF THE INVENTION

The present invention provides improved self-ligating orthodontic brackets. In one aspect, the present invention provides a self-ligating orthodontic bracket comprising: a body having a pair of laterally spaced gingival tie wings and a pair of laterally spaced occlusal tie wings, the gingival and occlusal tie wings projecting from a labial surface of the body; an archwire slot extending mesially-distally across the body and between the gingival and occlusal tie wings to accommodate an arch wire; a free-sliding, controlled-locking or pivoting clip wherein the clip allows placement and removal of the arch wire when in the open position and prevents the displacement of the arch wire from the bracket member when in the closed position.

BRIEF DESCRIPTION OF THE DRAWINGS

FIG. 27D is a side view of the embodiment shown in FIG. 27A in a first closed position.

FIG. 27E is a side view of the embodiment shown in FIG. 27A in a second closed position.

FIG. 27F is a side view of the embodiment shown in FIG. 27A in an open position.

FIG. 27G is a rear perspective view of the locking clip from the embodiment shown in FIG. 27A.

FIG. 28A is a top perspective view of a twenty-eighth embodiment of the present invention in a closed position.

FIG. 28B is a cross-section view of the embodiment shown in FIG. 28A.

FIG. 28C is another top perspective view of the embodiment shown in FIG. 28A in an open position.

FIG. 28D is a cross-section view of the embodiment shown in FIG. 28A.

FIG. 28E is a perspective view of another embodiment of the present invention in a closed position, which is a variation of the embodiment shown in FIG. 28A.

FIG. 28F is a perspective view of another embodiment of the present invention in a closed position.

FIG. 28G is another perspective view of the embodiment shown in FIG. 28F in an open position.

FIG. 28H is a perspective view of another embodiment of the present invention in an open position.

Figure 28A:
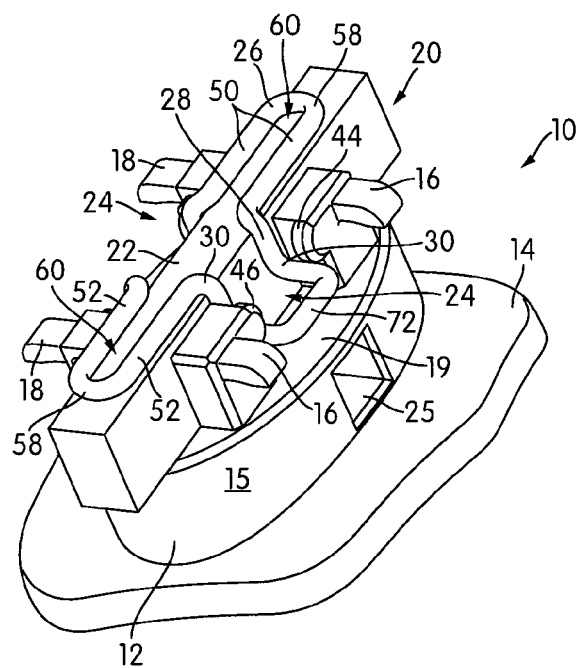
Figure 28B:
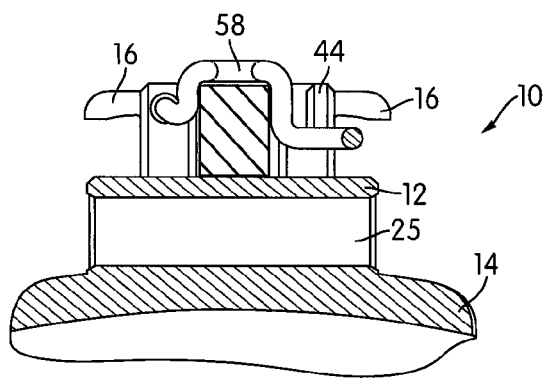
Figure 28C:
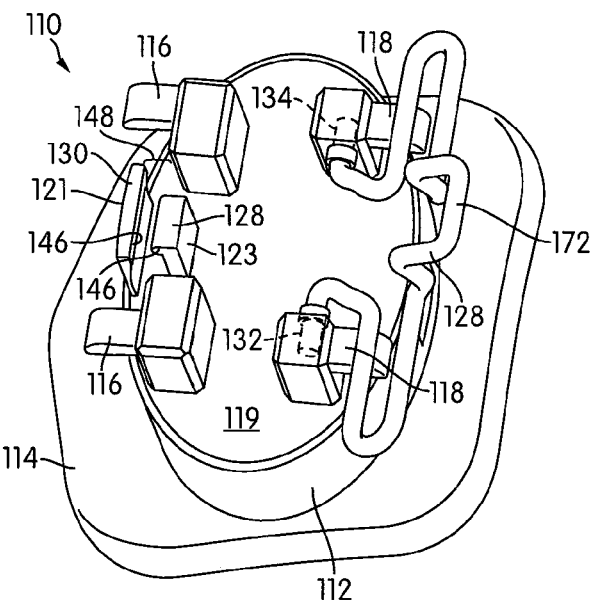
Figure 28D:
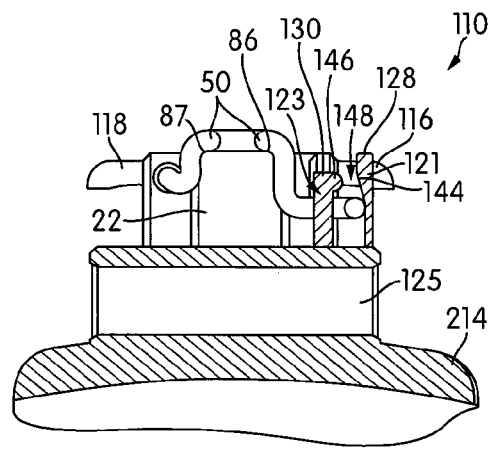
Figure 28E:
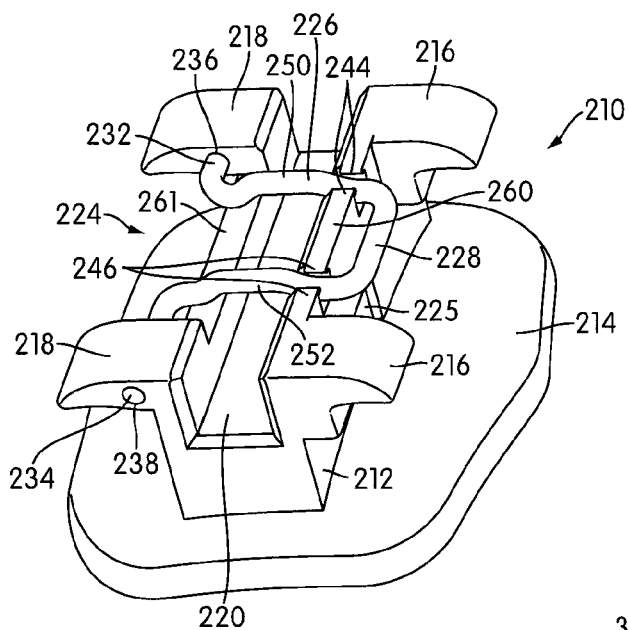
Figure 28F:
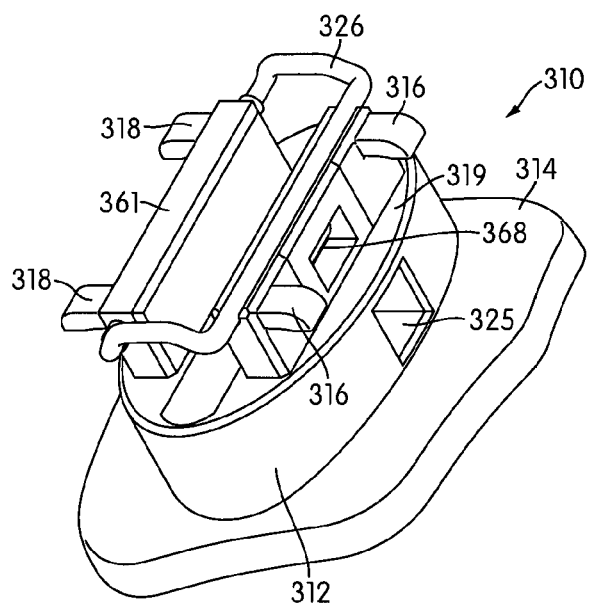
Figure 28G:
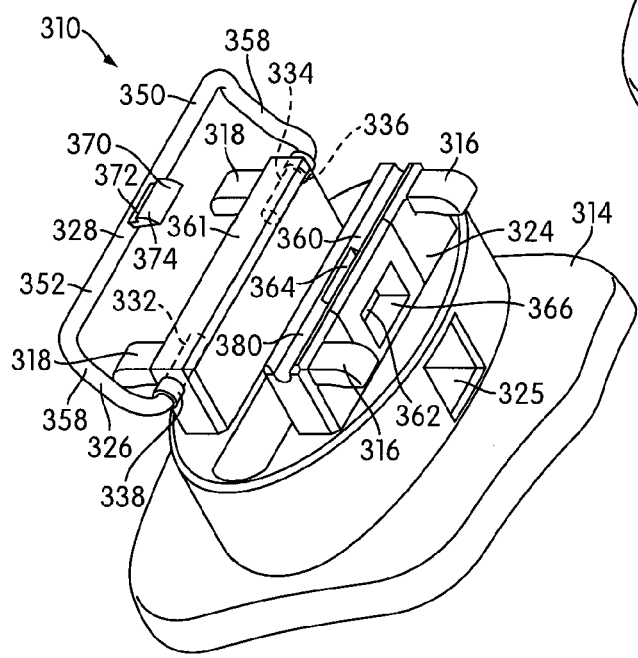
Figure 28H:
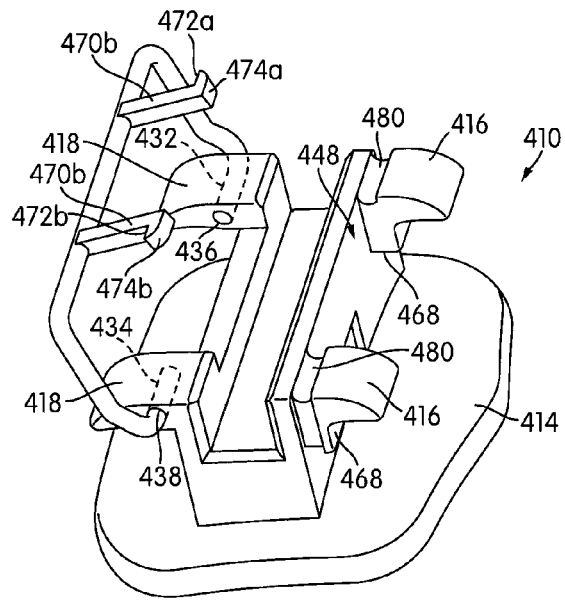
Figure 28I:
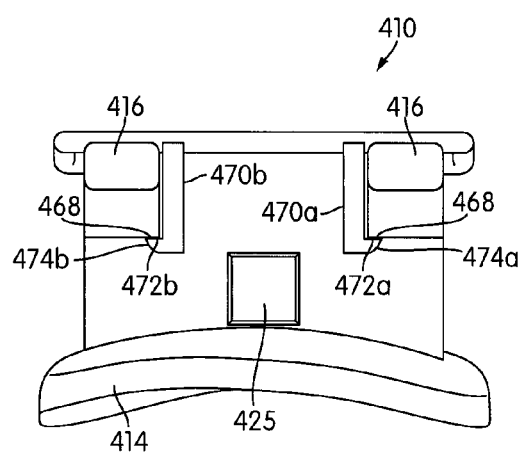

FIG. 28I is a front view of the embodiment shown in FIG. 28H in a closed position.

Figure 28J:
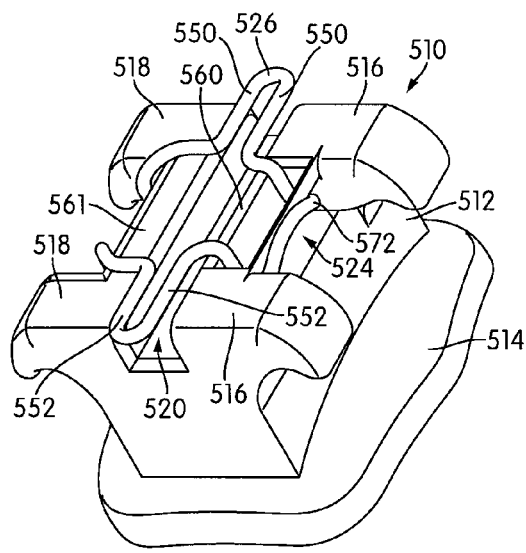

FIG. 28J is a perspective view of another embodiment of the present invention in a closed position.

Figure 28K:
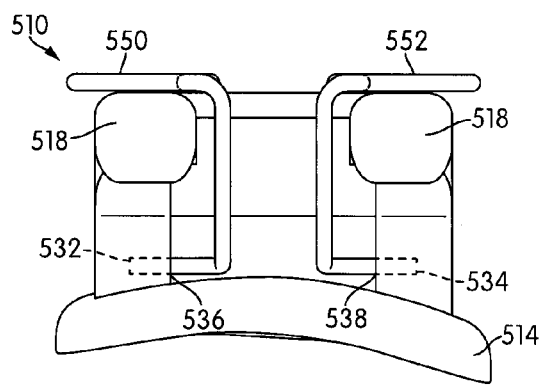

FIG. 28K is a front view of the embodiment shown in FIG. 28J.

Figure 29A:
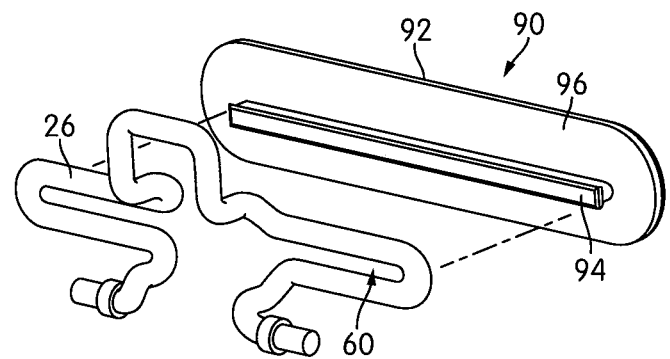

FIG. 29A is an exploded perspective view of a locking clip assembly for the embodiment shown in FIG. 28A, which includes a locking clip cover.

Figure 29B:
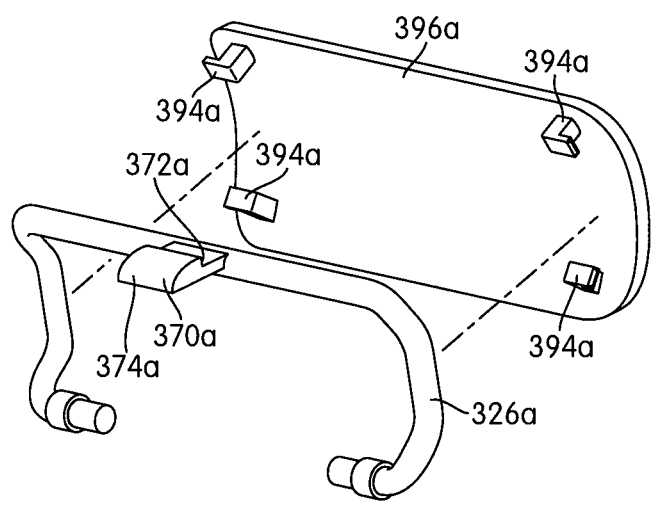

FIG. 29B is an exploded perspective view of a locking clip assembly for the embodiment shown in FIG. 28F, which includes a locking clip cover.

Figure 29C:
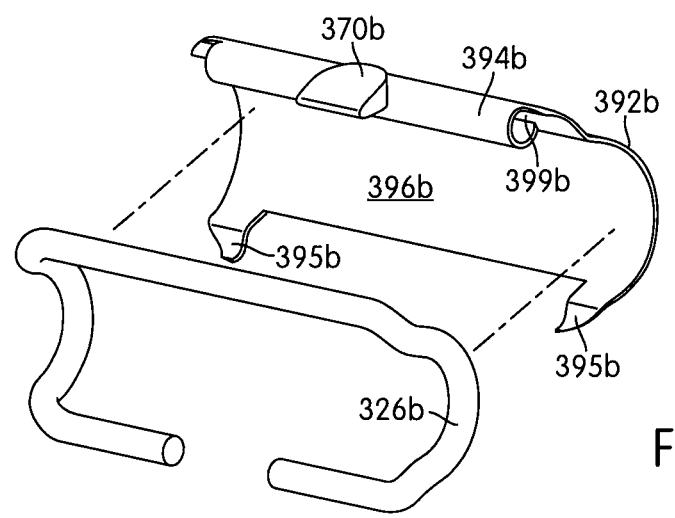

FIG. 29C is an exploded perspective view of another locking clip assembly for the embodiment shown in FIG. 28F, which includes a locking clip cover.

Figure 30A:
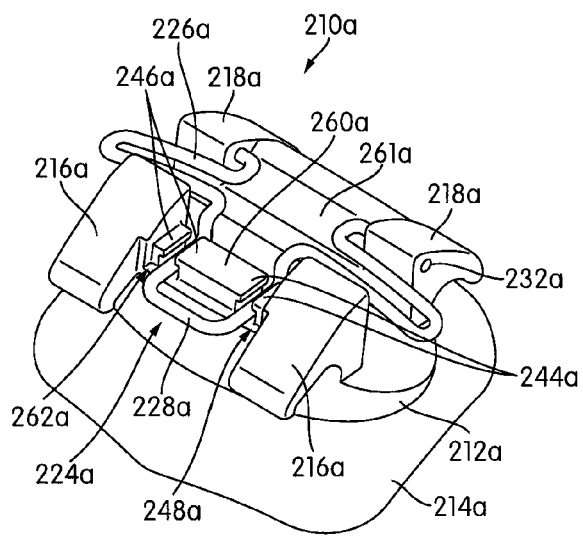

FIG. 30A is a top perspective view of another embodiment of the present invention in the closed position with a curved archwire slot surface and base portion without a vertical slot.

Figure 30B:
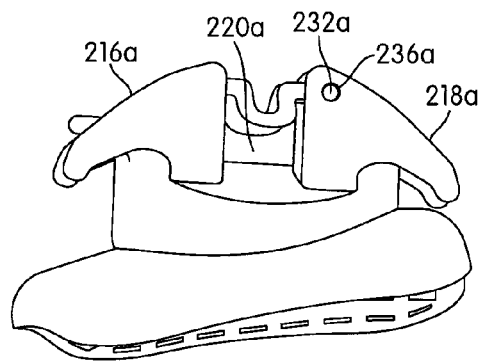

FIG. 30B is a side view of the embodiment shown in FIG. 30A.

Figure 30C:
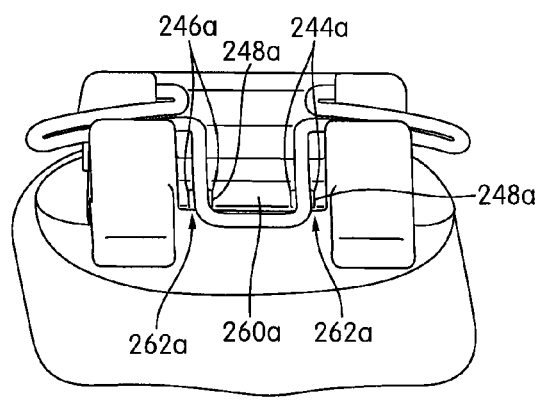

FIG. 30C is front perspective view of the embodiment shown in FIG. 30A.

Figure 30D:
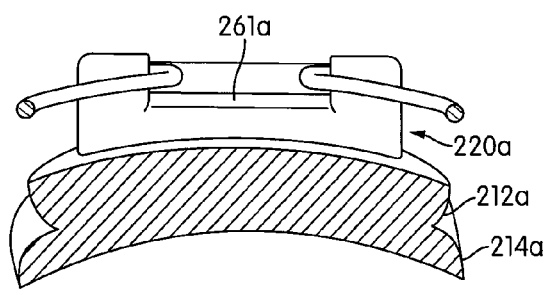

FIG. 30D is a cross-section view of the embodiment shown in FIG. 300.

FIG. 30E is a top perspective view of another embodiment of the present invention in the closed position with a curved archwire slot surface and base portion with vertical slot.

FIG. 30F is a side view of the embodiment shown in FIG. 30E.

FIG. 30G is a top perspective view of another embodiment of the present invention in the closed position with a curved archwire slot surface and base portion without a vertical slot.

FIG. 30H is a side view of the embodiment shown in FIG. 30G.

FIG. 30I is a top perspective view of another embodiment of the present invention in the closed position with a curved archwire slot surface and base portion with vertical slot.

FIG. 30J is a side view of the embodiment shown in FIG. 30I.

FIG. 30K is a top perspective view of another embodiment of the present invention in the closed position with a curved archwire slot surface and base portion without a vertical slot.

FIG. 30L is a side view of the embodiment shown in MG. 30K.

Figure 31A:
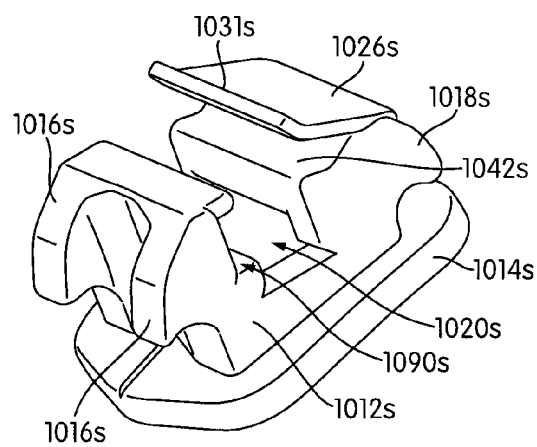

FIG. 31A is a top perspective view of another embodiment of the present invention.

Figure 31B:
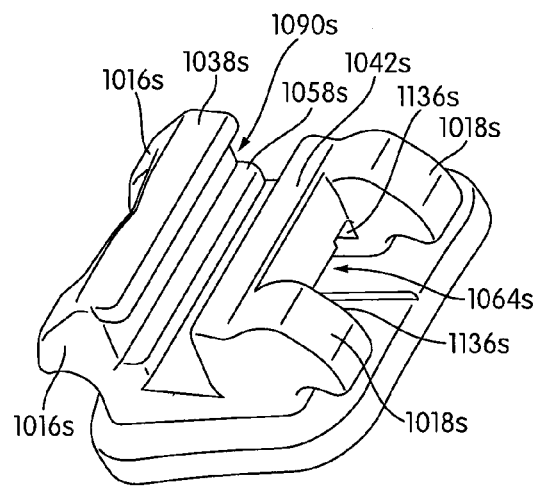

FIG. 31B is another top perspective view of the embodiment shown in FIG. 31A without a locking clip.

Figure 31C:
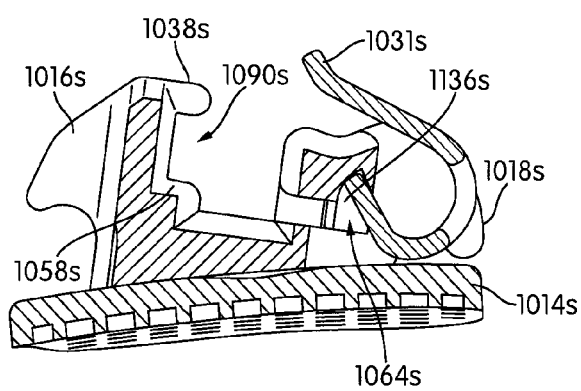

FIG. 31C is a cross-section view of the embodiment shown in FIG. 31A.

Figure 31D:
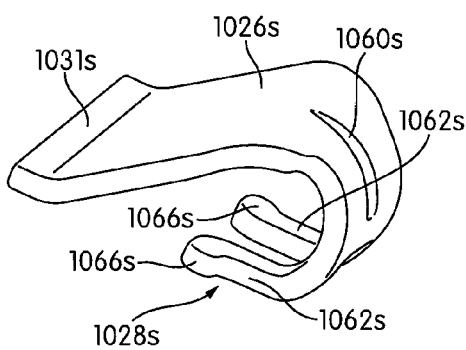

FIG. 31D is a rear perspective view of the locking clip from the embodiment shown in FIG. 31A.

DESCRIPTION OF INVENTION

It is appreciated that the present invention provides for several embodiments of a self-ligating orthodontic bracket assembly that includes a bracket and a locking clip(s). The bracket has a closed position in which the clip inhibits access to an archwire slot and an open position in which the clip allows access to the archwire slot.

Generally, the illustrated bracket includes a body and a base. The body may include the archwire slot (two receiving areas positioned mesially and distally of the bracket body), a first tie wing (e.g., gingival tie wing(s)), a second tie wing (e.g., occlusal tie wing(s)), and an interwing region extending gingivally-occlusally across the body and may be generally defined by at least one of the lateral spacing or a bridge portion of the gingival tie wings and the lateral spacing or a bridge portion of the occlusal tie wings. The base connects the bracket to a tooth and may include an attachment portion that defines a pattern, which receives an adhesive and is shaped to affix to the tooth. In one specific embodiment, the lingual side of the attachment portion affixes to the labial side of the tooth. In the construction, the base may be attached to the body with welds. In other constructions, the base may be attached in other ways or formed as a single piece with the body.

Figure 1A:
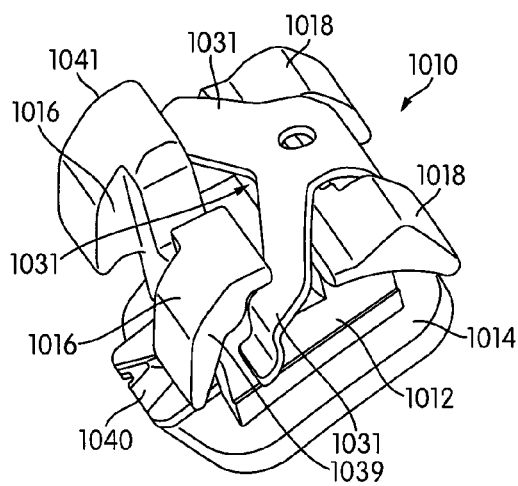
FIG. 1A is a top perspective view of a first embodiment of the present invention.
Figure 1B:
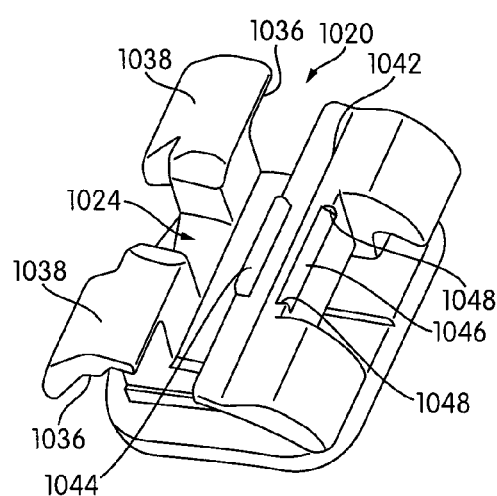
FIG. 1B is another top perspective view of the embodiment shown in FIG. 1A without a locking clip.
Figure 1C:
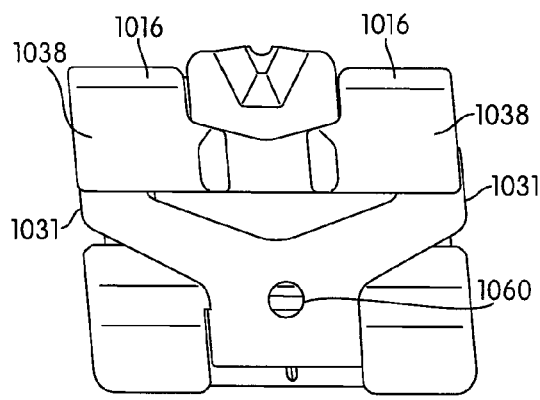
FIG. 1C is a top view of the embodiment shown in FIG. 1A.
Figure 1D:
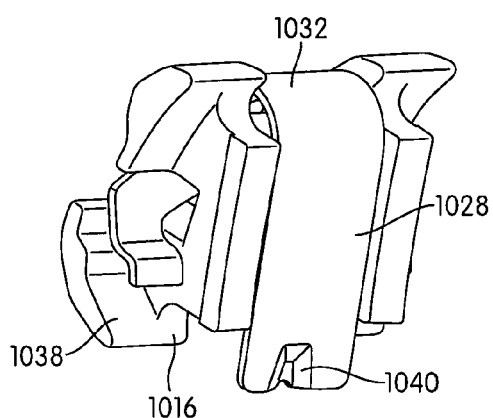
FIG. 1D is bottom perspective view of the embodiment shown in FIG. 1A without a base portion.
Figure 1E:
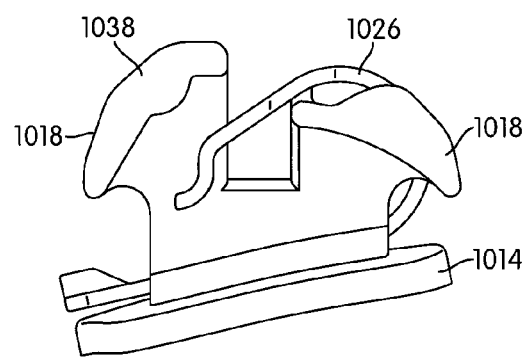
FIG. 1E is a side view of the embodiment shown in FIG. 1A.
Figure 1F:
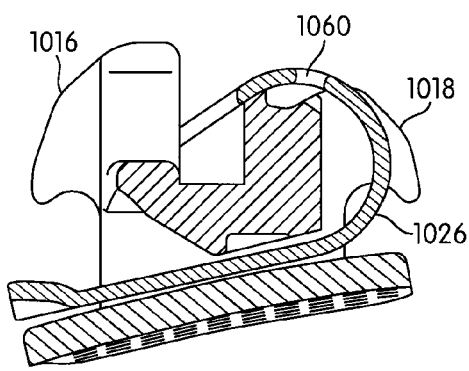
FIG. 1F is a cross-section view of the embodiment shown in FIG. 1E.

Referring now to FIGS. 1A to 1F, a self-ligating orthodontic bracket is shown and is generally indicated to by reference numeral 1010. FIG. 1A is a perspective view of a self-ligating dental bracket in a closed position in accordance with the present invention with a lateral spacing between the gingival tie wings and a labial portion (e.g., hood portion) extending from the respective mesial and distal gingival tie wings to form the receiving areas. The labial portions extending outside the mesial and distal sides of the body for receiving a tab portion (e.g., a prong) of the clip. The labial free end of the clip (e.g., gingival tip portion) includes the tab portions of the clip, which may be contoured to match the contour of the receiving area beneath the hood portions of the gingival tie wings.

More particularly, the orthodontic bracket 1000 includes a body 1012 and a lingual mounting base 1014 attached to the body. The mounting base 1014 has a lingual surface to be attached to a tooth. Generally, the body 1012 defines a square, rectangle, or otherwise shaped member. However, it is appreciated that the body 1012 may be defined by various other shaped configurations such as a rhombus-shaped, a circular-shaped, an oval-shaped, or otherwise shaped member.

A pair of laterally spaced gingival tie wings 1016 and a pair of laterally spaced occlusal tie wings 1018 extend from the labial surface of the body 1012. The gingival tie wings 1016 and the occlusal tie wings 1018 generally curve lingually. An interwing region 1024 extends gingivally-occlusally across the body 1012 and may be generally defined by the lateral spacing of the gingival tie wings 1016 and/or the lateral spacing of the occlusal tie wing 1018. The interwing region 1024 may be an opened (e.g., unobstructed) passageway or may be a closed (partially or completely obstructed) passageway FIGS. 1A-1F, or otherwise. An archwire slot 1020 extends mesially-distally across the body 1012 and between the gingival and occlusal tie wings 1016 and 1018. The archwire slot 1020 opens labially to receive an archwire (not shown). The archwire slot 1020 may be interrupted in the interwing region 24 of the body.

The bracket 1010 may further include a locking mechanism that includes a locking clip 1026 for maintaining the archwire in the archwire slot 1020 while in the closed position. This locking clip 1026 is structured in a substantially U-shaped cross-sectional configuration, and one side thereof is formed as a lingual free end 1028 (a portion located on the lingual side) located on the base side and extending along the base (through an opening formed between the body 1012 and the base 1014), while the other side thereof is formed as a labial free end 1030 having substantially the same width as the length of the arch wire slot 1020 and extending on the upper side of the slot. The lingual free end 1028 and the labial free end 1030 may be interconnected by a curved portion 1032.

The locking clip 1026 may be formed of an elastic member in which a notched portion 1034 is provided substantially in the center of a tip edge portion of the labial free end 1030 (a portion located on the labial side). The notch portion 1034 may be defined by left and right (e.g., mesial and distal) tab portions 1031 of the counter base portion 1028, which is the T or Y-shape head portion in the substantially T or Y-shaped configuration of the locking clip 1026.

Further, since the notched portion 1034 of the locking clip may correspondingly be provided for the width of the bracket body (e.g., mesial/distal free/open edge portions) so as to be fitted to it, the shift and twisting of the tab portions of the locking clip 1026 in the longitudinal direction of the slot can be effectively suppressed. Namely, with respect to the shift and twisting of the tip portion of the locking clip 1026 in the longitudinal direction of the body, such shift can be suppressed by a receiving area provided about a mesially side and/or a distally side of the bracket body 1012.

The receiving area may be defined by a receiving member 1036 extending from the outer free/open edge of the bracket body 1012. Preferably, the outer free/open edge of the bracket body is generally coplanar with the mesial/distal free ends of the archwire slot 1020, though not required. In one specific example as shown in FIGS. 1A-1F, the receiving member 1036 may include a labial hood portions 1038 extending mesially/distally from the outer free/open edge of the gingival tie wing 1016 of the bracket body 1012. The labial hood portion may be provided for stopping a tip of the locking clip 1026 (e.g., tabs 1031) at a slot closed position at a free/open edge portion of the bracket body. More particularly, a mesial labial hood portion 1039 may extending mesially from the mesial free/open edge portion of the bracket body (e.g., mesially extending from the mesial-gingival tie wing) and a distal labial hood portion 1038b may extend distally from a distal free/open edge portion of the bracket body (e.g., distally extending from the distal-gingival tie wings). Desirably, the labial hood portions 1039 and 1038b prevent the arch wire from unintentionally being removed from the archwire slot 1020 by limiting labial movement of the locking clip 1026 while in the closed position.

The locking clip 1026 may further include an engaging end portion 1040, which can be formed by a notched portion, a recessed portion, a projection, or the like. The engaging end portion may be formed at a rear end portion of the lingual free end 1028 in the locking clip 1026. The engaging end portion 1040 may be configured to aid in moving the locking clip 1026 from the closed position to an open position through contact by a tool or otherwise. By way of example, a tool may contact the engaging end portion so that the lingual free end 1028 moves occlusally thereby moving the labial free end 1030 occlusially away from the hood portions 1039 and 1038b to an open stop groove 1042 about the labial surface of the occlusal tie wings 1018 so that the locking clip 1026 may be maintained in the open position.

When included, the open stop groove 1042 may be provided in the interwing region 1024 connecting the occlusal tie wings therebetween. Furthermore, the open stop groove 1042 may include a mesial-distal protrusion 1044, which does what? The open stop groove 1042 may further include a mesial-distal depression 1046 having mesial and distal edge walls 1048. The depression 1046 having substantially the same width as the curved portion 1032 of the locking clip 1026 so that the edge walls 1048 can minimize the mesial-distal shift of the locking clip 1026 resulting from an unexpected force being applied on the bracket. Optionally, the interior walls 1050 of the occlusal tie wings may also minimize the mesial-distal shift of the locking clip 1026 resulting from an unexpected force being applied on the bracket in addition to or in place of the depression 1046 (desirably a locking clip having a curved portion with a width corresponding to the width of the interwing region between the occlusal tie wings).

Figure 2A:
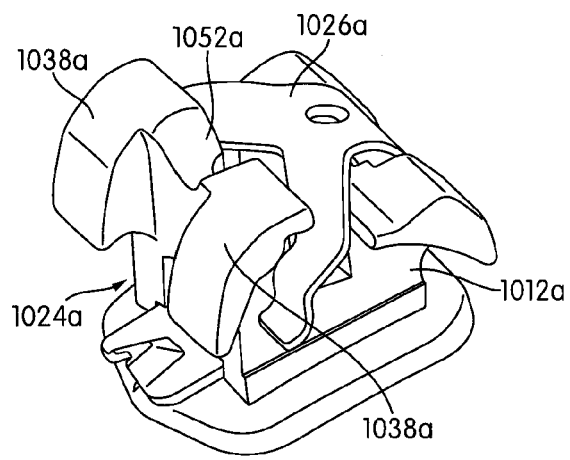
FIG. 2A is a top perspective view of a second embodiment of the present invention.
Figure 2B:
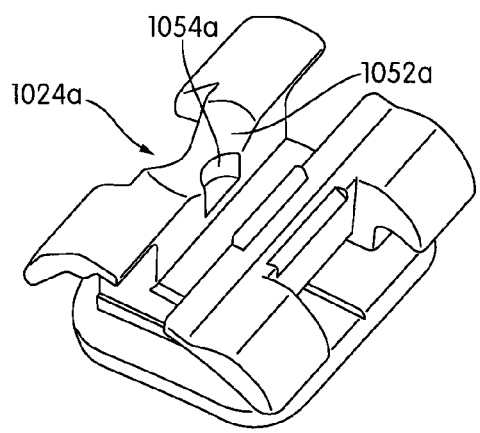
FIG. 2B is another top perspective view of the embodiment shown in FIG. 2A without a locking clip.
Figure 2C:
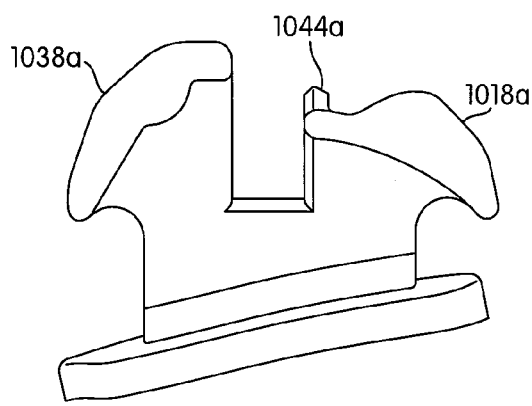
FIG. 2C is a side view of the embodiment shown in FIG. 2A.

FIGS. 2A-2C are various views of an alternate embodiment of a self-ligating bracket shown in FIG. 1A. As such the present invention may provide a self-ligating bracket 1010a having a bracket body 1012a, a base 1014, a locking clip 1026 and a bridge portion 1052a in the gingival interwing region 1024a so as to connect the interior mesial side of gingival-distal tie wing with the interior distal side of the gingival-mesial tie wing. Optionally, the bridge portion 1052a may include a depression 1054a having an opening 1056a to allow for access of a dental tool to aid in the opening and/or closing of the bracket 1010a.

FIGS. 3A-3E are various views of another alternate embodiment of the self-ligating bracket shown in FIG. 2A in which the present invention may include a self-ligating bracket 1010b having a bracket body 1012b, a base 1014, a locking clip 1026b and a receiving member 1036b. The receiving member may further include at least one lingual ledge 1058b. Lingual ledges 1058b may be provided as separate artifacts that mesially and distally extend from the respective sides of the body 1012b in a location lingually spaced from the hood portions 1038b. Lingual ledges 1058b may be configured to minimize and/or substantially prevent lingual movement of the locking clip 1026b. In this specific example, the hood portions 1038b have been reduced/thinned (gingivally-occlusally) and the gingival tip of the tab portions of the clip may be bent slightly labially for enhanced interactivity. Furthermore, the curved portion 1032b of the locking clip 1026b may include a throughhole 1060b, which corresponds with a depression 1046b of the open-stop groove 1042b to allow for access of a dental tool to aid in the opening and/or closing of the bracket 1010b.

Bracket 1010b may further include an alternate locking mechanism having a modified lingual free end of the locking clip being received by the lingual opening of the bracket. More particularly, the locking clip 1026b may include a lingual free end 1028b having a plurality of spaced apart deformable fingers 1062b for engagement with a lingual opening 1064b formed at an occlusal portion of the body. The deformable fingers 1062b having outwardly extending mesial/distal flange portions 1066b at a gingival free end. The lingual opening 1064b extending into a cavity 1068b having a larger width than the width of the lingual opening 1064b to prevent the deformable fingers from passing through the lingual opening (while in a non-stressed state) and separating from the clip. Desirably the deformable fingers 1062b are deformed towards one another such that the width between the outer edges of the flange portion is less than the lingual opening 1064b so that the lingual free end 1028b of the locking clip 1026b may be inserted through the lingual opening 1064b and into the lingual cavity 1068b for securement therein. Once the lingual free end of the locking clip is received into the lingual cavity, the deformable fingers substantially return to their non-stressed state/position. Optionally, once received in the lingual cavity, the deformable fingers may remain in a partially stressed state due to active engagement of the outer edges 1070b of the flange portions with the respective mesial and distal side walls 1072b of the lingual cavity to aid in suppressing movement (e.g., twisting, mesial-distal movement, and/or otherwise).

FIGS. 4A-4D are various views of another alternate embodiment of the self-ligating bracket shown in FIGS. 3A-3E in which the receiving member 1036c may further include end walls 1074c interconnecting the labial hoods 1038c and the lingual ledges 1058c to define a perimeter around a throughhole 1076c in the receiving areas to cover and protect the mesial and distal tab portions 1031c of the locking clip 1026c while in the closed position. As in FIGS. 3A-3E, the gingival tie wings 1016c have been reduced/thinned (gingivally-occlusally) and the gingival tip of the tab portions 1031c may be bent slightly labially for enhanced interactivity. Furthermore, the width of the notched portion 1034c at the tab portions 1031c may be correspondingly provided to fit the width of the bracket body 1012c to suppress shifting and/or twisting of the locking clip 1026c while in the closed position.

FIGS. 5A-5F are various views of another alternate embodiment of the self-ligating bracket shown in FIGS. 3A-3E in which the receiving member 1036d may further include a separate artifact as mesial-distal extension 1078d to the gingival tie wings 1016d. The mesial-distal extensions 1078d being configured to interconnect the labial hood portions 1038d with the respective lingual ledges 1058d in the shape of a "c-cup" to retain the tab portions 1031d of the locking clip 1026d while in the closed position.

Figure 5A:
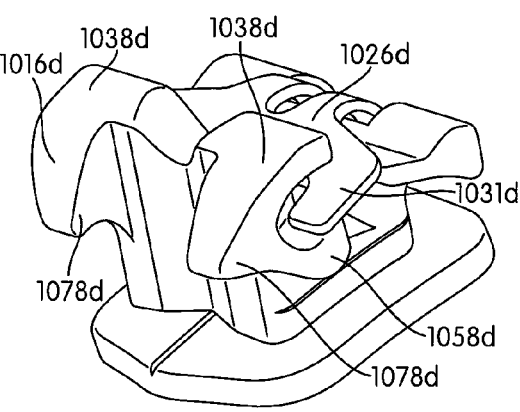
FIG. 5A is a top perspective view of a fifth embodiment of the present invention.
Figure 5B:
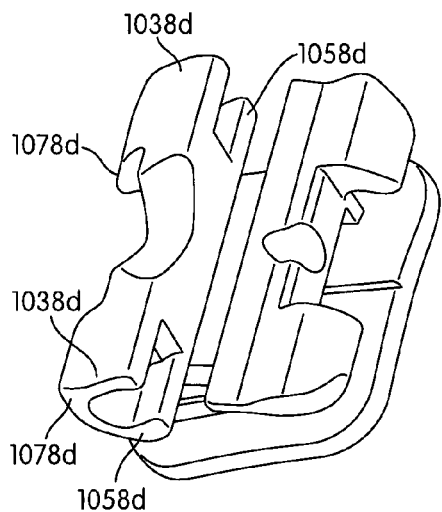
FIG. 5B is another top perspective view of the embodiment shown in FIG. 5A without a locking clip.
Figure 5C:
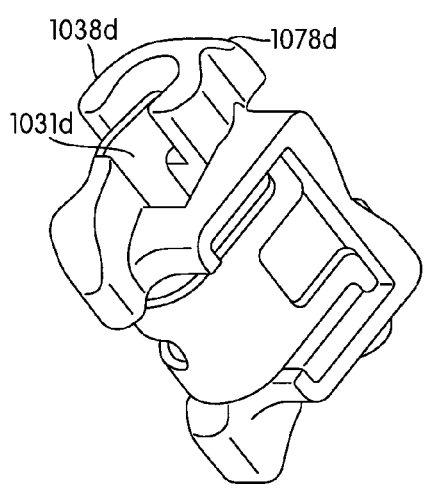
FIG. 5C is bottom perspective view of the embodiment shown in FIG. 5A without a base portion.
Figure 5D:
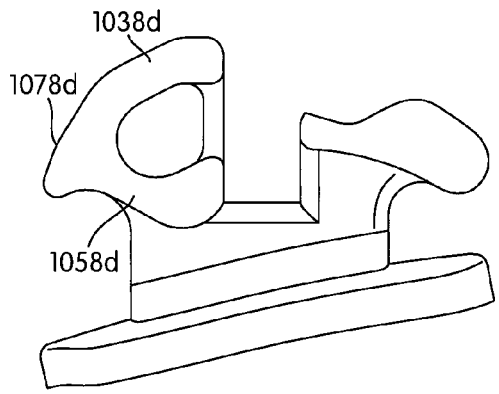
FIG. 5D is a side view of the embodiment shown in FIG. 5A.
Figure 5E:
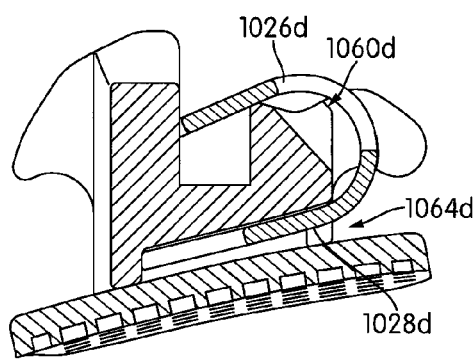
FIG. 5E is a cross-section view of the embodiment shown in FIG. 5D.

FIG. 5E is a cross-sectional view of the self-ligating dental bracket in FIG. 5A, which further illustrates a depression/chamfer 1046d in the open stop groove 1042d of the body 1012d between the occlusal tie wings 1018d to guide a standard dental instrument to facilitate the opening of the locking clip 1026d.

Figure 6A:
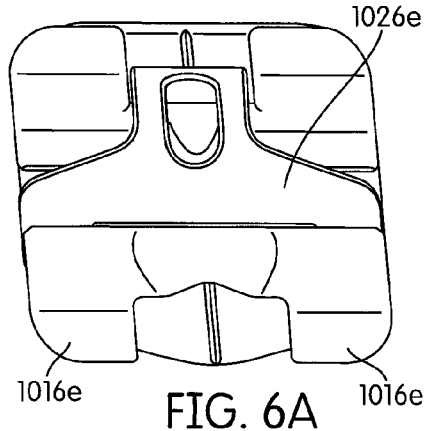
FIG. 6A is a top view of a sixth embodiment of the present invention.
Figure 6B:
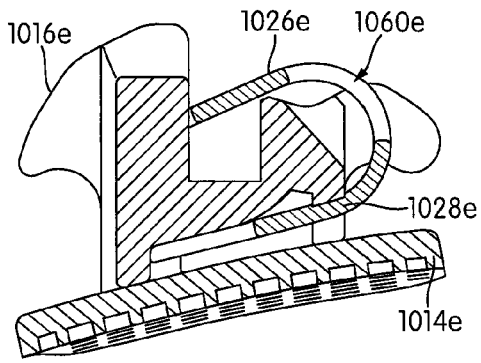
FIG. 6B is a cross-section view of the embodiment shown in FIG. 6A.
Figure 6C:
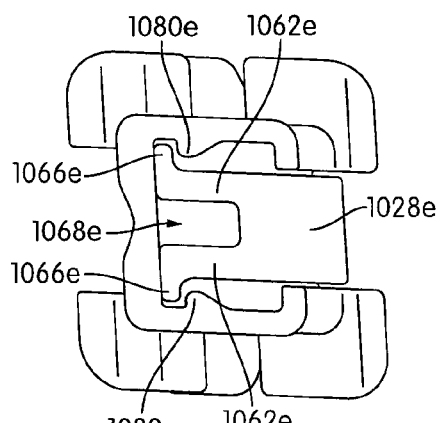
FIG. 6C is bottom view of the embodiment shown in FIG. 6A without a base portion.
Figure 6D:
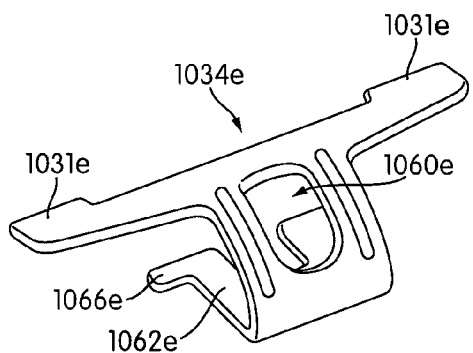
FIG. 6D is a rear perspective view of the locking clip from the embodiment shown in FIG. 6A.

FIGS. 6A-6C are various views of another alternate embodiment of the self-ligating bracket shown in FIGS. 5A-5E in which an alternate locking mechanism may be provided. The alternate locking mechanism may include ratchet portions 1080e about the respective side walls 1072e (e.g., mesial and distal side walls) of the lingual cavity 1068e to substantially maintain each flange portion 1066e of the lingual free end 1028e of the locking clip 1026c in a generally predetermined position 1082e and/or area of the lingual cavity 1068e while in the closed position. The ratchet portions 1080e may further include tapered occlusal end portions 1084e to facilitate movement of the lingual free end 1028e to the predetermined (gingival) area 1082e of the lingual cavity.

FIG. 6B is a cross-sectional view of an alternate embodiment of the body and clip of a self-ligating dental bracket shown in FIG. 5E in which the clip slides gingivally toward the open position before the lingual free end of the clip slightly pivots labially at the near-open position.

FIG. 6C is a bottom view of the body and clip in FIG. 6A in which the lingual free end of the locking clip locks securely in the closed position. When the clip slides gingivally toward the open position, the lingual free end of the clip will be guided by the tapered opening in the lingual portion of the body.

FIG. 6E is a perspective view of the locking clip 1026e may further include a least one grooves 1086e extending (e.g., labially-lingually) about the curved portion 1032e. In one specific example, the locking clip 1026e includes a pair of labially-lingually extending grooves 1086e, though not required. The grooves 1086e may provide additional reinforcement to the locking clip 1026e to suppress shifting and/or twisting of the locking clip 1026e while in the closed position . . . . IS THIS TRUE?

Figure 7A:
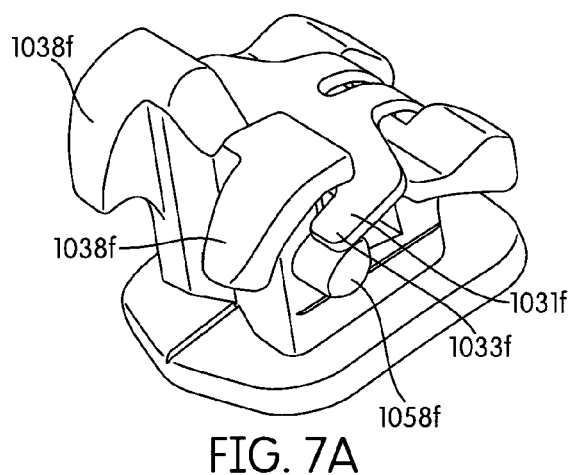
FIG. 7A is a top perspective view of a seventh embodiment of the present invention.
Figure 7B:
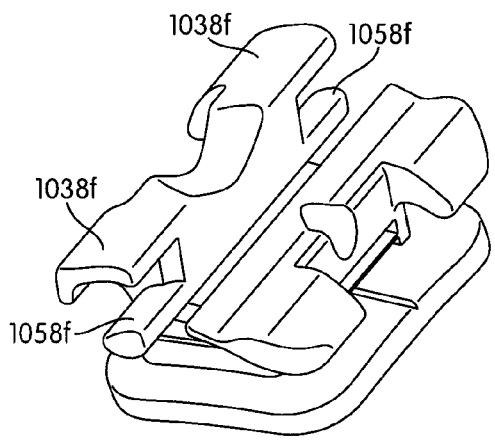
FIG. 7B is another top perspective view of the embodiment shown in FIG. 7A without a locking clip.
Figure 7C:
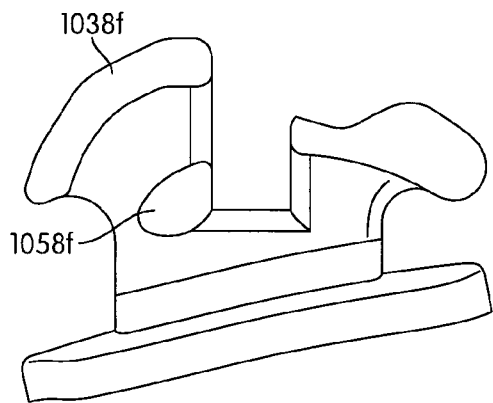
FIG. 7C is a side view of the embodiment shown in FIG. 7A.
Figure 8A:
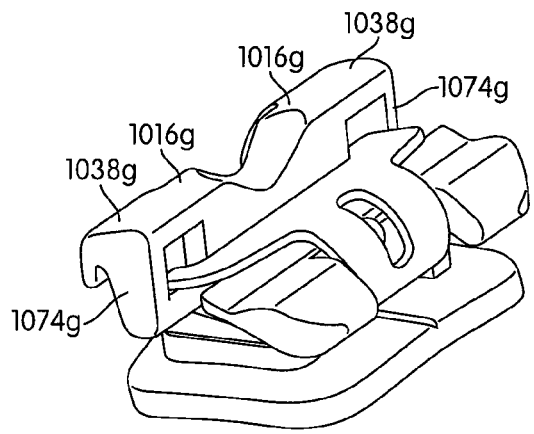
FIG. 8A is a top perspective view of an eighth embodiment of the present invention.
Figure 8B:
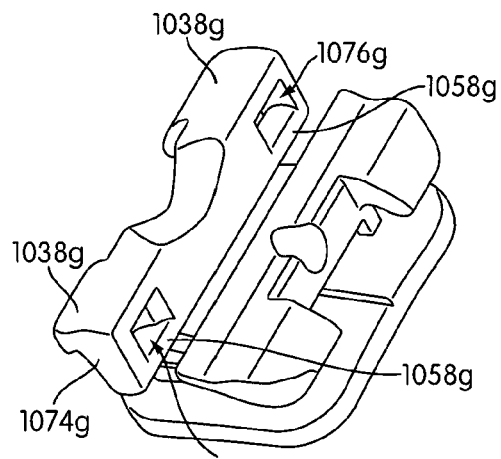
FIG. 8B is another top perspective view of the embodiment shown in FIG. 8A without a locking clip.
Figure 8C:
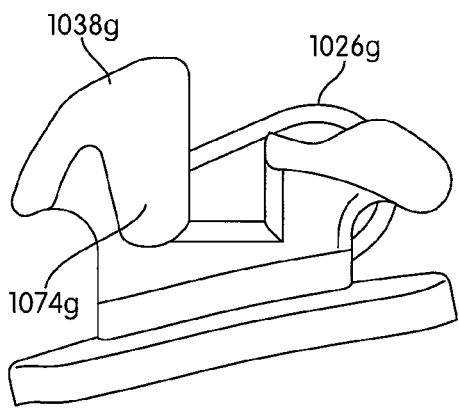
FIG. 8C is a side view of the embodiment shown in FIG. 8A.
Figure 8D:
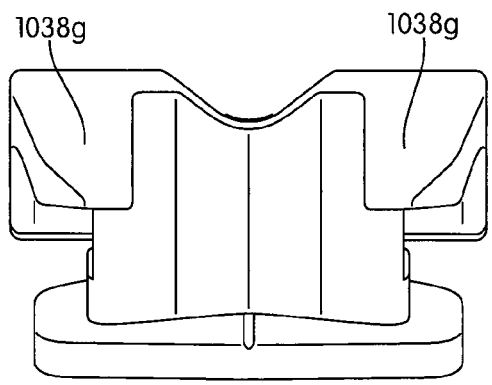
FIG. 8D is a front view of the embodiment shown in FIG. 8A.
Figure 8E:
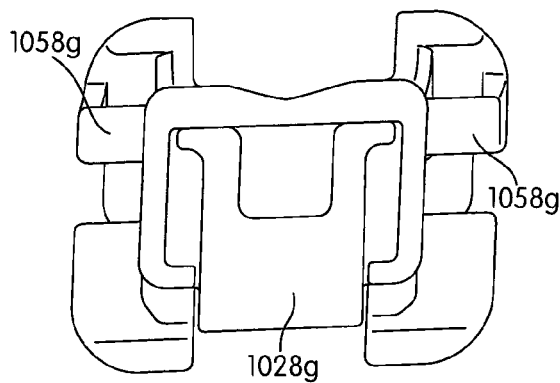
FIG. 8E is bottom view of the embodiment shown in FIG. 8A without a base portion.

FIGS. 7A-7C are various views of another alternate embodiment of the self-ligating bracket shown in which the receiving member 1036f may include full hood portions 1038f similar to the alternate embodiment shown in FIG. 1A (e.g., not having a reduced in thickness) while further including lingual ledges 1058f. In this specific embodiment, the gingival tip portions 1033f of the tab portions 1031f may remain generally flat.

FIGS. 8A-8E are various views of another alternate embodiment of the self-ligating bracket shown in FIGS. 4A-4D in which the receiving member 1036g may further include full hood portions 1038g extending from the respective gingival tie wings 1016g thereby providing an increased labial surface 1088g about the gingival tie wings 1016g. In doing so, the hook portions 1019g of the gingival tie wings 1018g may extend lingually, at least partially covering the gingival side of the throughhole 1076g1.

FIGS. 9A-9H are various views of another embodiment of the self-ligating bracket of the present invention in which the bracket 1010h includes a modified locking clip 1026h and a modified receiving member 1036h. In this specific embodiment, the receiving member 1036h may be centrally located about the bracket body 1012h and may include a continuous retaining (e.g., resting) channel 1090h to allow a positive seat for retaining the locking clip 1026h. Desirably, the retaining channel 1090h extends generally in a parallel manner to the archwire slot 1020h between the respective mesial and distal sides of the bracket body 1012h. In this specific embodiment, the width of the locking clip 1026h at the labial free end 1030h may be been reduced to generally the same mesial-distal width of the bracket body 1012h. Furthermore, the labial free end 1030a of the locking clip 1026h may include a single tab portion 1031h (e.g., generally free of a notch), which generally corresponds with the retaining channel 1090h. The retaining channel may be further defined by a generally c-shaped profile to not only provide a positive seat (and limit lingual movement of the labial free end 1030h), but may also provide a hood portion 1038h to limit labial movement of the labial free end 1030h while in the closed position. Optionally, the height (e.g., labial-lingual height) of the retaining channel 1090h may be sufficiently sized (e.g., less than or equal to the thickness of the archwire) so that archwire entrapment therein may be substantially prevented while the free end portion 1030h of the locking clip 1026h is in the closed position.

Figure 9A:
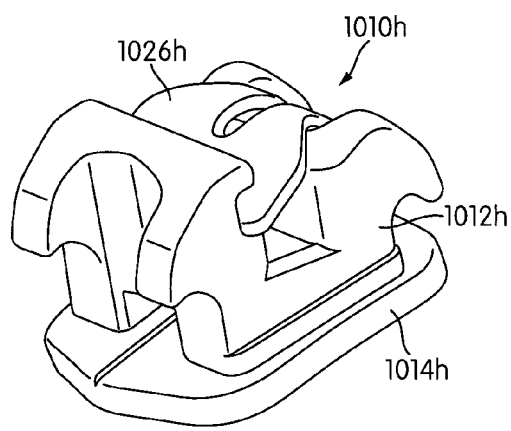
FIG. 9A is a top perspective view of an ninth embodiment of the present invention.
Figure 9B:
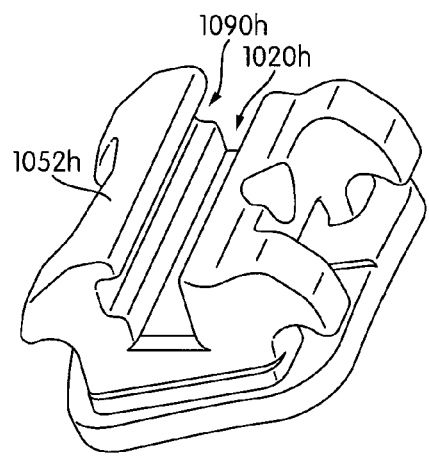
FIG. 9B is another top perspective view of the embodiment shown in FIG. 9A without a locking clip.
Figure 9C:
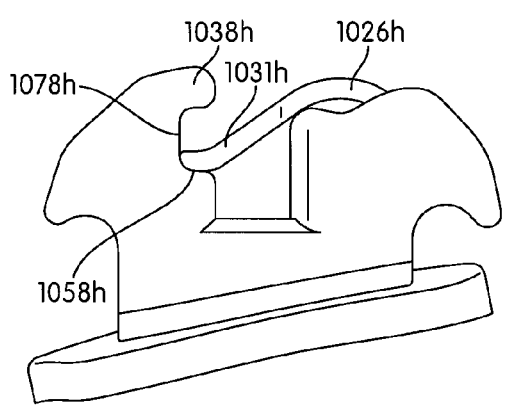
FIG. 9C is a side view of the embodiment shown in FIG. 9A.
Figure 9D:
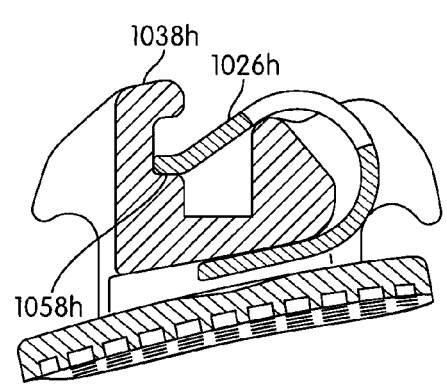
FIG. 9D is a cross-section view of the embodiment shown in FIG. 9C
Figure 9E:
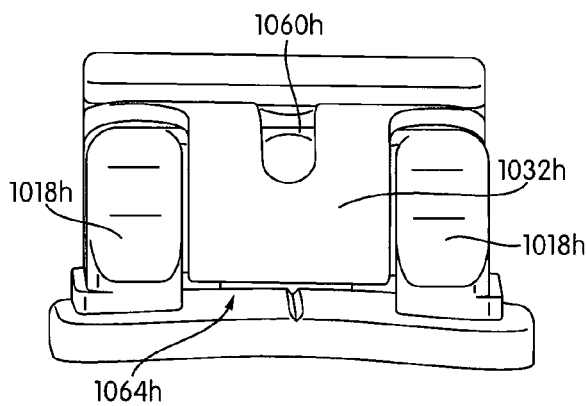
FIG. 9E is a front view of the embodiment shown in FIG. 9A.
Figure 9F:
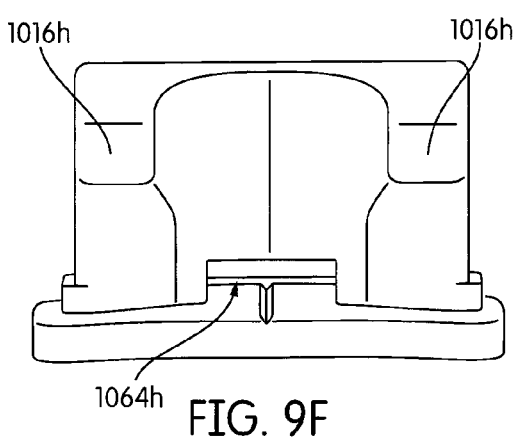
FIG. 9F is rear view of the embodiment shown in FIG. 9A.

FIG. 9F is a gingival view of the self-ligating dental bracket 1010h shown in FIG. 9A that incorporates a lingual opening 1064h (e.g., throughhole), which is a continuous channel extending between the gingival tie wings 1016h and the occlusal tie wings 1018h towards the lingual portion of the body to facilitate the cleaning of entrapped calculus/tartar.

Figure 9G:
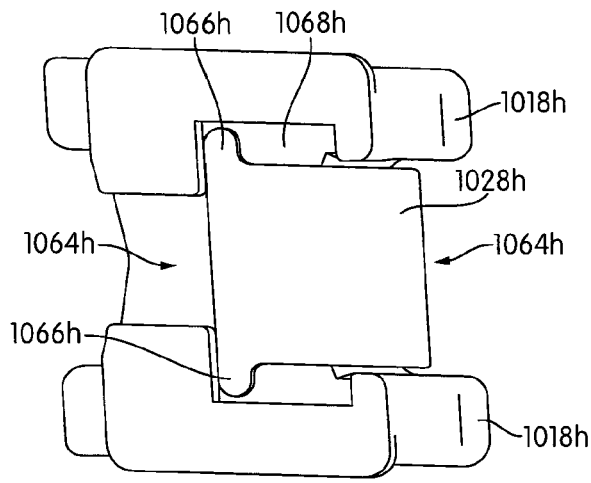
FIG. 9G is bottom view of the embodiment shown in FIG. 9A without a base portion.

FIG. 9G is a bottom view of the body 1012h and locking clip 1026h of a self-ligating dental bracket shown in FIG. 9A while in a closed position with the base removed. In this specific embodiment, the lingual opening 1064h extends completely through the lingual portion of the body 1012h (as discussed above) while the area of the lingual cavity 1068h has been reduced.

FIGS. 10A-10B, 10C-10D, 11A-11C, 12A-12C, 13A-13C, 14A-14C, 15A-15C, and 16A-16C are various views of alternate locking mechanisms of the self-ligating dental brackets of the present invention.

Figure 9H:
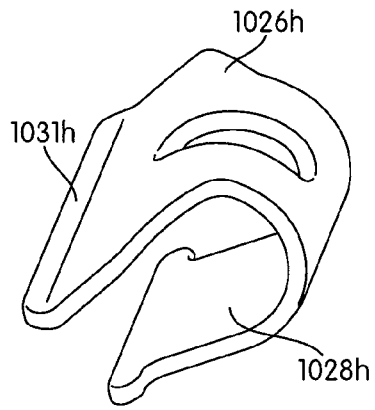
FIG. 9H is a rear perspective view of the locking clip from the embodiment shown in FIG. 9A.

FIGS. 10A-10D are various views of an alternate embodiment of the self-ligating dental bracket shown in FIGS. 9G-9H in which the lingual cavity 1068m has.

Figure 10A:
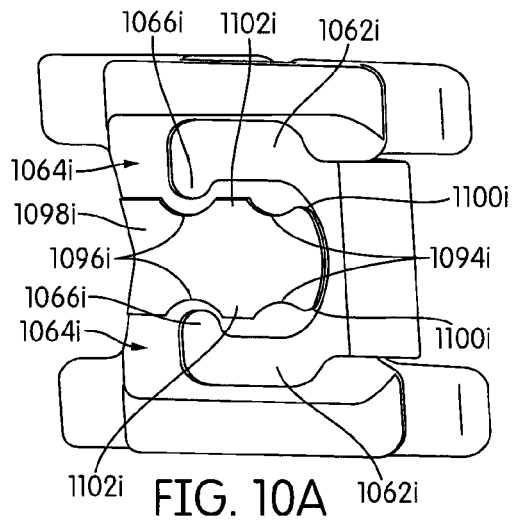
FIG. 10A is a bottom view of a tenth embodiment of the present invention.
Figure 10B:
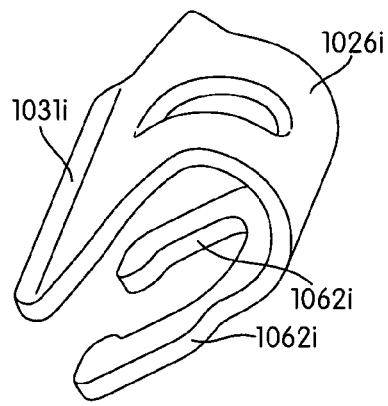
FIG. 10B is a rear perspective view of the locking clip from the embodiment shown in FIG. 10A.

FIGS. 10A-10B provide self-ligating bracket 1010i, which may include a modified locking arrangement having a locking clip 1026i and a lingual cavity 1068i having a centrally located stabilizing member with locking grooves/ratchets to facilitate and securely lock the lingual free end of the locking clip in both the opened and closed positions. In this specific embodiment, the locking clip 1026i includes a Y-shaped/U-shaped lingual free end 1028i having deformable fingers 1062i. The deformable fingers 1062i may include inwardly extending flange portions 1066i that are configured to actively engage open position grooves 1094i (to aid in maintaining the bracket in the open position) or closed position grooves 1096i (to aid in maintaining the bracket in the closed position) of a stabilizing member 1098i. The stabilizing member 1098i may be located generally in a central region (e.g., generally parallel to the interwing region 1024i) of the lingual cavity 1068i, though not required. In this specific embodiment, the stabilizing member 1098i extends from the gingival side of the lingual opening 1064 to an intermediate position within the lingual cavity 1068i so that each deformable finger 1062i extends along at least one side of the stabilizing member 1098i.

In use, the deformable fingers compress towards one another to reduce the overall width of the lingual free end portion 1028i for insertion into through the lingual opening. Once the lingual free end portion extends through the lingual opening 1064i, the deformable fingers return to a non-stressed position, which includes a width generally smaller than the width of engagement ribs of the stabilizing member 1098i. Insertion of the locking clip 1026h continues into the lingual cavity 1068i, where the flange portions 1066i are deflected outwards upon contacting a first pair of engagement ribs 1100i until the flange portions 1066i are received in the pair of open position grooves 1094i and will remain while the bracket is in the open position. To achieve the closed position, the locking clip 1026i is further inserted (gingivally) into the lingual cavity 1068i, where the flange portions 1066i are again deflected outward upon contacting a second pair of engagement ribs 1102i until the flange portions 1066i are received into the pair of closed position grooves 1096i so that the bracket 1010i is substantially maintained in the closed position. To return the bracket to the open position, the locking clip 1026i is moved occlusally towards the second pair of engagement rings until the flange portions 1066i are received into the open position grooves 1094i. Active engagement of the deformable fingers 1062i (e.g., flange portions 1066i) and the stabilizing member 1098i (closed position grooves) aid in suppressing movement (e.g., twisting, mesial-distal movement, and/or otherwise) of the locking clip 1026i while in the closed position.

The self-ligating dental bracket 1010i may incorporate a lingual opening 1064i (e.g., throughhole), which may include two channels 1064i' extending from the gingival tie wings 1016i to a single channel 1064i'' at the occlusal tie wings 1018i towards at a lingual portion of the body to facilitate the cleaning of entrapped calculus/tartar.

Figure 10C:
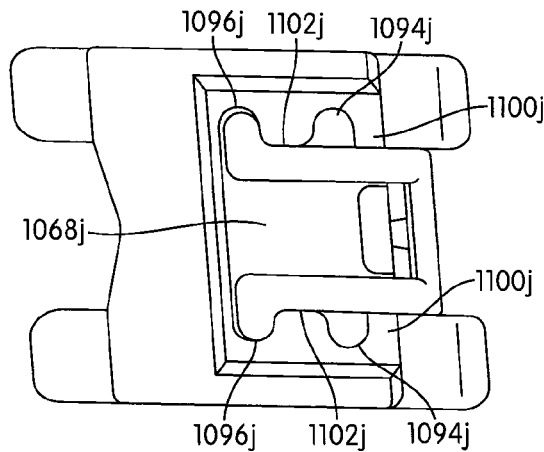
FIG. 10C is a bottom view of another embodiment of the present invention.
Figure 10D:
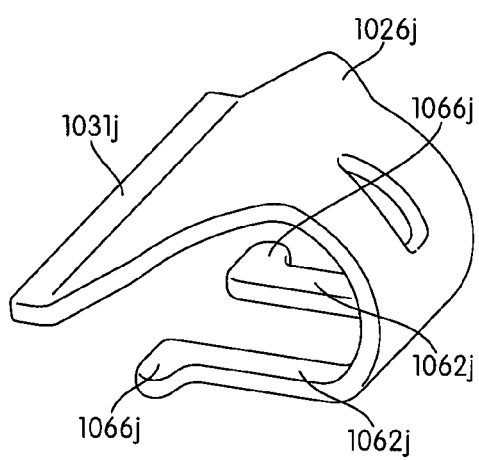
FIG. 10D is a rear perspective view of the locking clip from the embodiment shown in FIG. 100.

FIGS. 10C-10D provide self-ligating bracket 1010j, which may include a modified locking arrangement having a locking clip 1026j and a lingual cavity 1068j having a mesially and distally located locking grooves/ratchets to facilitate and securely lock the lingual free end of the locking clip in both the opened and closed positions. In this specific embodiment, the locking clip 1026j includes a Y-shaped/U-shaped lingual free end 1028j having deformable fingers 1062j. The deformable fingers 1062i may include outwardly extending flange portions 1066j that are configured to actively engage open position grooves 1094j (to aid in maintaining the bracket in the open position) or closed position grooves 1096j (to aid in maintaining the bracket in the closed position) of the mesial and distal side walls 1072j of the lingual cavity 1068j.

In use, the deformable fingers compress inwards towards one another to reduce the overall width of the lingual free end portion 1028j for insertion through the lingual opening. Once the lingual free end portion extends past a first pair of engagement ribs 1100j, the deformable fingers attempt to return to a non-stress position while the flange portions 1066j are received in the pair of open position grooves 1094j and will remain while the bracket is in the open position. To achieve the closed position, the locking clip 1026j is further inserted (gingivally) into the lingual cavity 1068j, where the flange portions 1066j are again deflected inward upon contacting a second pair of engagement ribs 1102j until the flange portions 1066j are received into the pair of closed position grooves 1096j so that the bracket 1010j is substantially maintained in the closed position. To return the bracket to the open position, the locking clip 1026j is moved occlusally towards the second pair of engagement ribs 1102j until the flange portions 1066j are received into the open position grooves 1094i. Active engagement (e.g., flange portions in compression (stressed position) so that an outward force on the sidewalls 1072j is provided) on the deformable fingers 1062j (e.g., flange portions 1066j) and the stabilizing member 1098j (closed position grooves) aid in suppressing movement (e.g., twisting, mesial-distal movement, and/or otherwise) of the locking clip 1026j while in the closed position.

Figure 3A:
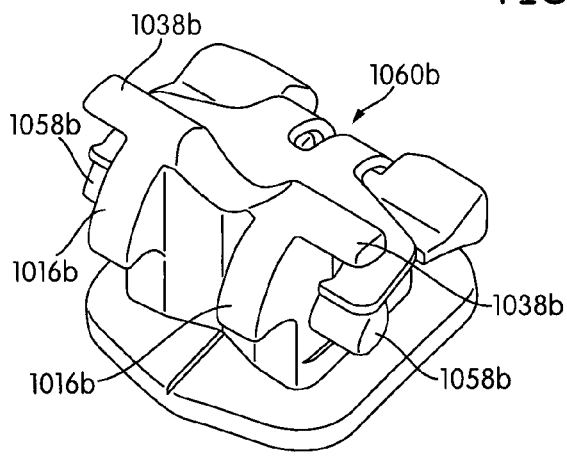
FIG. 3A is a top perspective view of a third embodiment of the present invention.
Figure 3B:
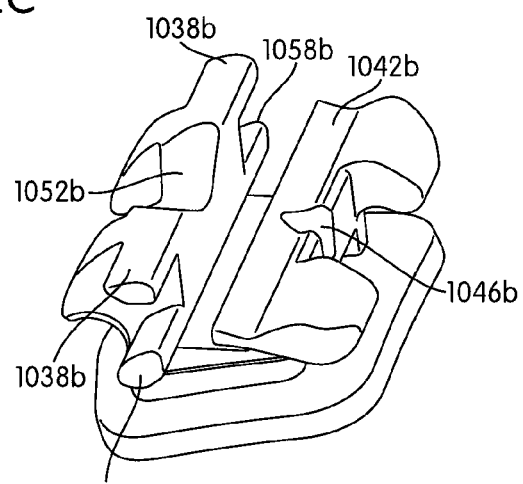
FIG. 3B is another top perspective view of the embodiment shown in FIG. 3A without a locking clip.
Figure 3C:
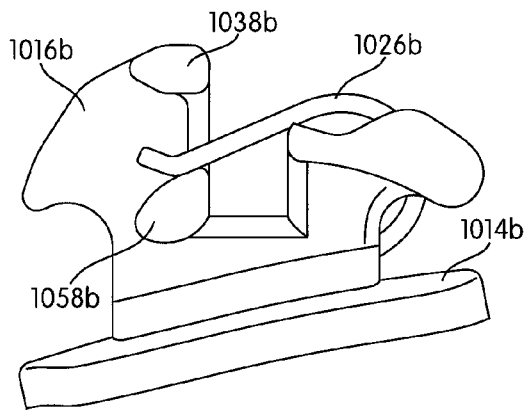
FIG. 3C is a side view of the embodiment shown in FIG. 3A.
Figure 3D:
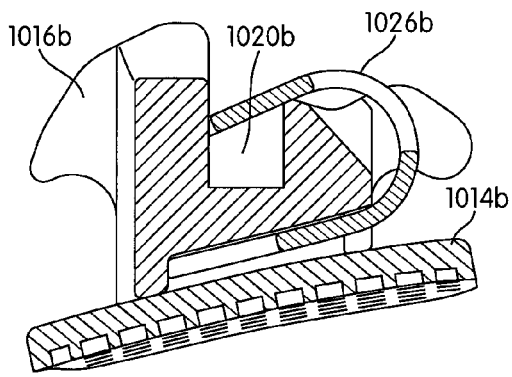
FIG. 3D is a cross-section view of the embodiment shown in FIG. 3C.
Figure 3E:
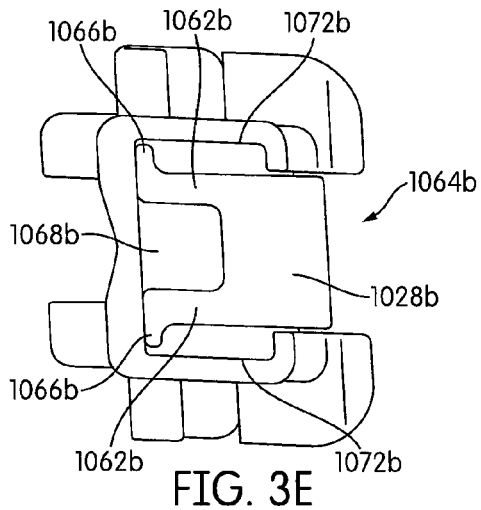
FIG. 3E is bottom view of the embodiment shown in FIG. 3A without a base portion.
Figure 4A:
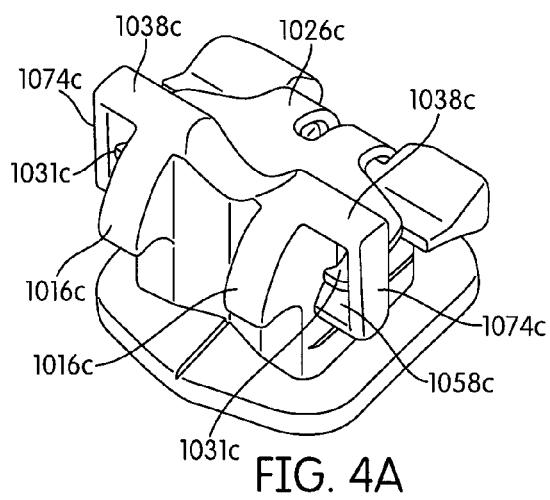
FIG. 4A is a top perspective view of a fourth embodiment of the present invention.
Figure 4B:
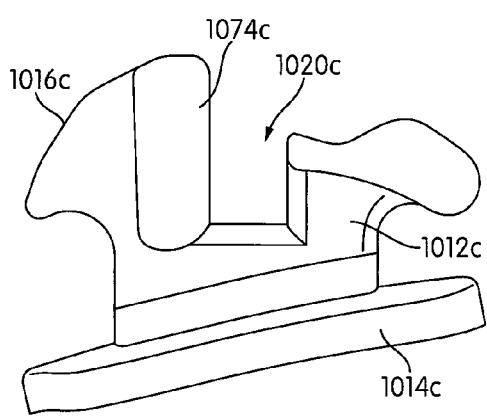
FIG. 4B is a side view of the embodiment shown in FIG. 4A.
Figure 4C:
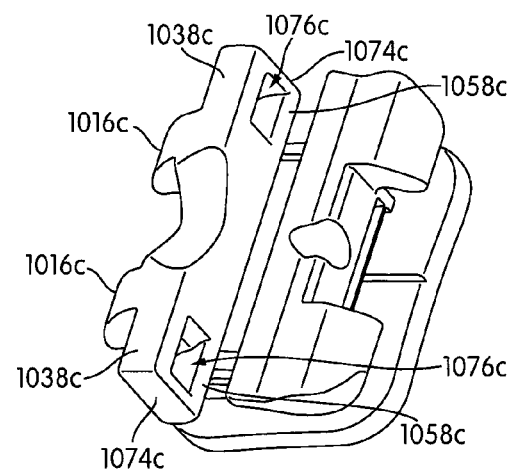
FIG. 4C is another top perspective view of the embodiment shown in FIG. 4A without a locking clip.
Figure 4D:
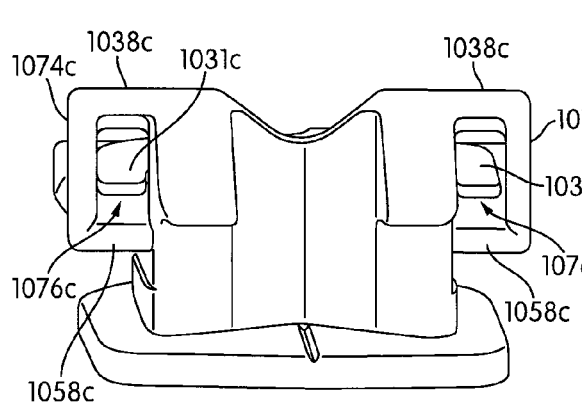
FIG. 4D is a front view of the embodiment shown in FIG. 4A.
Figure 11A:
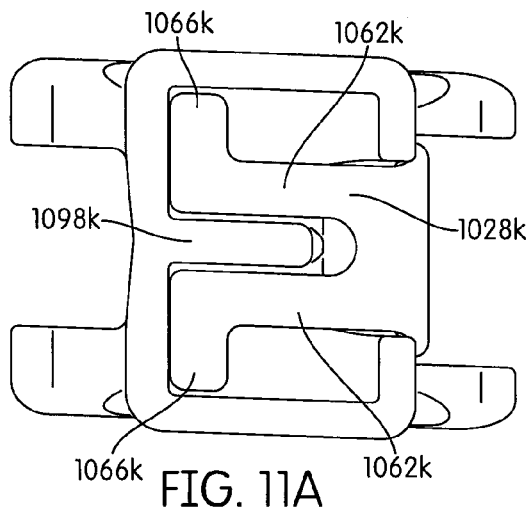
FIG. 11A is a bottom view of an eleventh embodiment of the present invention.
Figure 11B:
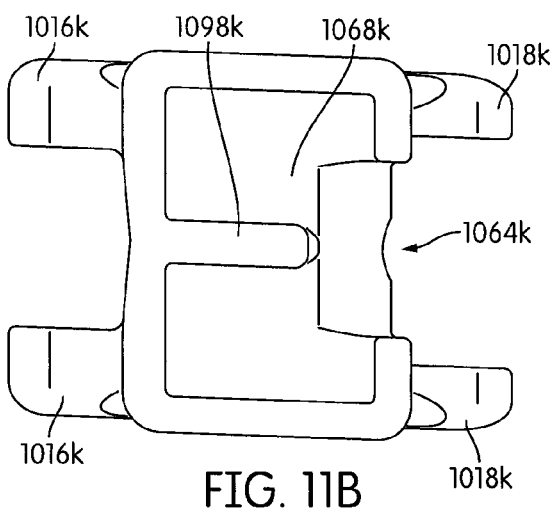
FIG. 11B is another bottom view of the embodiment shown in FIG. 11A without a locking clip.
Figure 11C:
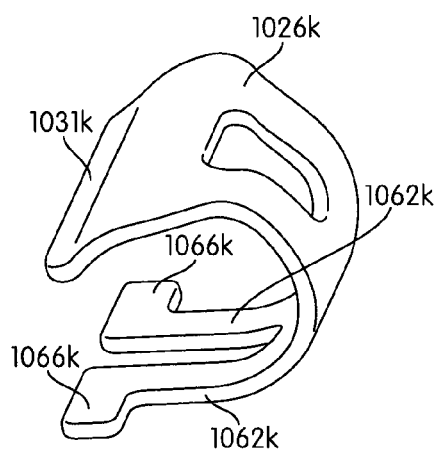
FIG. 11C is a rear perspective view of the locking clip from the embodiment shown in FIG. 11A.

FIGS. 11A-11B are various views of another alternate embodiment of the self-ligating bracket shown in FIG. 3E in which the lingual cavity 1068k further includes a stabilizing member 1098k extending from a gingival side wall 1073k in generally a central location. In this specific embodiment, the width of the stabilizing member 1098k and the width of the spacing between the deformable fingers 1062k may be configured to correspond (e.g., fit and/or active engage) with one another to aid in suppressing movement (e.g., twisting, mesial-distal movement, and/or otherwise) of the locking clip 1026*k* while in the closed position.

As shown in FIGS. 11A-11B, the lingual cavity 1068*k* may further include a chamfered portion (e.g., recess) 1099*k* to guide the lingual free end portion 1028*k* of the locking clip 1026*k* and aid in expanding the locking clip 1026 during the transition from the open position to the closed position. Furthermore, the chamfered portion 1099*k* may be configured to provide clearance for the curved portion 1032*k* of the locking clip 1026*k* while in the closed position.

Figure 12A:
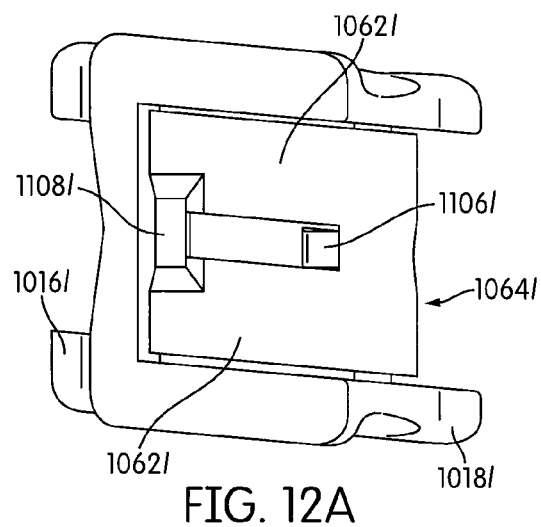
FIG. 12A is a bottom view of a twelfth embodiment of the present invention.
Figure 12B:
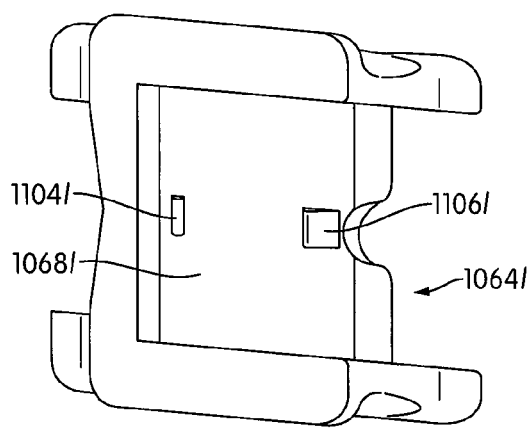
FIG. 12B is another bottom view of the embodiment shown in FIG. 12A without a locking clip.
Figure 12C:
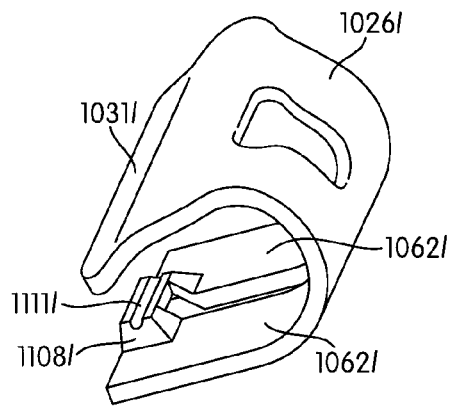
FIG. 12C is a rear perspective view of the locking clip from the embodiment shown in FIG. 12A.

FIGS. 12A-12C are various views of another alternate embodiment of the self-ligating bracket shown in FIG. 3E in which the lingual cavity 1068*l* may further include a rib 1104*l* and a wedge portion 1106*l* to actively engage a locking clip 1026*k* having a bridge portion 1108*l*. The bridge portion 1108*l* interconnecting the deformable fingers 1062*l* at a gingival portion of the lingual free end 1028*l* of the locking clip 1026*l*. The rib portion 1104*l* being spacedly positioned from the gingival side wall 1073*l* and configured to engage the bridge portion 1108*l* having a corresponding mesial-distal groove 1111*l* for a positive lock to substantially maintain the locking clip in the closed position. The wedge portion being occlusally positioned within the cavity at a central location and configured to substantially prevent the locking clip 1026*l* from being removed from the lingual cavity 1068*l*. In this specific embodiment, the positive lock of the bridge portion with the rib and/or the fit of the wedge 1106*l* within the corresponding spacing between the deformable fingers 1062*l* are configured to aid in suppressing movement (e.g., twisting, mesial-distal movement, and/or otherwise) of the locking clip 1026*l* while in the closed position. Furthermore, the width of the neck portion 1029*l* may correspond (e.g., fit to) the mesial distal width of the lingual cavity 1068*l* (and the lingual opening 1064*l*) to further aid in suppressing movement (e.g., twisting, mesial-distal movement, and/or otherwise) of the locking clip 1026*l* while in the closed position.

Figure 13A:
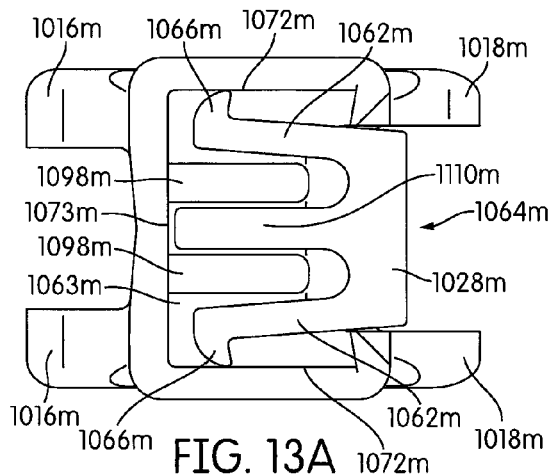
FIG. 13A is a bottom view of a thirteenth embodiment of the present invention.
Figure 13B:
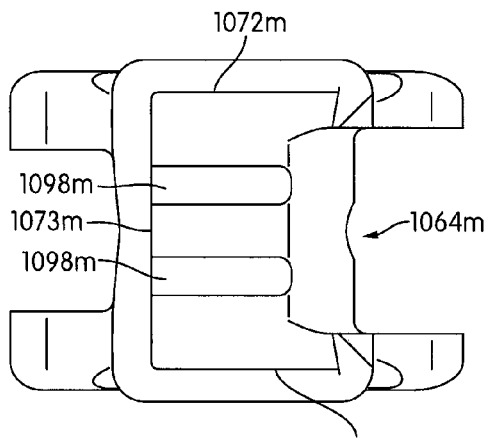
FIG. 13B is another bottom view of the embodiment shown in FIG. 13A without a locking clip.
Figure 13C:
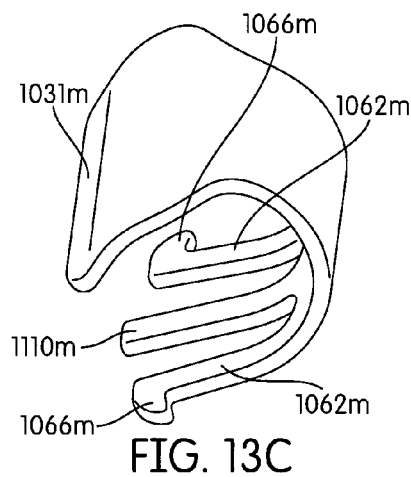
FIG. 13C is a rear perspective view of the locking clip from the embodiment shown in FIG. 13A.

FIGS. 13A-13C are various views of another alternate embodiment of the self-ligating bracket shown in FIG. 11A in which the lingual cavity 1068*m* may further include a plurality of mesially-distally spaced apart stabilizing members 1098*m* extending from a gingival side wall 1073*m* in generally a centralized location with the lingual cavity 1068*m*. In this specific embodiment, the locking clip 1026*m* may further include a stabilizing finger 1110*m* extending from the lingual free end 1028*m* and intermediate of the deformable fingers 1062*m*. The width of the stabilizing finger 1110*m* and the width of the spacing between the stabilizing members 1098*m* are configured to correspond (e.g., fit and/or actively engage) with one another to aid in suppressing movement (e.g., twisting, mesial-distal movement, and/or otherwise) of the locking clip 1026*m* while in the closed position. Optionally, the mesial-distal width of the lingual free end 1028*m* (e.g., generally taken across the flange portions 1066*m*) is configured to be wider (in a non-stressed state) than the mesial-distal width of the lingual cavity 1068*m* so that upon insertion within the lingual cavity 1068*m* the flange portions 1066*m* may exert an outward force (e.g., in a stressed state) on the respective mesial and distal side walls 1072*m* to aid in suppressing movement (e.g., twisting, mesial-distal movement, and/or otherwise) of the locking clip 1026*m* while in the closed position.

Figure 14A:
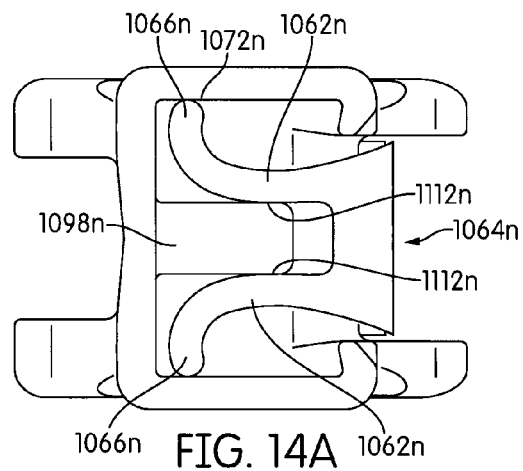
FIG. 14A is a bottom view of a fourteenth embodiment of the present invention.
Figure 14B:
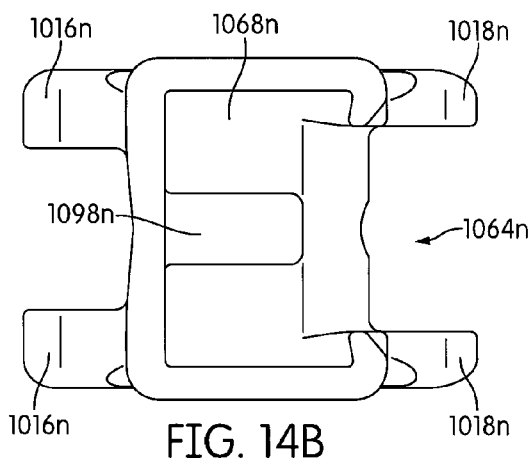
FIG. 14B is another bottom view of the embodiment shown in FIG. 14A without a locking clip.
Figure 14C:
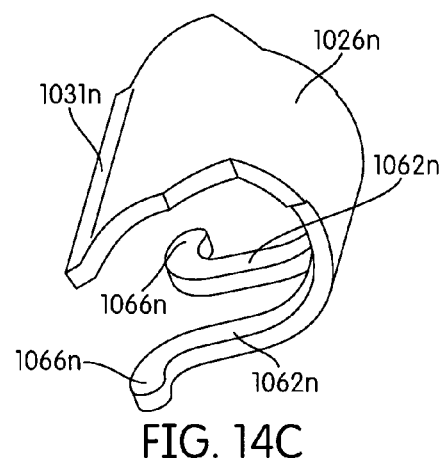
FIG. 14C is a rear perspective view of the locking clip from the embodiment shown in FIG. 14A.

FIGS. 14A-14C are various views of another alternate embodiment of the self-ligating bracket shown in FIG. 13A in which the lingual cavity 1068*n* further includes a single stabilizing member 1098*n* extending from a gingival side wall 1073*n* in generally a central location. In this specific embodiment, the mesial-distal width of the lingual free end 1028*n* (e.g., generally taken across the flange portions 1066*n*) may be configured to be wider (in a non-stressed state) than the mesial-distal width of the lingual cavity 1068*m* (e.g., from mesial side wall to distal side wall) so that upon insertion within the lingual cavity 1068*n* the flange portions 1066*n* may exert an outward force (e.g., in a stressed state) on the respective mesial and distal side walls 1072*n* to aid in suppressing movement (e.g., twisting, mesial-distal movement, and/or otherwise) of the locking clip 1026*n* while in the closed position. Furthermore, the locking mechanism may further include a wider stabilizing member 1098*n* of the lingual cavity 1068*n*, an increased lingual free end portion 1028*n* mesial-distal width to lingual cavity 1068 mesial-distal width ratio, or both so that an additional force may be provided by an intermediate portion 1112*n* of the deformable fingers 1062*n* on the stabilizing member 1098*n* to further aid in suppressing movement (e.g., twisting, mesial-distal movement, and/or otherwise) of the locking clip 1026*n* while in the closed position.

Figure 15A:
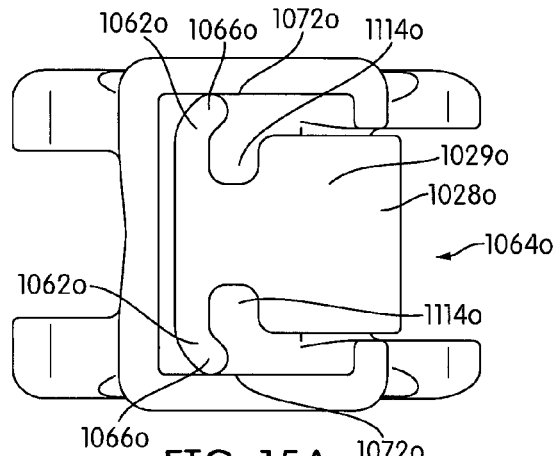
FIG. 15A is a bottom view of a fifteenth embodiment of the present invention.
Figure 15B:
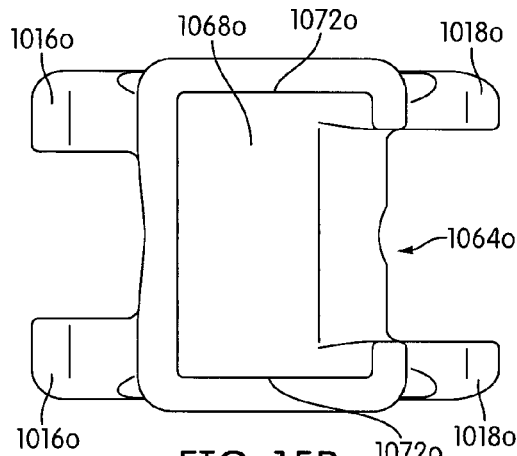
FIG. 15B is another bottom view of the embodiment shown in FIG. 15A without a locking clip.
Figure 15C:
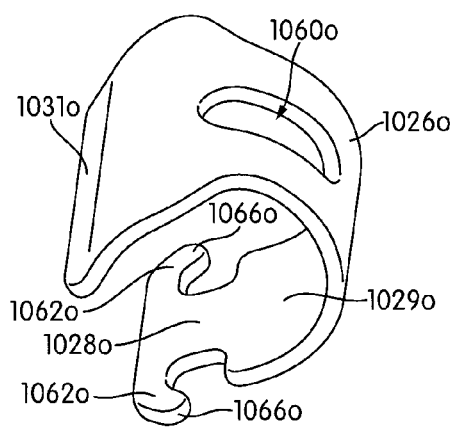
FIG. 15C is a rear perspective view of the locking clip from the embodiment shown in FIG. 15A.

FIGS. 15A-15C are various views of another alternate embodiment of the self-ligating bracket shown in FIG. 3E in which the lingual free end 1028*o* of the locking clip 1026*o* may further include a neck portion 1029*o* and intermediate grooves 1114*o* to aid in the deformation of the deformable fingers 1062. In this specific embodiment, the mesial-distal width of the lingual free end portion 1028*o* (e.g., generally taken across the flange portions 1066*o*) may be configured to be wider (in a non-stressed state) than the mesial-distal width of the lingual cavity 1068*o* (e.g., from mesial side wall to distal side wall) so that upon insertion within the lingual cavity 1068*o* the flange portions 1066*o* may exert an outward force (e.g., in a stressed state) on the respective mesial and distal side walls 1072*o* to aid in suppressing movement (e.g., twisting, mesial-distal movement, and/or otherwise) of the locking clip 1026*o* while in the closed position. Furthermore, the neck portion 1029*o* may extend into the lingual cavity (while in the closed position) and may be sized corresponding to the width of the lingual opening 1064*o* to aid in guiding the locking clip 1026*o* during transition between the open and closed positions.

Figure 16A:
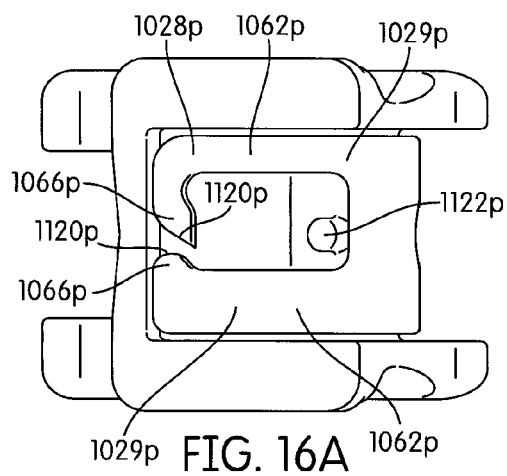
FIG. 16A is a bottom view of a sixteenth embodiment of the present invention.
Figure 16B:
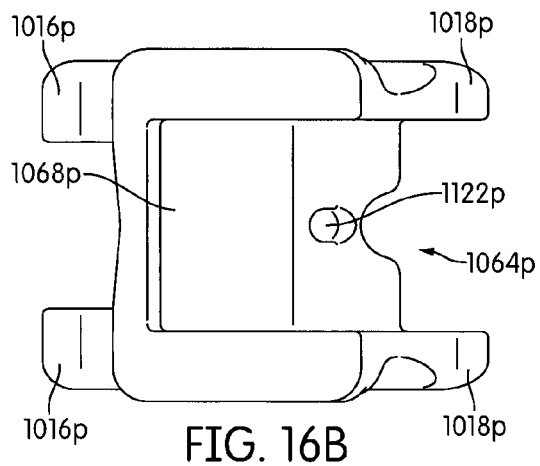
FIG. 16B is another bottom view of the embodiment shown in FIG. 16A without a locking clip.
Figure 16C:
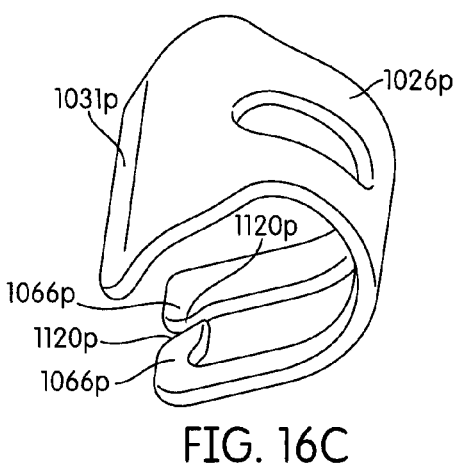
FIG. 16C is a rear perspective view of the locking clip from the embodiment shown in FIG. 16A.

FIGS. 16A-16C are various views of another alternate embodiment of the self-ligating bracket shown in FIG. 3E in which wider mesial and distal side walls 1072*p* may be provided so as to be generally flush mesial and distal edges 1116*p* of the lingual opening 1064*p* (occlusal side of body) thereby resulting in a reduced lingual cavity 1068*p*. Furthermore, the locking clip 1026*p* may further include a U-shaped lingual free end 1028*p* having deformable fingers 1062*p* with inward facing flange portions 1066*p* forming a gingival opening 1118*p* therebetween. The flange portions 1066*p* may include opposing edges 1120*p* having angled, curved, and/or otherwise portions to aid in securing the locking clip 1026*p* to the bracket body 1012*p*. More particularly, during installation of the locking clip 1026*p* the lingual free end 1028*p* is inserted gingivally into the occlusal side of the lingual opening 1064*p* where the opposing edges 1120*p* of the flange portions 1066*p* are brought into contact with an occlusal protrusion 1122*p* of the lingual cavity 1068*p*. The deformable fingers 1062*p* may be deformed outward thereby increasing the width of the gingival opening 1118*p* to allow for passage of the occlusal protrusion 1122*p* through the gingival opening 1118*p*. In doing so, the lingual free end 1028*p* is allowed to be further inserted into the lingual cavity for securement of the locking clip to the body 1012*p*. The gingival opening 1118*p* may be configured so that the gingival side of the gingival opening 1118*p* allows for passage of the occlusal protrusion 1122*p* during installment of the locking clip while the occlusal side of the gingival opening substantially preventing passage of the occlusal protrusion 1122*p* so that the locking clip may remain secured to the body 1012*p*. Desirably, the neck portion 1029*p* may extend into the lingual cavity (while in the closed position) and may be sized corresponding to the width of the lingual opening 1064*p* to aid in guiding the locking clip 1026*p* during transition between the open and closed positions. Desirably, the width of the neck portion 1029*p* (e.g., from distal edge of distal deformable finger to the mesial edge of the mesial deformable finger) may correspond (e.g., fit to) the mesial distal width of the lingual cavity 1068*p* (and the lingual opening 1064*p*) to further aid in guiding the locking clip between the open and closed positions and/or suppressing movement (e.g., twisting, mesial-distal movement, and/or otherwise) of the locking clip 1026*p* while in the closed position.

In yet another embodiment of the present invention, a self-ligating orthodontic bracket is shown in FIGS. 17A-17I, and is generally indicated to by reference numeral 610. As can be seen, the orthodontic bracket 610 includes a body 612, a lingual mounting base 614 attached to the body, and a locking mechanism having a locking clip 626 and a retaining member 627. The body 612 may include a pair of laterally spaced gingival tie wings 616 and a pair of laterally spaced occlusal tie wings 618 extending from the labial surface of the body 612. The gingival tie wings 616 and the occlusal tie wings 618 generally curve lingually. An archwire slot 620 extends mesio-distally across the body 612 and between the gingival and occlusal tie wings 616 and 618. The archwire slot 620 opens labially to receive an archwire 622.

A first bridge portion 660 and a second bridge portion 661 are provided in an interwing region 624, with the first bridge portion 660 spanning between the gingival tie wings 616 and the second bridge portion 661 spanning between the occlusal tie wings 618. It is appreciated that the first and second bridge portions 660 and 661 extend from labial surface of the archwire slot (and defining portions thereof) up to the labial surfaces of the respective tie wings 616 and 618.

The retaining member 627 may includes a first pair of stops 644 and a second pair of stops 646 on the gingival tie wings 616 to inhibit inadvertent movement of the locking clip 626 from a closed position (e.g., an active first closed position in stops 644 or a second closed position in stops 646) to an open position and optionally to maintain the locking clip 626 open when it is pivoted to the open position. Each stop defining a first opening, at least one guide portion, and at least one flange. The first pair of stops 644 extend generally outward from the respective gingival tie wings 616 and include a first opening 664, a first guide portion 674, and a first flange 668 for engagement with the locking clip 626 to maintain the first closed position (e.g., active bracket for active first closed position). Similarly, the second pair of stops 646 extend generally outward from the respective gingival tie wings 616 and include a second opening 666, a guide portion 675, and a second flange 669 for engagement with the locking clip 626 to maintain the second closed position (e.g., passive bracket for passive second closed position). It is appreciated that the first and second pairs of stops 644 and 646 may positioned so that one stop of each pair of stops 644 and 646 is gingivally-occlusally juxtaposed to the respective other stop of each pair of stops 644 and 646. Desirably, the pairs of stops on each gingival tie may define a generally W-shaped configuration. It is further appreciated that the pairs of stops may be located elsewhere, for example along the respective internal surface of the gingival tie wings 616 about the interwing region 624.

The locking clip 626 is pivotally mounted on the occlusal tie wings 618 and is moveable between two closed positions (FIGS. 34-37) where access to the archwire slot 620 is inhibited and an open position (FIG. 31-33) where access to the archwire slot 620 is permitted. It is appreciated that the locking clip 626 is in the form of spring element having a generally Y-shaped configuration. More particularly, the locking clip 626 may include a head portion 628, with a pair of opposing side arms 650 and 652, which define an opening 629 therebetween. It is appreciated that the head portion 628 and/or the side arms 650 and 652 are configured to extend across the archwire slot 620.

The arms 650 and 652 may include free ends (e.g., extending generally mesial and distal, though not required) that are in-turned to define oppositely directed spaced apart hook ends 672. The (gingival) hook ends 672 may be received in the respective first openings 664 or the respective second openings 666, which are formed in the gingival tie wings 616.

The locking clip 626 may also include a connecting the head 628 and a base portion 692 having opposed free ends (e.g., extending generally mesial and distal, though not required) that are out-turned to define oppositely directed spaced apart tail ends 632 and 634 respectively. Each of the tail ends 632 and 634 is received in a respective bore 636 and 638 formed in one of the occlusal tie wings 618. The bores 636 and 638 may extend (e.g., mesial-distally) completely through the respective tie wings 618 or partially therethrough.

To close the orthodontic bracket 610 in the first closed position, the locking clip 626 is pivoted about the tails 632 and 634 towards the first pair of stops 644 (e.g., gingival first pair of stops) of the locking mechanism 627 about the gingival tie wings 616. The hook ends 672 (e.g., 672*a* and 672*b*) make contact with and are gingivally guided along the respective labial surface of the first guide portions 674. The hook ends 672 are continually guided along the labial surfaces of the first guide portions 674 until the hook ends 672 extend beyond the flanges 668 of the first pair of stops 644. This allows the locking clip 626 to snap back towards its non-stressed state so that the hooks 672 engage the respective flanges 668 thereby maintaining the locking clip 626 in the first closed position. In doing so, the locking clip 626 is deflected lingually so that contact between the locking clip, the archwire, and the archwire slot may be substantially or completely maintained while in the first closed position (FIGS. 36A, 36B, and 37).

More particularly, the reaction force applied to the labial surface of the first guide portions 674 by the hook ends 672 causes the locking clip 676 to deflect (e.g., gingivally-lingually) into a stressed-state. When the hook ends 672 are pivoted beyond the respective first stops 644 and generally lingually into the first openings 664, the locking clip 626 snaps back towards the first flanges 668 in an attempt to return to its non-stressed state. In doing so, the first flanges 668 of the first pair of stops 644 prevent removal of the respective hook ends 672 from the first opening 664 during its first closed position. The first flanges 668 inhibit the locking clip 626 while in this stressed condition from moving back towards the open position. In this way, the archwire slot 620 remains closed thereby actively securing the archwire 622a in the archwire slot.

To close the orthodontic bracket 610 in the second closed position, the locking clip 626 is pivoted about the tails 632 and 634 towards the second pair of stops 646 of the locking mechanism 627 about the gingival tie wings 616. The hook ends 672 make contact with and are gingivally guided along the respective labial surface of the second guide portions 675. The hook ends 672 are continually guided along the labial surfaces of the second guide portions 675 until the hook ends 672 extend beyond (e.g., gingivally-lingually) the first flanges 669 of the second pair of stops 646. This allows the locking clip 626 to snap back towards its non-stressed state so that the hook ends 672 engage the respective second flanges 669 thereby maintaining the locking clip 626 in the second closed position. In doing so, the locking clip 626 may be slightly deflected lingually so that minimal or no contact between the locking clip 626 and the archwire may be maintained while in the second closed position (FIGS. 34A, 34B, and 35).

More particularly, the reaction force applied to the labial surface of the second guide portions 675 by the hook ends 672 causes the locking clip 676 to deflect (e.g., gingivally-lingually) into a stressed-state. When the hook ends 672 are pivoted beyond the respective second stops 646 and generally lingually into the second openings 666, the locking clip 626 snaps back towards the second flanges 669 in an attempt to return to its non-stressed state. In doing so, the second flanges 669 prevent removal of the respective hook ends 672 from the second openings 666 during its second closed position. As such, the second flanges 669 inhibit the locking clip 626 while in this stressed condition from moving back towards the open position. In this way, the archwire slot 620 remains closed thereby passively securing the archwire 622b in the archwire slot.

To release the archwire, the locking clip 626 are pushed gingivally-lingually to disengage the hook ends 672 from the respective first or second pairs of stops 644 and 646. In one specific example to release the archwire from the first closed position, the hooks ends 672 are first moved gingivally-lingually (typically along the labial surface of a third guide portion 676) beyond the first flanges 668. In another specific example to release the archwire from the second closed position, the hooks ends 672 are first moved gingivally-lingually (typically along the labial surface of a first guide portion 674) beyond the second flanges 669. Thereafter, the locking clip 626 may be removed from either of the respective first and second pairs of stops 644 and 646 so that the locking clip 626 (in its non-stressed state) is free to pivot about the tails 632 and 634

In one specific example, it is contemplated that as the locking clip 626 is moved (e.g., directed or pushed gingivally) along the first guide 674, the locking clip 626 disengages from the second pair of stops 646. Once the locking clip 626 is moved beyond the first pair of stops 644, the hook ends 672 bias lingually-occlusally into the first opening 664 thereby transitioning the locking clip from the second closed position to the first closed position.

Optionally, the bracket 610 may further include a groove 680 for receiving an optional ligature. When included, the groove 680 may be positioned between the along the exterior of the tie wings 616. It is appreciated that the groove 680 may be configured to aid in releasing the locking clip 626 from the second closed position and/or the first closed position by providing access to the arms of the locking clip 626. For example, while the locking clip 626 is being moved (e.g., directed or pushed gingivally) from the first closed position along the third guide 676, the hook ends 672 will be directed lingually and under the lingual free ends of the tie wings into the groove 680 such that the spring-tension of the locking clip will automatically move (e.g., labially direct) the locking clip 626 through the groove 680 to the open position.

Figure 17A:
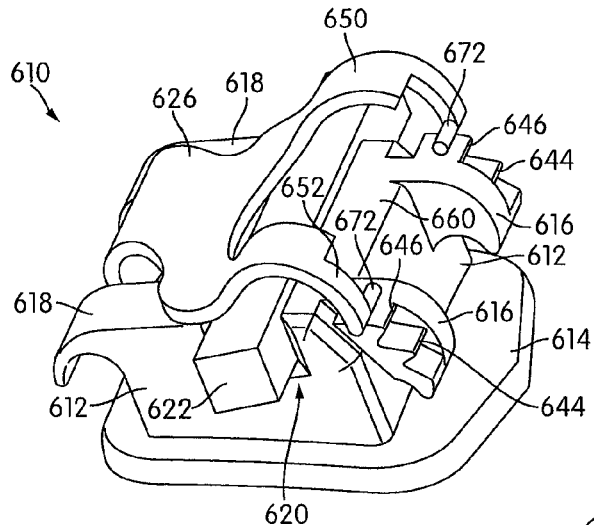
FIG. 17A is a top perspective view of a seventeenth embodiment of the present invention.
Figure 17B:
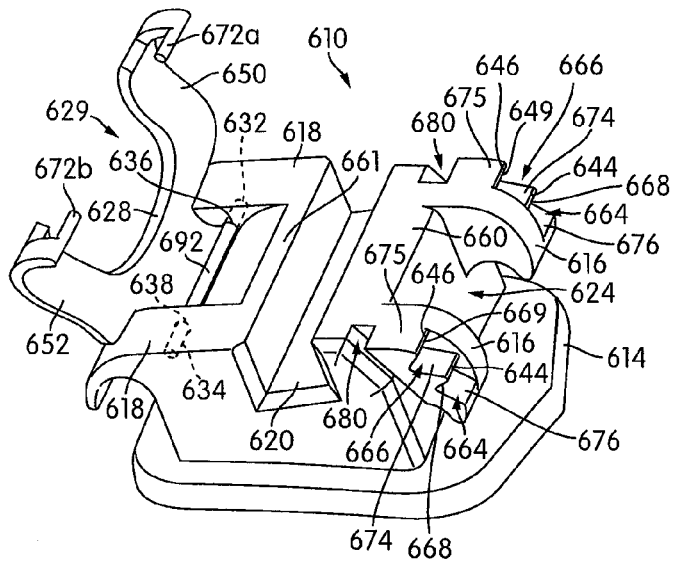
FIG. 17B is another top perspective view of the embodiment shown in FIG. 17A in an open position.
Figure 17C:
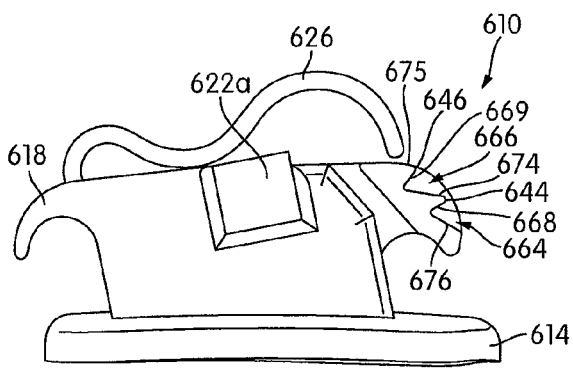
FIG. 17C is a side view of the embodiment shown in FIG. 17A.
Figure 17D:
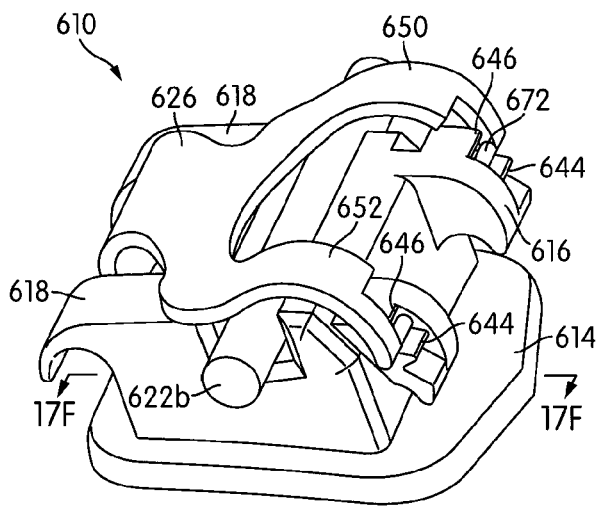
FIG. 17D is another top perspective view of the embodiment shown in FIG. 17A in a first closed position.
Figure 17E:
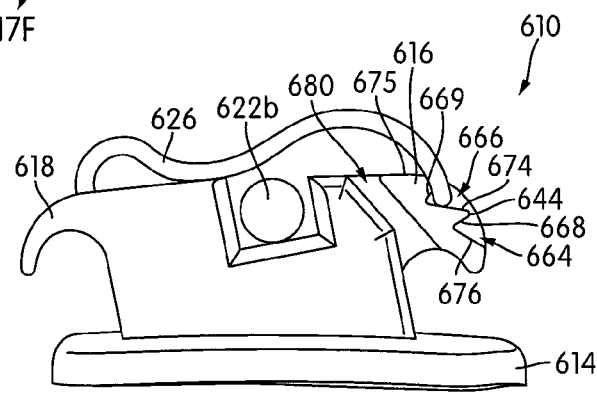
FIG. 17E is a side view of the embodiment shown in FIG. 17D.
Figure 17F:
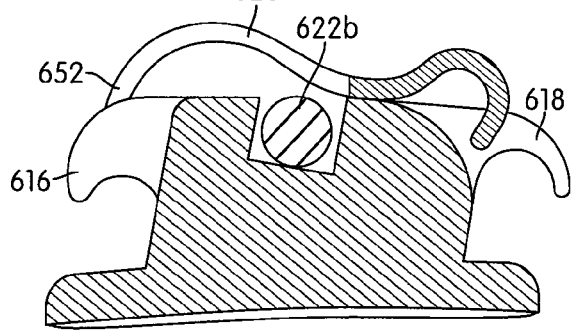
FIG. 17F is a cross-section view of the embodiment shown in FIG. 17E.
Figure 17G:
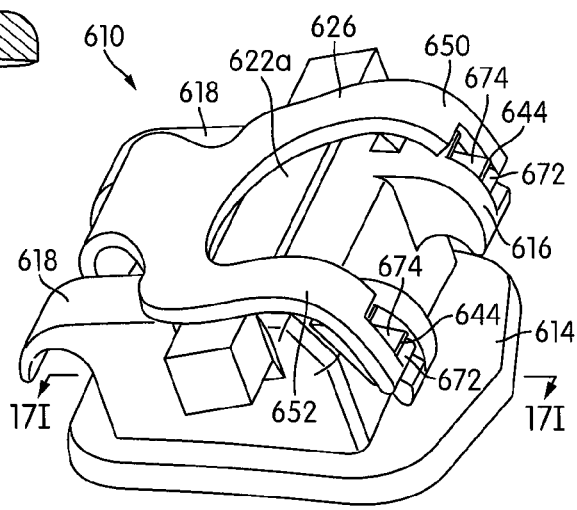
FIG. 17G is another top perspective view of the embodiment shown in FIG. 17A in a second closed position.
Figure 17H:
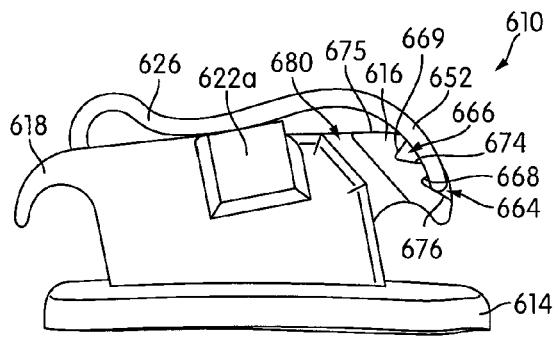
FIG. 17H is a side view of the embodiment shown in FIG. 17G.
Figure 17I:
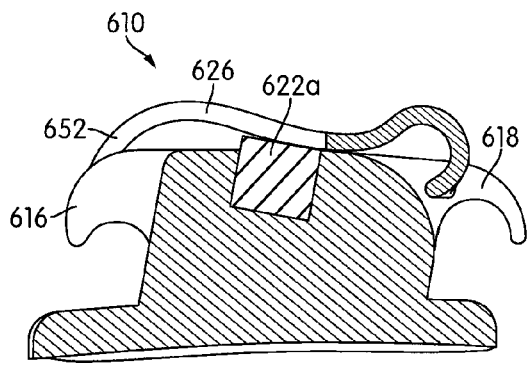
FIG. 17I is a cross-section view of the embodiment shown in FIG. 17H.
Figure 17J:
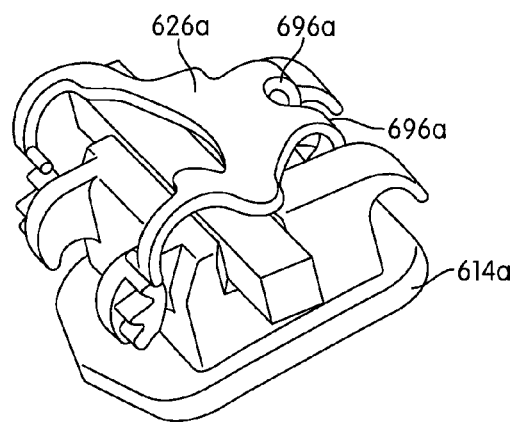
FIG. 17J is another perspective view of the embodiment shown in FIG. 17A.
Figure 17K:
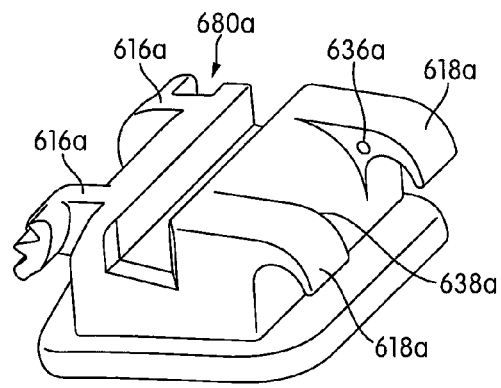
FIG. 17K is another bottom view of the embodiment shown in FIG. 17A without a locking clip.
Figure 17L:
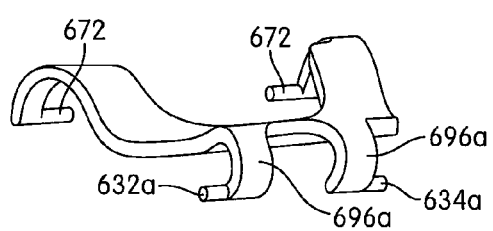
FIG. 17L is a rear perspective view of the locking clip from the embodiment shown in FIG. 17A.
Figure 18A:
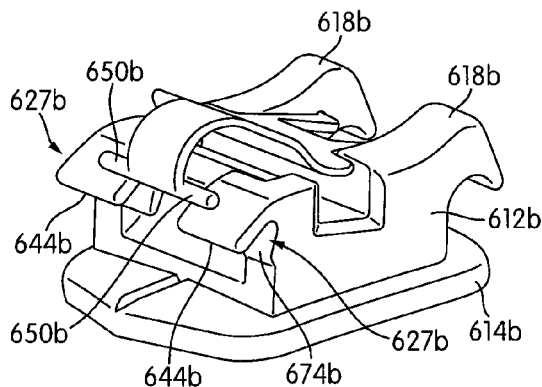
FIG. 18A is a top perspective view of an eightieth embodiment of the present invention.
Figure 18B:
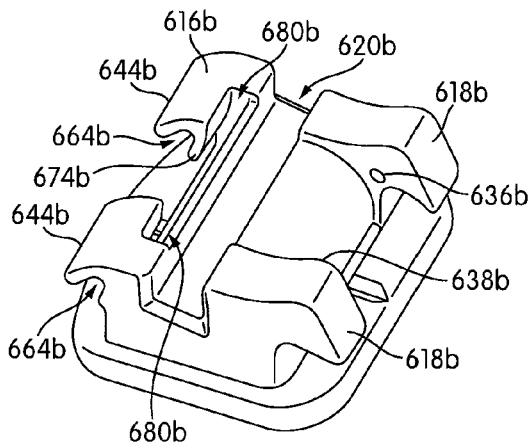
FIG. 18B is another top perspective view of the embodiment shown in FIG. 18A without a locking clip.
Figure 18C:
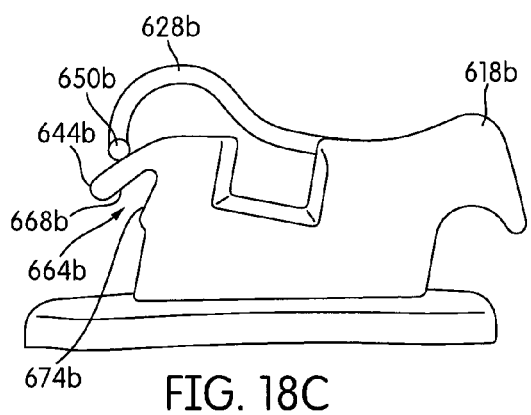
FIG. 18C is a side view of the embodiment shown in FIG. 18A.
Figure 18D:
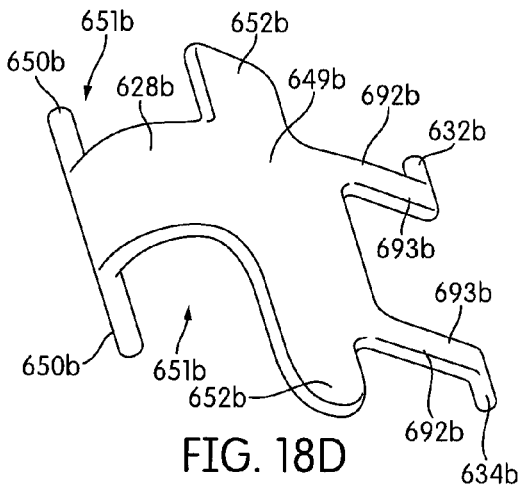
FIG. 18D is a rear perspective view of the locking clip from the embodiment shown in FIG. 18A.

FIGS. 17J-17L are various views of another alternate embodiment of the self-ligating bracket shown in FIGS. 17A-17I in which the occlusal portion of the locking clip 626a includes a pair of lingually curved arms 696a for pivotal engagement with the bores 636a and 638a. The arms 696a being spaced apart to define a generally Y-shaped occlusal portion of the locking clip 626a.

Self-ligating brackets having a ratchet design may include a single ratchet or a plurality of ratchets that may be attached to the tie wing (e.g. gingival tie wing or wings) of the bracket body. The ratchets may be an integral part of gingival tie-wings (outside or inside), or may be attached permanently to Tie-wings by appropriate manufacturing method, or can be attached to any other (appropriate) location on the body. The ratchet design may have multiple slots to lock the top legs of clip (at a labial portion of the archwire clip and preferably at a labial free end of the clip) when closed.

It is believed that this engagement design may be configured such that the clip may be opened and/or closed simply pushing the clip with a finger and/or otherwise (e.g., tool). Advantageously, this ratchet based engagement mechanism may be configured such that the need for instrument to open or close the clip may be eliminated as compared to the prior art.

FIGS. 18A-18D are various views of an alternative embodiment of the self-ligating bracket shown in FIG. 17A in which a modified "ratchet" based engagement mechanism may be provided having a locking clip 626b and a retaining member 627b. The body 612b may include a pair of laterally spaced gingival tie wings 616b and a pair of laterally spaced occlusal tie wings 618b extending the body 612b. The gingival tie wings 616b generally curve lingually thereby forming a portion of the retaining member 627b.

The retaining member 627b may include a pair of opposing stops 644b on the gingival tie wings 616b to inhibit inadvertent movement of the locking clip 626b from a closed position to an open position and optionally to maintain the locking clip 626b open when it is pivoted to the open position. The stops 644b may be an integral extension of the respective gingival tie wings 616b curving lingually therefrom to form opening 664bs, guide portions 674b, and flanges 668b for engagement with the locking clip 626b to maintain a closed position. Desirably, the stops 644b on each gingival tie wing may define a generally hook-shaped configuration, though not required.

The locking clip 626b may include a base portion 692b having opposing base arms 693b being pivotally mounted on the occlusal tie wings 618b. The spaced apart base arms 693b may further include oppositely directed tail ends 632b and 634b respectively. Each of the tail ends 632b and 634b is received in a respective bore 636b and 638b formed in one of the occlusal tie wings 618b. In this specific embodiment, the base arms 693b are generally flat.

It is appreciated that the locking clip 626b may be in the form of spring element having a generally T-shaped configuration. More particularly, the locking clip 626b may include a head portion 628b and an intermediate portion 649b that generally covers the arch wire slot 620b while in the closed position. The head portion 628b and the intermediate portion 649b may include a pair of side arms 650b and 652b, respectively, which extend mesially and distally from the head portion 628b and intermediate portion 649b to define recesses 651b therebetween. The arms 650b may be received in the respective openings 664, which are formed in the gingival tie wings 616 to secure the locking clip 626b in the closed position.

Optionally, the bracket 610b may further include grooves 680b for receiving an optional ligature. When included, the groove 680b may be positioned along the exterior of the gingival tie wings 616b. It is appreciated that the groove 680b may be configured to aid in releasing the locking clip 626b (e.g., arms 650b) from the closed position by providing access to the arms 650b of the locking clip 626b. For example, while the locking clip 626b is being moved (e.g., directed or pushed gingivally) from the closed position along the guide 674b, the arms 650b will be directed lingually and under the lingual free ends of the tie wings into the groove 680b such that the spring-tension of the locking clip will automatically move (e.g., labially direct) the locking clip 626b through the groove 680 to the open position.

FIGS. 19A-19E are various views of another alternate embodiment of the self-ligating bracket shown in FIGS. 18A-18D in which the retaining members 627c have been reduced extend inwardly from a portion of the gingival tie wings 616c. In doing so, hook portions of the gingival tie wings 616c may available for receiving optional ligature(s).

Figure 19A:
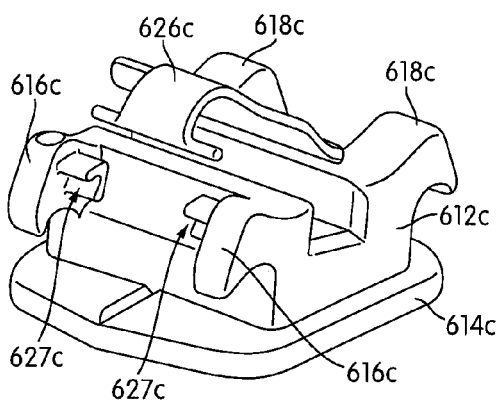
FIG. 19A is a top perspective view of a ninetieth embodiment of the present invention.
Figure 19B:
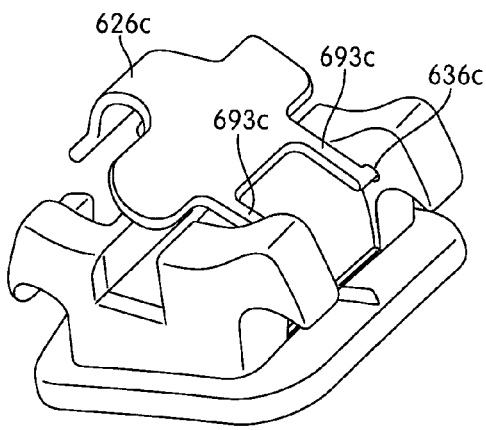
FIG. 19B is another top perspective view of the embodiment shown in FIG. 19A.
Figure 19C:
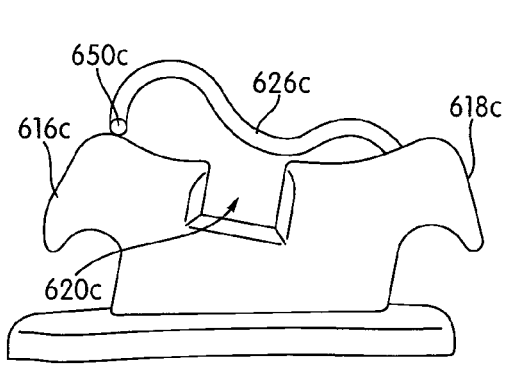
FIG. 19C is a side view of the embodiment shown in FIG. 19A.
Figure 19D:
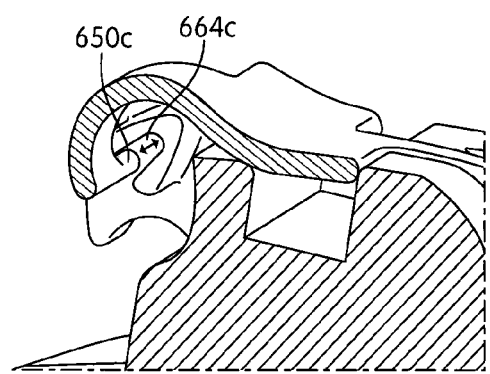
FIG. 19D is a zoomed-in cross-section view of the embodiment shown in FIG. 19C.
Figure 19E:
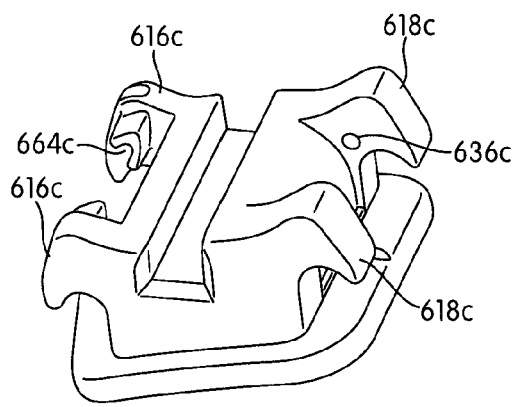
FIG. 19E is another top perspective view of the embodiment shown in FIG. 19A without a locking clip.

The interactivity between the locking clip 626c and archwire 622c in the final active stage may be critical from a clinical perspective. It is believed that variation in the clip design may allow for the interactivity between the clip and archwire. Generally, the interactivity may be defined as clip having some room to move (e.g., "floating" and/or moveable while in the closed position). For example as shown in FIG. 19D, a zoomed in view of a "ratcheting" member is provided, which alone or in combination with an opposing ratcheting member may be configured to achieve this type of interactivity. More particularly, as shown if FIG. 19D, a clearance may be achieved while the labial free end of the clip engages the locking ratcheting slot after the clip is in the closed position.

The middle of clip (e.g., the section of the clip that generally may be in contact with archwire) may be sufficiently flexible to generally maintain a predetermined interactivity. Both geometry change (i.e. less material) and/or softer material of the clip may be optimized to achieve the predetermined interactivity between the middle section of clip and the arch wire (FIG. 19C).

Once the clip is in the final locked position, tensional (spring) force may be generated in the clip. As a result, it is appreciated that when the clip is pushed down (e.g., lingually) further from the final locked position, the tension will pull the tip of the clip (e.g., T-shaped or otherwise shaped post at the labial free end of the clip) so that the clip may be released from the slot (e.g., ginigival ratcheting slot(s)) to the open position.

Figure 20A:
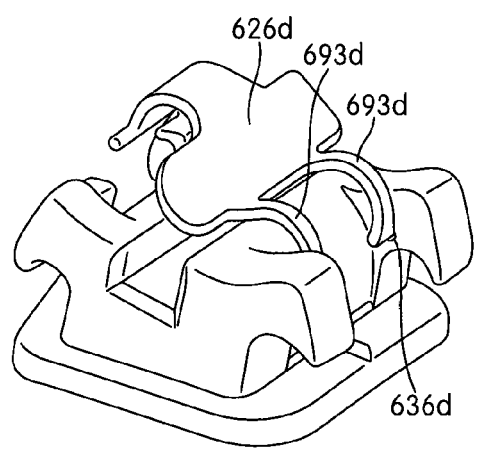
FIG. 20A is a top perspective view of a twentieth embodiment of the present invention.
Figure 20B:
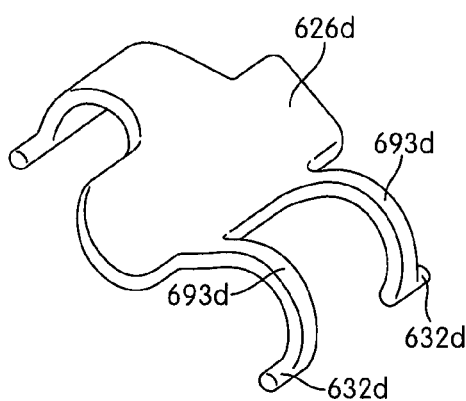
FIG. 20B is a rear perspective view of the locking clip from the embodiment shown in FIG. 20A.

FIGS. 20A-20B are various views of another alternate embodiment of the self-ligating bracket shown in FIGS. 19A-19E in which the base portion 692d of the locking clip 626d may include curved base arms 693d.

Figure 21A:
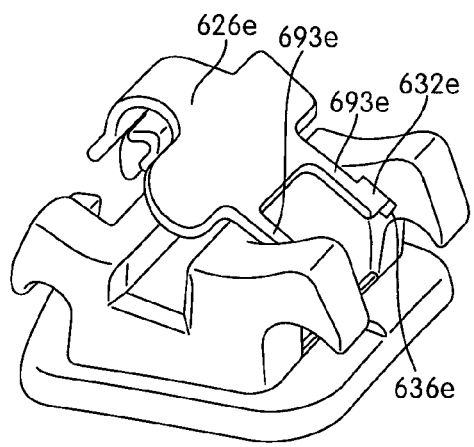
FIG. 21A is a top perspective view of a twenty-first embodiment of the present invention.
Figure 21B:
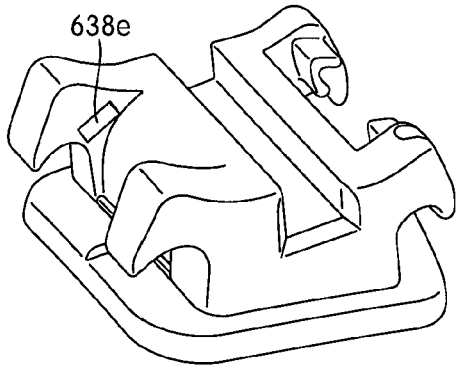
FIG. 21B is another top perspective view of the embodiment shown in FIG. 21A without a locking clip.
Figure 21C:
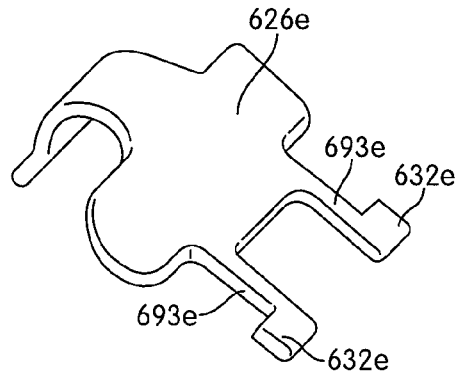
FIG. 21C is a rear perspective view of the locking clip from the embodiment shown in FIG. 21A.

FIGS. 21A-21C are various views of another alternate embodiment of the self-ligating bracket shown in FIGS. 19A-19E in which the tail ends 632e and 634e may be provided as generally rectangular members extending from the base arms 693e. In doing so, the respective bores 636e and 638e have been modified rectangular openings to correspond with the rectangular tail ends 632e and 634e.

Figure 22A:
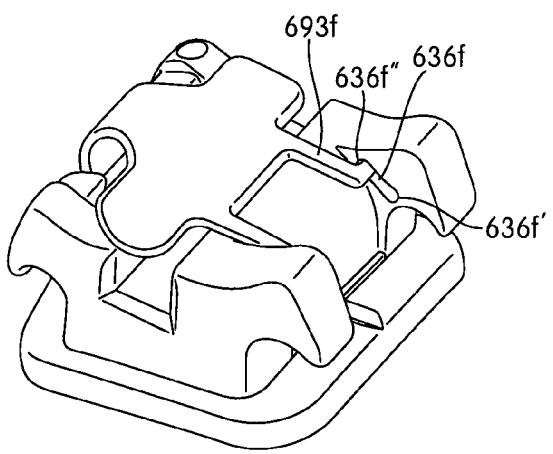
FIG. 22A is a top perspective view of a twenty-second embodiment of the present invention.
Figure 22B:
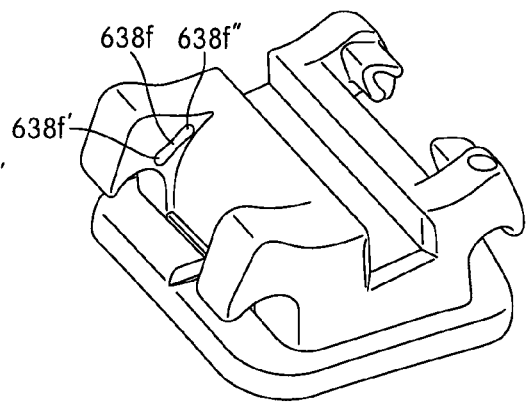
FIG. 22B is another top perspective view of the embodiment shown in FIG. 22A without a locking clip.
Figure 22C:
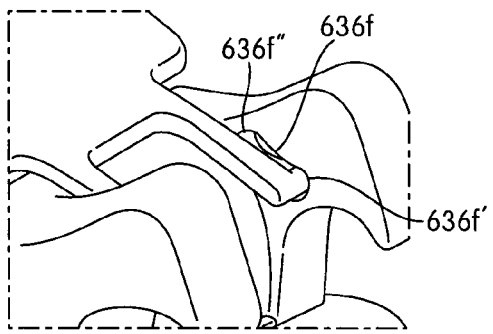
FIG. 22C is a zoomed-in top perspective view of the embodiment shown in FIG. 22A in an open position.
Figure 22D:
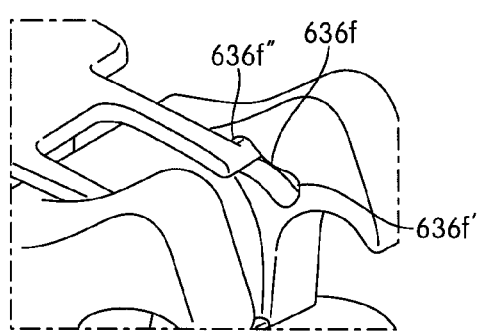
FIG. 22D is a zoomed-in top perspective view of the embodiment shown in FIG. 22A in a closed position.

FIGS. 22A-22C are various views of another alternate embodiment of the self-ligating bracket shown in FIGS. 19A-19E in which the bores 636f and 638f have been configured as a FIG. 8-shape so that the locking clip 626f can slide-rotate between an open position (e.g., a lingual-occlusal side 636f' and 638' of the respective bore 636f, 638f) and a closed position (e.g., a labial-gingival side 636f" and 638r of the respective bore 636f, 638f).

Figure 23A:
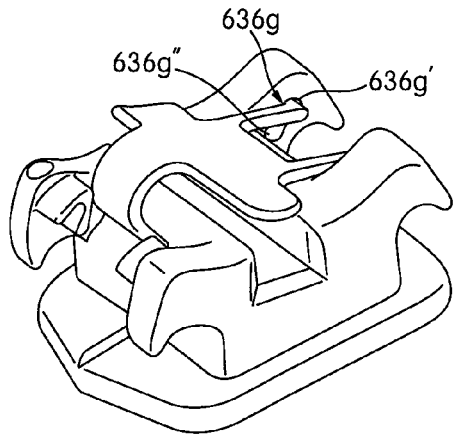
FIG. 23A is a top perspective view of a twenty-third embodiment of the present invention.
Figure 23B:
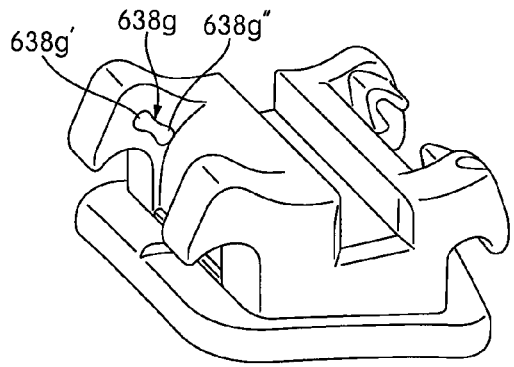
FIG. 23B is another top perspective view of the embodiment shown in FIG. 23A without a locking clip.

FIGS. 23A-23B are various views of another alternate embodiment of the self-ligating bracket shown in FIGS. 19A-19E in which the bores 636g and 638g have been configured as a FIG. 8-shape so that the locking clip 626g can slide-rotate between an open position (e.g., a labial-occlusal side 636g' and 638g' of the respective bore 636g, 638g) and a closed position (e.g., a lingual-gingival side 636g" and 638g" of the respective bore 636g, 638g).

Unlike the free rotating hinged clip design that only rotates about a fulcrum as discussed herein, this additional embodiment may include both rotational and sliding motion separately or preferably at the same time. It is believed that the sliding-up motion during the clip closing, FIGS. 23D-23E, less stress may be generated in the clip so that permanent deformation may be prevented.

Figure 24A:
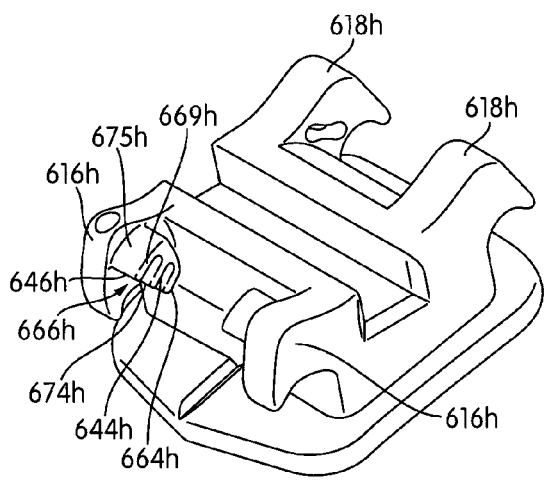
FIG. 24A is a top perspective view of a twenty-forth embodiment of the present invention without a locking clip.
Figure 24B:
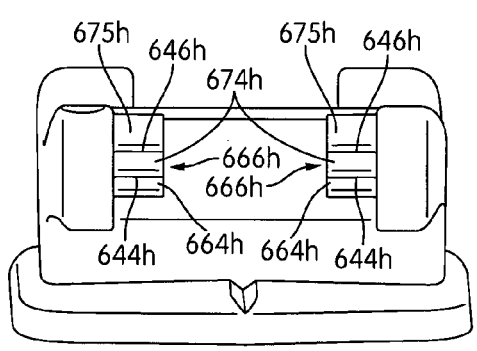
FIG. 24B is front view of the embodiment shown in FIG. 24A.

FIGS. 24A-24B are various views of another alternate embodiment of the self-ligating bracket shown in FIGS. 19A-19E in which a second pair of retaining (lingual) openings 666h may be further provided. In this specific embodiment, the retaining member 627h may include a first pair of stops 644h and a second pair of stops 646h on the gingival tie wings 616h to inhibit inadvertent movement of the locking clip 626h from a closed position (e.g., an active first closed position in stops 644h or a second closed position in stops 646h) to an open position and optionally to maintain the locking clip 626h open when it is pivoted to the open position. Each stop defining a first opening, at least one guide portion, and at least one flange. The first pair of stops 644h extend generally outward from the respective gingival tie wings 616 and include a first opening 664h, a first guide portion 674h, and a first flange 668h for engagement with the locking clip 626h to maintain the first closed position (e.g., active bracket for active first closed position). Similarly, the second pair of stops 646h extend generally outward from the respective gingival tie wings 616 and include a second opening 666h, a guide portion 675h, and a second flange 669 for engagement with the locking clip 626h to maintain the second closed position (e.g., passive bracket for passive second closed position). It is appreciated that the first and second pairs of stops 644h and 646h may positioned so that one stop of each pair of stops 644h and 646h is gingivally-occlusally juxtaposed to the respective other stop of each pair of stops 644h and 646h. Desirably, the pairs of stops on each gingival tie may define a generally W-shaped configuration.

As shown in FIGS. 22 and 24, the present invention may include another embodiment of a self-ligating bracket having a clip sliding/pivoting mechanism that may be configured to reduce the tension in the clip and/or prevent any resulting permanent deformation of clip so as to generally maintain the functionality of the clip.

The present invention may further provide another embodiment of the self-ligating bracket as shown in FIGS. 25A-25H. Generally, the self-ligating bracket may include a body molded with a base and a C-Shape clip. The clip has two bent ends that slide over the archwire slot in both gingival and occlusal directions and depending on the mode of closing (gingival or occlusal), the system will behave active or passive during the course of treatment. More particularly, this bracket concept has three components (see in the above picture): Body, Clip and Base. The clip may be shaped like a C and it is capable of closing in both gingival and occlusal mode. With a rectangular/square arch wire sits in the slot of body, this clip can express both the Passive and the Active engagement with the same ach wire depending on which end of clip covers the slot of arch wire. The uniqueness of this concept is the ability to change from a Passive stage to an Active stage (or vice-versa) without changing the wire. However, it is anticipated that the circular wire will tend to remain passive stage in both gingival and occlusal closing modes. The clip has a C-side shape (see the following picture) and has two bent ends. The two ends of clip have two different clip-spans (see the red arrows in the following picture). In the Orthodontic treatment stages, the bracket has the passive stage (no contact between the arch wire and the clip) and the active stage (Interference contact between the arch wire and the clip). See the following pictures for the details. In the Passive stage (FIG. 25G) when the bigger end (e.g., gingival end) of the clip covers the arch wire, there is no contact between the clip and the arch wire. When the clip is in the open position, it doesn't cover the arch wire, FIG. 25H. In the Active stage (FIG. 25I) when the smaller end of the clip covers the arch wire, there is interference contact between the clip and the arch wire. Desirably, dual stage brackets may be designed to have the interactivity between the clip and the arch wire for both Passive stage and Active stage.

FIG. 25J shows the interactivity between the arch wire and the occlusal end of clip in the Passive stage. The same design principal can be used on the gingival end of clip in the Active stage for the interactivity between the arch wire and the gingival end of clip. Desirably, during the Passive stage, there is no physical contact between the arch wire and the clip. However, in some crowded occlusal cases, the arch wire will start to contact with the clip. Because the clearance above the clip in the retainer channel (area between the occlusal free end of the clip and the lingual surface of the retainer wall (e.g., hood), the interactivity between the clip and the arch wire will be achieved.

In this specific embodiment, the self-ligating bracket of the present invention in which the bracket 1010q includes a modified locking clip 1026q and a modified receiving members 1036q. The receiving members 1036q may include a first receiving member 1036q', which may be mesially and distally located about the gingival tie wings 1016q of the bracket body 1012q and may include a non-continuous retaining (e.g., resting) channel 1090q which includes a mesial and distal portions 1091q to allow a positive seat for the respective tab portions 1031q of the locking clip 1026q. Desirably, the mesial and distal portions 1027q of the retaining channel 1090q extends generally in a parallel manner to the archwire slot 1020q. In this specific embodiment, the width of the locking clip 1026q at the labial free end 1030q may be generally the same mesial-distal width of the bracket body 1012q. Furthermore, the labial free end 1030q of the locking clip 1026q may include a notch portion 1034q disposed between the tab portions 1031q. The retaining channel may be further defined by a generally c-shaped profile to not only provide a positive seat (and limit lingual movement of the labial free end 1030q), but may also provide a hood portion 1038h to limit labial movement of the labial free end 1030h while in the closed position. Optionally, the height (e.g., labial-lingual height) of the retaining channel 1090q may be sufficiently sized (e.g., less than or equal to the thickness of the archwire) so that archwire entrapment therein may be substantially prevented while the free end portion 1030q of the locking clip 1026q is in the closed position.

The receiving member 1036q may further include a second receiving member 1036q", which may be centrally located about the interwing region 1024q between the occlusal tie wings 1018q. The interwing region 1024q may include an open stop groove 1042 having protrusions 1044q to aid in movement of the clip from an open position to a closed position. Desirably the width of the labial-occlusal free end 1122q corresponds to the width of the interwing region 1024q for receiving the labial-occlusal free end 1122q.

Figure 25A:
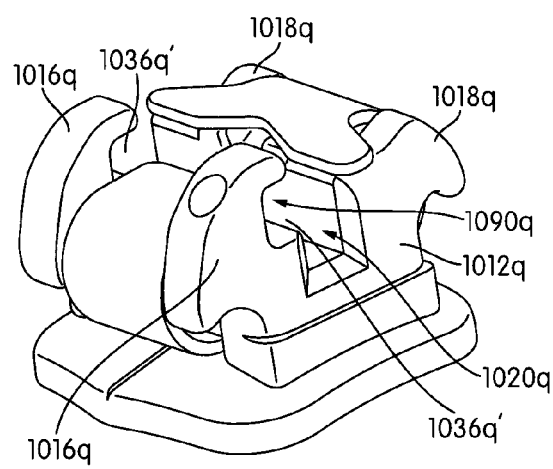
FIG. 25A is a top perspective view of a twenty-fifth embodiment of the present invention.
Figure 25B:
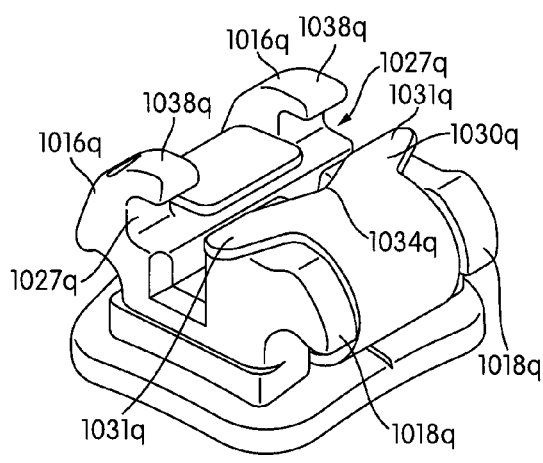
FIG. 25B is another top perspective view of the embodiment shown in FIG. 25A.
Figure 25C:
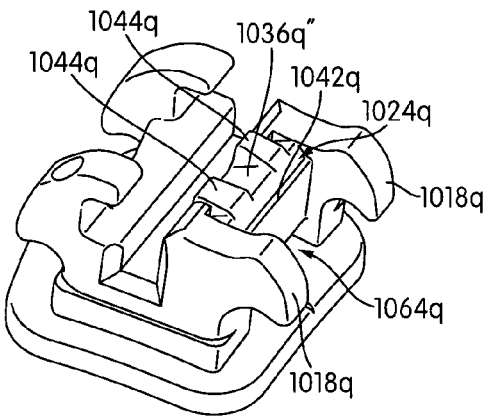
FIG. 25C is another top perspective view of the embodiment shown in FIG. 25A without a Locking clip.
Figure 25D:
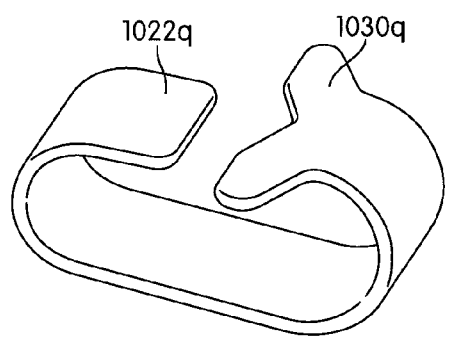
FIG. 25D is a rear perspective view of the locking clip from the embodiment shown in FIG. 25A.
Figure 25E:
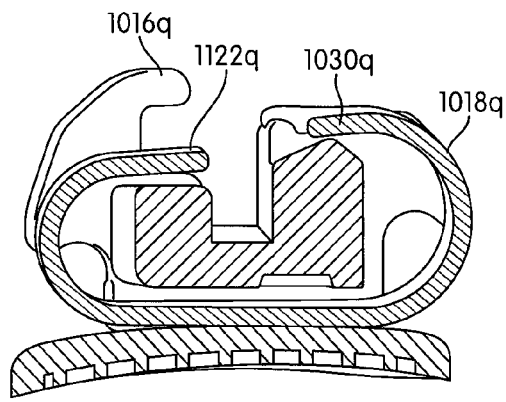
FIG. 25E is a cross-section view of the embodiment shown in FIG. 25A.
Figure 25F:
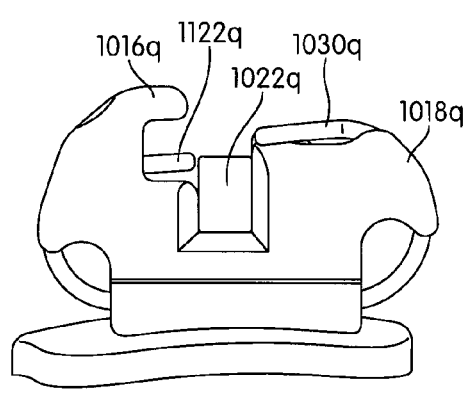
FIG. 25F is a side view of the embodiment shown in FIG. 25A in an open position.
Figure 25G:
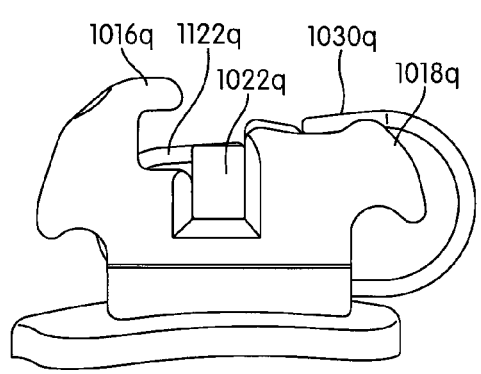
FIG. 25G is side view of the embodiment shown in FIG. 25A in a first closed position.
Figure 25H:
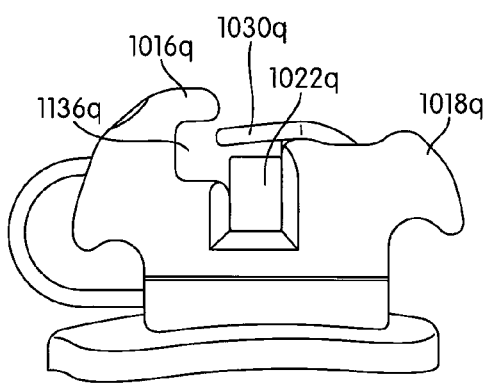
FIG. 25H is a side view of the embodiment shown in FIG. 25A in a second closed position.
Figure 25I:
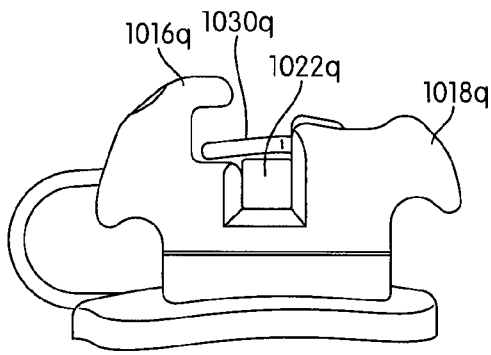
FIG. 25I is a side view of the embodiment shown in FIG. 25A in a third closed position.

In this embodiment the bracket 1010q may be configured for two closed positions (an active closed position and a passive closed position) and an open position. In the active closed position (FIG. 25G), the locking clip 1026q is occlusally displaced such that the labial-gingival free end 1030q is actively engaging the archwire 1022q locking clip 1026. In the passive closed position (FIG. 25H), the locking clip 1026q is gingivally displaced such that the labial-occlusal free end 1122q closes off (e.g., covers) the archwire slot 1020 while substantially free of contact with the archwire. Advantageously, the locking clip 1026q may be further displaced gingivally as shown in FIG. 25I to accommodate smaller archwires in a passive closed position. In the open position (FIG. 25F), the locking clip 1026q is generally positioned so that a spacing 1124q between the labial-gingival free end 1030q and the labial-occlusal free end 1122q is orientated generally parallel to the archwire slot 1020 so as to allow for removal of the archwire 1022, located therein.

FIGS. 26A-26H are various views of another embodiment of a self-ligating bracket of the present invention, which may include a body 1012r (e.g., Rhomboid body design) molded with a base 1014r and at least one clip 1026r (e.g., a plurality of clips). More particularly, the clips 1026r (e.g., metal clips) and body gear racks 1126r can be formed through a micro-machining process. The clip 1026r and body 1012r may be designed as a mating gear rack mechanism or otherwise along the labial-lingual direction allowing the clip to lock at different positions for different wire sizes. The adjustable clips 1026r include racks 1128r, which correspond and/or mate with the respective body gear racks 1126r for ratcheting/adjusting of the clips 1026r. The adjustable clips 1026r can also allow for the adjustment between a passive, active, and interactive engagement on the arch wire (e.g., Passive engagement refers to when the clip does not contact the arch wire while Active engagement may refer to when the clip is applying a force directly on the arch wire). Interactive engagement may occur when the clip engages with the arch wire but does not apply a force or substantially no force on the arch wire. When a plurality of clips are included, the two clips are desirably independent of each other so it is possible to have engagement on the arch wire on one side alone.

The clip-wire interactions may be adjusted in various ways. For example, the clip-wire interaction may be adjusted by one or more of the following, but not limited to: Active Engagement on the arch wire on the mesial and distal sides of the bracket body; Passive Engagement on the arch wire on the mesial and distal sides of the bracket body; Interactive Engagement on the arch wire on the mesial and distal sides of the bracket body; Active Engagement on the arch wire on the mesial side and Passive Engagement on the distal side of the bracket body; Active Engagement on the arch wire on the distal side and Passive Engagement on the mesial side of the bracket body; Interactive Engagement on the arch wire on the mesial side and Passive Engagement on the distal side of the bracket body; Interactive Engagement on the arch wire on the distal side and Passive Engagement on the mesial side of the bracket body; Active Engagement on the arch wire on the mesial side and Interactive Engagement on the distal side of the bracket body; Active Engagement on the arch wire on the distal side and Interactive Engagement on the mesial side of the bracket body; and any combination thereof.

Figure 26A:
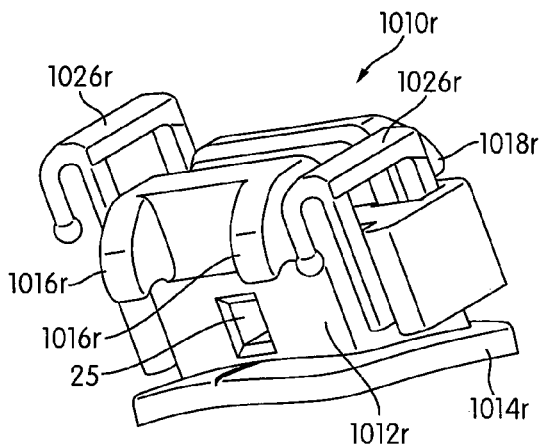
FIG. 26A is a top perspective view of a twenty-sixth embodiment of the present invention.
Figure 26B:
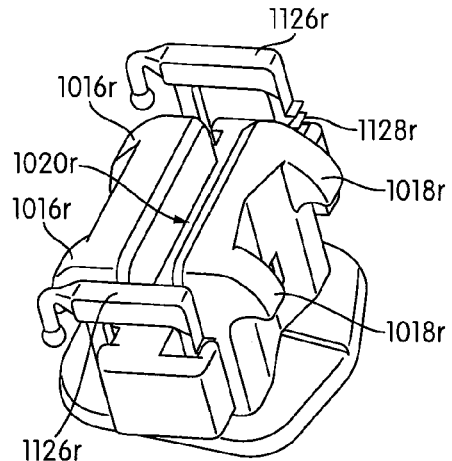
FIG. 26B is another top perspective view of the embodiment shown in FIG. 26A.
Figure 26C:
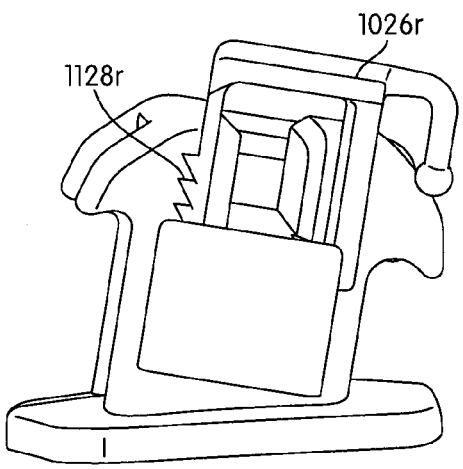
FIG. 26C is a side view of the embodiment shown in FIG. 26A.
Figure 26D:
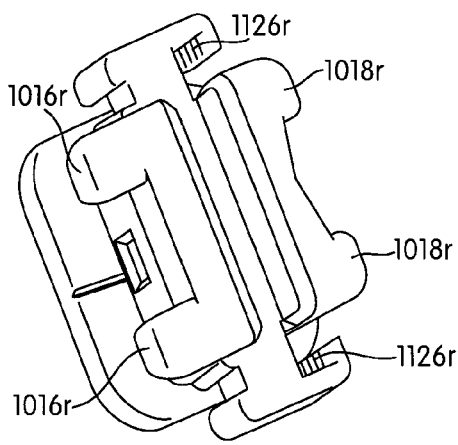
FIG. 26D is another top perspective view of the embodiment shown in FIG. 26A without a locking clips.
Figure 26E:
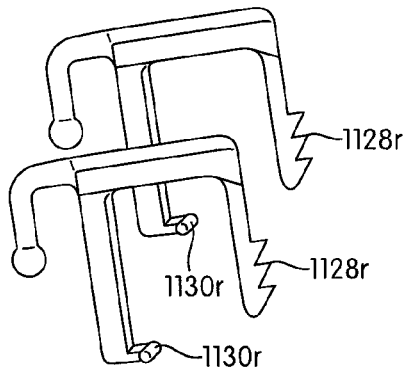
FIG. 26E is a rear perspective view of the locking clips from the embodiment shown in FIG. 26A.
Figure 26F:
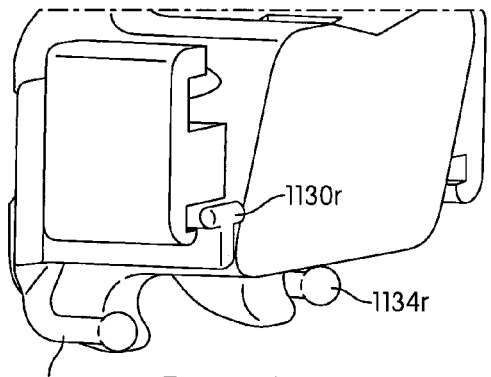
FIG. 26F is a zoomed-in bottom perspective view of the embodiment shown in FIG. 26A without a base portion.
Figure 26G:
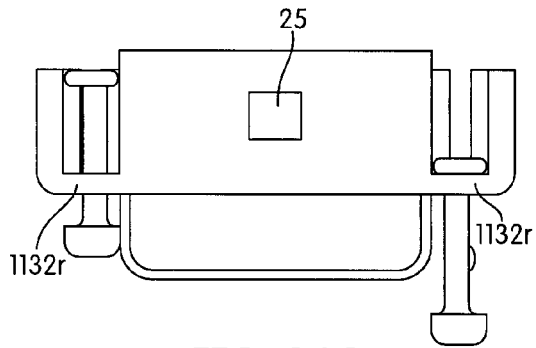
FIG. 26G is a front view of the embodiment shown in FIG. 26A.
Figure 26H:
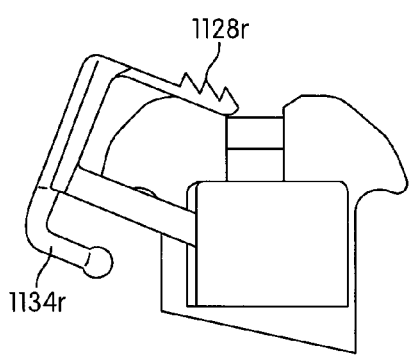
FIG. 26H is a side view of the embodiment shown in FIG. 26A in an open position.

The clips 1026r may be opened using a scalar or other common dental instrument by applying a force at the edge of the gear rack 1128r (e.g., ratcheting system) on the clip and pulling the clip in the labial direction. The orientation of the gear rack 1128r allows the clips to be closed by pushing towards the lingual direction. As shown in FIGS. 26G-26H, a rounded knob 1130r on the clip on the opposite side of the gear rack allows the clip to slide easily in the labial direction to a stop 1132r that is built in the body of the bracket. When the round knob 1130r reaches the stop 1132r on the body, the gear rack 1128r on the clip is disengaged from the mating gear rack 1126r on the body and the clip can then pivot so that it is no longer block the arch wire slot 1020r and an arch wire 1022r can be removed or inserted (FIG. 26I). A post 1134r (e.g., hook) may be attached to each clip for elastics ligation. The elastics that can be ligated can be used for aesthetic purposes allowing different color ligatures to be attached with affecting the performance of the bracket. Elastics can also be attached to help with leveling and aligning and tooth extrusion.

FIGS. 27A-27G are various views of another alternate embodiment of the self-ligating bracket shown in FIGS. 24A-24B in which a first and second pair of retaining members are provided on the occlusal side of the gingival tie wings. Generally, the self-ligating bracket may include a body 612i molded with a base 614i and a sliding locking clip 626i. More particularly, the bracket body may include two retainer channels (e.g., openings) 664i, 666i that may be used to allow the clip 626i to utilize two treatment stages (Passive and Active) with the same arch wire. This bracket concept may also be designed to have three different directions, gingival, occlusal, lingual, to open, close and change treatment stage (Active vs. Passive), respectively.

The bracket may include three components such as a body, base and clip. For illustration purposes, a rectangular/square arch wire sits in the slot of body. Please note that the slot is capable of accommodating round wires as well. As shown in the figures, the labial free end 692i of the clip may designed to have a "post" (e.g., a T-shaped free end) like feature that when closed first sits in a passive clip retaining channel (e.g., longitudinally positioned spaced apart labial openings). At this position (FIG. 27F) there may be substantially or completely no contact between the clip and the arch wire, which is the passive stage of orthodontic treatment.

Figure 27A:
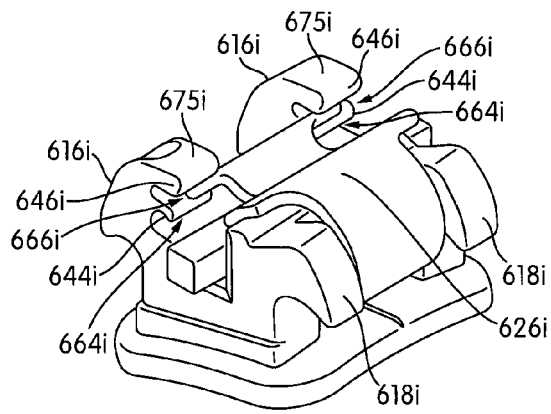
FIG. 27A is a top perspective view of a twenty-seventh embodiment of the present invention.
Figure 27B:
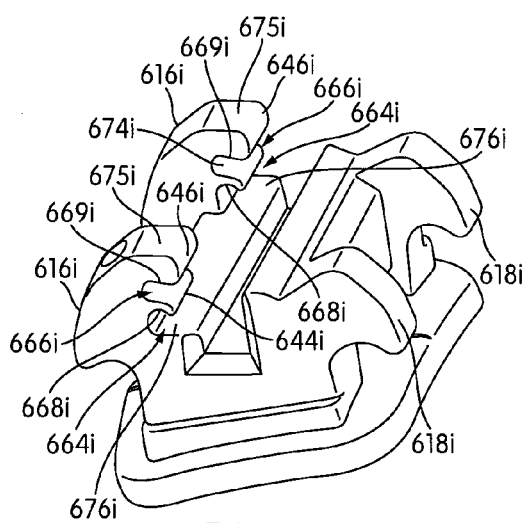
FIG. 27B is another top perspective view of the embodiment shown in FIG. 27A without a locking clip.
Figure 27C:
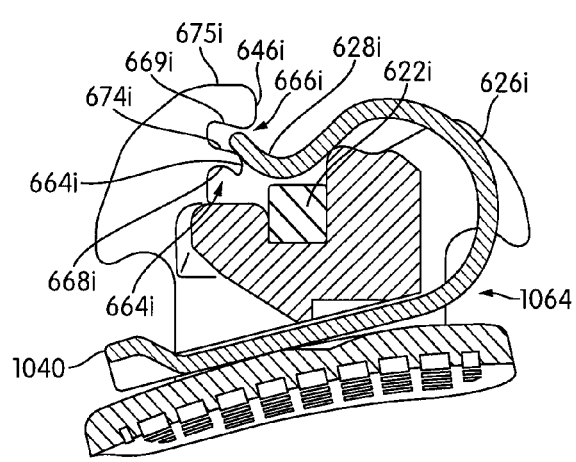
FIG. 27C is a cross-section view of the embodiment shown in FIG. 27A.
Figure 27D:
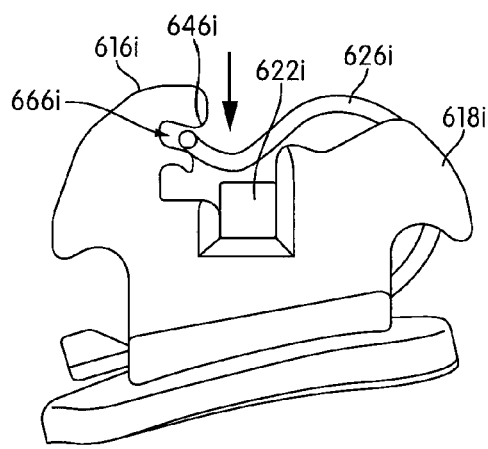
Figure 27E:
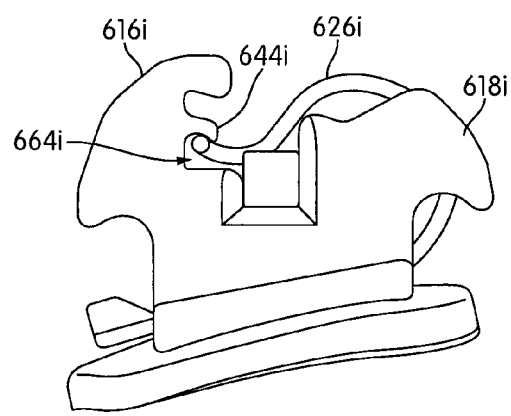
Figure 27F:
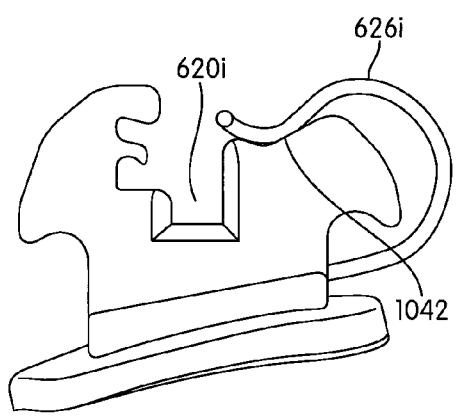
Figure 27G:
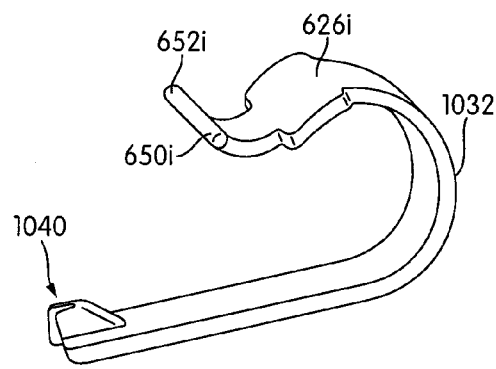

Typically, as treatment progresses, the clip may needs to be changed from the passive stage (no contact between the clip and the arch wire, FIG. 27F) to the active stage (Interference contact between the clip and the arch wire, FIG. 27G) where the post feature sits in the active clip retaining channel (e.g., longitudinally spaced apart lingual openings being generally positioned below the passive retaining channels). The mechanism to change the clip (FIG. 27I) from the Passive stage to the Active stage may be to simply apply a force and push down on the labial free end portion of the clip (shown in the arrow in FIG. 27D), to the active clip resting channel. As shown in FIG. 27F, the labial free end portion of the clip may be position in a mesial-distal resting groove 1042 while in the open position. The number of clip retaining channels may be reduced or increased if needed, and the channel positions (with respect to bottom of the archwire slot) can be altered if necessary too.

In this specific embodiment, the retaining member 627 may includes a first pair of stops 644i and a second pair of stops 646i on the occlusal side of the gingival tie wings 616i to inhibit inadvertent movement of the locking clip 626i from a closed position (e.g., an active first closed position in stops 644 or a second closed position in stops 646i) to an open position and optionally to maintain the locking clip 626i open when it is pivoted to the open position. Each stop defining a first opening, at least one guide portion, and at least one flange. The first pair of stops 644i extend generally outward from the respective gingival tie wings 616i and include a first opening 664i, a first guide portion 674i, and a first flange 668i for engagement with the locking clip 626i to maintain the first closed position (e.g., active bracket for active first closed position). Similarly, the second pair of stops 646i extend generally outward from the respective gingival tie wings 616 and include a second opening 666, a guide portion 675i, and a second flange 669i for engagement with the locking clip 626i to maintain the second closed position (e.g., passive bracket for passive second closed position). It is appreciated that the first and second pairs of stops 644i and 646i may positioned so that one stop of each pair of stops 644i and 646i is gingivally-occlusally juxtaposed to the respective other stop of each pair of stops 644i and 646i. Desirably, the pairs of stops on each gingival tie may define a generally W-shaped configuration.

The locking clip 626i slides on the occlusal tie wings 618i and is moveable between two closed positions (FIGS. 27D-27E) where access to the archwire slot 620i is inhibited and an open position (FIG. 27F) where access to the archwire slot 620i is permitted. It is appreciated that the locking clip 626i is in the form of spring element having a generally U-shaped head configuration. More particularly, the locking clip 626 may include a head portion 628i, with a pair of opposing side arms 650i and 652i, which define an opening T-Shape configuration. It is appreciated that the head portion 628i and/or the side arms 650i and 652i are configured to extend across the archwire slot 620i.

The arms 650i and 652i may include free ends extending generally mesially and distally outward, though not required. The arms 650i and 652i may be received in the respective first openings 664*i* or the respective second openings 666*i*, which are formed in occlusal side of the gingival tie wings 616*i*.

To close the orthodontic bracket 610*i* in the first closed position (Active closed position), the locking clip 626 is slide gingivally towards the first pair of stops 644*i* (e.g., lingual first pair of stops) of the locking mechanism 627*i* about the gingival tie wings 616*i*. The arms 650*i* and 652*i* make contact with and are gingivally guided along the respective labial surface of the first guide portions 674*i*. The arms 650*i* and 652*i* are continually guided along the labial surfaces of the first guide portions 674*i* until the hook ends 672*i* extend beyond the flanges 668*i* of the first pair of stops 644*i*. This allows the locking clip 626*i* to snap back towards its non-stressed state so that the arms 650*i* and 652*i* engage the respective flanges 668*i* thereby maintaining the locking clip 626*i* in the first closed position. In doing so, the locking clip 626*i* is deflected lingually so that contact between the locking clip, the archwire, and the archwire slot may be substantially or completely maintained while in the first closed position (FIG. 27E).

To close the orthodontic bracket 610*i* in the second closed position, the locking clip 626 is slid towards the second pair of stops 646*i* of the locking mechanism 627*i* about the occlusal side of the gingival tie wings 616*i*. The arms 650*i* and 652*i* make contact with and are gingivally guided along the respective labial surface of the second guide portions 675*i*. The arms 650*i* and 652*i* are continually guided along the labial surfaces of the second guide portions 675*i* until the hook ends 672*i* extend beyond (e.g., gingivally-lingually) the first flanges 669*i* of the second pair of stops 646*i*. This allows the locking clip 626*i* to snap back towards its non-stressed state so that the hook ends 672*i* engage the respective second flanges 669*i* thereby maintaining the locking clip 626*i* in the second closed position. In doing so, the locking clip 626*i* may be slightly deflected lingually so that minimal or no contact between the locking clip 626*i* and the archwire may be maintained while in the second closed position (FIG. 27D).

As discussed above with reference to FIGS. 27A-27G, different slot locations may provide different clip status. For example, a labially positioned slot(s) and/or opening(s) may provide for a Passive stage closed position (e.g., FIG. 27D-generally no contact between arch wire and clip) or a lingually positioned slot(s) may provide for an Active stage closed position (e.g., FIG. 27E-contact and interference between archwire and clip). It is appreciated that the ratchet(s) and/or slot(s) may be positioned such that an expressive stage closed position may result where minimal contact occurs between arch wire and clip.

Referring now to FIGS. 28A-28B, a self-ligating orthodontic bracket is shown and is generally indicated to by reference numeral 10. As can be seen, orthodontic bracket 10 includes a body 12 and a lingual mounting base 14 attached to the body. The mounting base 14 has a lingual surface to be attached to a tooth. The body 12 may include a side wall 15 extending between the base 14 and a labial surface 19 to define a generally curved-shaped perimeter. Desirably, the perimeter of the body 12 defines a circular, oval, or otherwise shaped member. However, it is appreciated that the body 12 may be defined by various other shaped configurations such as a square-shaped, a rectangular-shaped a rhomboid-shaped, or otherwise shaped member. When provided, it is believed that the curved-shaped (e.g., oval-shaped) body 12 may reduce dental calculus or otherwise buildup about the perimeter of the body 12 and/or allow for easier removal thereof.

A pair of laterally spaced gingival tie wings 16 and a pair of laterally spaced occlusal tie wings 18 extend from the labial surface 19 of the body 12. The gingival tie wings 16 and the occlusal tie wings 18 generally curve lingually. An interwing region 24 extends gingivally-occlusally across the body 12 and may be generally defined by the lateral spacing of the gingival tie wings 16 and the lateral spacing of the occlusal tie wing 18. The interwing region 24 may be an opened (e.g., unobstructed) passageway or may be a closed (partially or completely obstructed) passageway, or otherwise. An archwire slot 20 extends mesially-distally across the body 12 and between the gingival and occlusal tie wings 16 and 18. The archwire slot 20 opens labially to receive an archwire 22. The archwire slot 20 is interrupted in the interwing region 24 of the body.

It is appreciated that the body 12 may also include an interior slot for receiving an optional auxiliary wire. Desirably, the body 12 may include at least one interior vertical slot 25 that extends occlusally-gingivally (e.g., generally parallel to the interwing region 24) through the body 12, though not required.

The bracket 10 may further include a locking mechanism that includes a locking clip 26 and a retaining member 27 for maintaining the locking clip 26 in the closed position. In one embodiment, the retaining member 27 may include stops 44 and 46 on the gingival tie wings 16 to inhibit inadvertent movement of the locking clip 26 from a closed position to an open position and to maintain the locking clip 26 open when it is pivoted to the open position. The stops 44 and 46 extend generally towards one another from the respective gingival tie wings 16 so as to define a reduced opening 48 in the interwing area 24. Desirably, the stops 44 and 46 may form a circular (e.g., semi-circular) shape extending from the respective mesial and distal surfaces of the gingival tie wings 16 in the interwing are 24. However, it is appreciated that the stops 44 and 46 may form other shapes that include curved, arcuate, angled, flat, or otherwise portions.

The locking clip 26 is pivotally mounted on the occlusal tie wings 18 and is moveable between a closed position where access to the archwire slot 20 is inhibited by stops 44 and 46 and an open position where access to the archwire slot 20 is permitted. It is appreciated that the locking clip 26 is in the form of spring element having a generally cruciform outline. In one embodiment, the locking clip 26 may include a gingival head 28, which curves lingually to define a forwardly (e.g., gingivally) projecting hook 72. The head 28 may include interconnected opposing side portions 30, which define a width (e.g., mesial-distally) that is typically larger than width of the reduced opening 48.

The locking clip 26 may also include a pair of oppositely directed arms 50 and 52 (e.g., mesially and distally extending arm portions) which extend generally along and across the archwire slot 20. It is appreciated, that the arms 50 and 52 may at least partially or substantially extend in a parallel manner with the archwire slot 20. Each arm 50 and 52 may form a generally U-shaped configuration having a gingival portion extending to an occlusal portion with an end portion 58, therebetween to define an opening 60 therebetween. It is appreciated that the end portion 58 can extend as wide as necessary in both the mesial and distal direction to achieve optimum rotational control of the archwire.

When included, the gingival and occlusal portions of the arms 50 and 52 may be configured to desirably achieve direct translation of forces from the locking clip 26 to the archwire 22 along a Facial Axis FA (e.g., generally perpendicularly to the archwire slot 20). As can be seen in FIG. 28D, both gingival and occlusal portions (e.g. corners 86 and 87) of the archwire 22 may be engaged by the arms 50 and 52 (e.g., gingival and occlusal portions of the arms 50 and 52) in the closed position so as to directly translate the forces from the archwire 22 to the FA point on the tooth so as to optimize treatment time of the patient.

The locking clip 26 may also include opposed free ends (e.g., extending generally mesial and distal, though not required) that are out-turned to define oppositely directed spaced apart tail ends 32 and 34 respectively. Each of the tail ends 32 and 34 is received in a respective bore 36 and 38 formed in one of the occlusal tie wings 18. The bores 36 and 38 may extend (e.g., mesial-distally) completely through the respective tie wings 18 or partially therethrough. The tail ends 32 and 34 may include a flange portion 40 and 42 extending (e.g., radially) from the clip 26. The flange portion 40 and 42 may be configured to act as a stop for the tail ends 32 and 34 when inserted in the respective bores 36 and 38. Desirably, the flange portions 40 and 42 may prevent the tail ends 32 and 34 from extending beyond a predetermined depth into and/or beyond the bores 36 and 38.

It is further contemplated that the locking clip 26 may be in a compressed state such that the tail ends 32 and 34 exert a generally continual outward force on the respective tie wings 16 (mesially for mesially-gingival tie wing 16 and distally for the distally-gingival tie wing 16) thereby maintaining the tail ends 32 and 34 within the respective bores 36 and 38. In doing so, the tails 32 and 34 are generally free to rotate within the respective bores 36 and 38 to permit pivotal movement of the locking clip 26 between the opened and closed positions.

In another embodiment, the stops 44 and 46 may form multiple stop portions (e.g., semi-circular portions) (not shown), each set of stop portions extending from the respective inner surface of the gingival ties wings 16 (e.g., into the interwing region 24). For example, the multiple stop portions may include a pair of labially-lingually spaced apart stops along the inner surface of each of the gingival tie wings 16. When included, the pairs of opposing pairs of stops may be configured to allow the locking clip 26 movable between an open position and two different closed positions. More particularly, a first pair of opposing labial stops may include a labial-mesial stop and a labial-distal stop while the second pair of opposing lingual stops may include a lingual-mesial stop and a lingual-distal stop, with the first pair of opposing labial stops being labially spaced from the second pair of opposing lingual stops. In the first closed position, the hook 72 may be positioned below the second pair of opposing lingual sops and the labial surface 19 of the body 12 in the gingival interwing area 24 to define an active first closed position. In the second closed position, the hook 72 may be positioned below between the first pair of opposing labial stops and the second pair of opposing lingual stops in the gingival interwing area to define a second closed position.

The locking clip 26 is generally configured to withstand typical forces incurred by the bracket while substantially maintaining the locking clip 26 in the closed position. Typical forces may include, but are not limited to forces resulting from the movement of the archwire, the clip, and/or the bracket relative to one another or otherwise such as movement caused by brushing your teeth and/or eating food. However, it is appreciated that the clip 26 may also be configured to allow deformation thereof resulting from a sufficient amount of force, which is generally greater than the typical forces described above. For example, as the dentist urges the head 28 against the stops 44 and 46 with a sufficient amount of force, the opposing side portions 30 deform towards one another so as to reduce the width of the head 28 thereby allowing the head 28 to pass through the reduce opening 48 while moving the locking clip between the open position and the closed position. After passing through the reduced opening 48, the head 28 generally returns to its typical non-deformed shape (e.g., non-stressed state).

The stops 44 and 46 contact a labial surface of the locking clip 26 about the hook portion 72 when the locking clip 26 is in a closed position to inhibit the locking clip from accidentally opening during application in the patient's mouth.

As can be seen in FIG. 28A, the stops 44 and 46 retain the locking clip 26 against the archwire 22 and inhibit relative movement between the archwire 22 and the body 12 of the orthodontic bracket 10. To release the archwire 22, the locking clip 26 is pivoted about the tails 32 and 34 while applying a sufficient amount of force against the stops 44 and 46. As a sufficient amount of force is being applied to the head 28 during engagement of the stops 44 and 46, the width of the head 28 is reduced thereby allowing it to pass through the reduced opening 48.

In another embodiment as shown in FIGS. 28C-28D, a self-ligating orthodontic bracket 110 is provided. The bracket 110 may comprise a locking mechanism including the locking clip 126 and an alternate retaining member 127. In this embodiment, the retaining member 127 is in the form of a first member 121 and a second member 123 with a reduced opening 148 therebetween. The first and second members 121, 123 may extend labially from the labial surface 119 of the body 112 in an occlusally-gingivally relationship relative to one another about the gingival interwing area 124.

At least one stop similar to that of the previous embodiment may be provided on one of the first and second members 121, 123 to inhibit inadvertent movement of the locking clip 126 from a closed position to an open position and to maintain the locking clip 126 open when the locking clip 126 is pivoted to the open condition. The stop may be included in various shapes and/or configurations such that they provide a reduced opening 148 between the first and second members 121, 123. In one specific example, the second member 123 (e.g., occlusally positioned relative to the first member 121) may include a stop 144 that extends from a gingival surface of the second member 123 at a free end 128. The stop 144 may be generally similar in shape to the stop 44 as discussed above including curved portions to help guide the head 128 of the clip 126 between open and closed positions. The first member 121 (gingivally positioned relative to the second member 123) may include a stop 146 that extends from occlusal surface of the first member 121 at a free end 130. The stop 146 may be generally shaped as a ramp portion that gradually increases thickness (e.g., taper) as it extends towards a flat portion at the free end 130 to help guide hook portion 172 of the head 28 of the clip 126 between open and closed positions. The stops 144 and 146 generally oppose one another to form the reduced opening 148 therebetween. Desirably, in a non-stressed state, the reduced opening 148 may be dimensioned (occlusally-gingivally) with a maximum spacing that is less than the thickness of the head 128 to substantially prevent movement of the clip 126 between the open position and the closed position. It is appreciated that non-stressed state herein may be defined as (in non-stressed state such as in the open or closed positions of the bracket 110 shown in FIGS. 6 and 7).

It is appreciated that at least one or both of the first and second members 121, 123 may be configured to deform away from the other to allow movement of the clip 126 between open and closed positions. Deformation of the first member 121 and/or the second members 123 may occur upon contact by the clip 126 (e.g., head 128) with a sufficient force (e.g., by the dentist). For example, as the dentist urges the head 128 against the stops 144 and 146 with a sufficient amount of force, at least one (e.g., or both) of the first and second members 121, 123 deform towards the another so as to increase the spacing of the reduced opening 148 between the stops 144, 146 thereby allowing the hook portion 172 of the head 128 to pass through the widened reduced opening 148 while moving the locking clip 126 between the open position and the closed position. After passing through the reduced opening 148, the first member 121 and the second member 123 generally return to their typical non-deformed shape (e.g., non-stressed state) while returning the reduced opening 148 to it maximum spacing thereby maintaining the clip 28 in the open or closed positions. It is further appreciated that the hook portion 172 (or other portion(s) of the head 128) may deflect, deform, and/or compress to pass thorough the reduced opening 148, though not required.

More particularly, to close the orthodontic bracket 110, the locking clip 126 is pivoted about the tails 132 and 134. As the locking clip is pivoted, the head 128 of the clip 126 is pushed into the gingival portion of the interwing region 124 against the stops 144, 146. The reaction force applied to the stops 144, 146 by the head 128 of the locking clip 126 causes the at least one of the first and second members 121, 123 to move occlusally-gingivally in a direction away from one another. When the locking clip 126 is pivoted beyond the stops 144 and 146, the first member 121 and/or the second member 123 snaps back into its non-stressed state (e.g., generally upright and/or perpendicular from the labial surface 119) and the head 126 is biased towards the labial surface 119 to its closed position below the stops 144 and 146. The stops 144 and 146 in this condition inhibit the locking clip 126 from moving back towards the open position. In this way, the archwire slot 120 remains closed securing the archwire 122 in the archwire slot.

Referring now to FIG. 28E, yet another embodiment of a self-ligating orthodontic bracket 210 is shown. The bracket 210 may comprise a body 212, a base 214, and a locking mechanism including the locking clip 226 and a retaining member 227. The body 212 may include gingival tie wings 216 and occlusal tie wings 218 with a mesially-distally extending archwire slot 220 therebetween. In this specific example, the body 212 has a rectangular-shaped body and includes a first bridge portion 260 in the interwing region 224, which spans between the gingival tie wings 216. The first bridge portion 260 extends from labial surface of the archwire slot 220 to the labial surface the gingival tie wings. The body 212 may also include a second bridge portion 261 in the interwing region 224, which spans between the occlusal tie wings 218. It is appreciated that the second bridge portion 261 extends partially from the labial surface of the archwire slot 220 to allow for rotation of the locking clip 226. The body 212 may also include an interior slot for receiving an optional auxiliary wire, though not required. In one specific embodiment, the body 212 may include an interior vertical slot 225 that extends occlusally-gingivally (e.g., generally transverse to the archwire slot 220) through the body 212.

The locking clip 226 may be in the form of a generally U-Shaped spring element having out-turned free mesial and distal ends defining laterally spaced tails 232 and 234. Each of the tails is pivotally received within a respective bore 236 and 238 formed in the respective one of the occlusal tie wings 218.

The retaining member 227 is provided in the first bridge portion 260 and may include sets of opposing stops 244 and 246 similar to that of the first embodiment, which may be provided on the bridge 260 to maintain the locking clip 226 within recesses 262 in the closed position.

More particularly, to close the orthodontic bracket 210, the locking clip 226 is pivoted about the tails 232 and 234. As the locking clip 226 is pivoted, the clip arms 250 and 252 of the head portion 228 are pushed into the bridge portion 260 against the respective pairs of opposing stops 244 and 246. The reaction force applied to the sets of opposing stops 244 and 246 by the clip arms 250 and 252 causes the clips arms 250 and 252 and/or the opposing stops 244 and 246 to deform thereby allowing the clip arms 250 and 252 to pass through reduced openings 248 between the open and closed positions. When the clip head 228 is pivoted beyond the sets of opposing stops 244 and 246, the clip arms 250 and 252, the opposing stops 244 and 246, or a combination of both snap back into their non-stressed state and the head 226 is biased towards the labial surface 219 about the recesses 262 to its closed position below the respective sets of opposing stops 244 and 246. The sets of opposing stops 244 and 246 in this condition (e.g., non-stressed state) inhibit the locking clip 226 from moving back towards the open position. In this way, the archwire slot 220 remains closed thereby securing the archwire (not shown) in the archwire slot 220.

Referring now to FIGS. 28F-28G, another embodiment of a self-ligating orthodontic bracket is shown and is generally indicated to by reference numeral 310. In this embodiment, the bracket 310 may comprise an oval body 312, a base 314, and a locking mechanism including a locking clip 326 and a retaining member 327. The body 312 may include gingival tie wings 316 and occlusal tie wings 318 with a mesially-distally extending archwire slot 320 therebetween. A first bridge portion 360 and a second bridge portion 361 may be in the interwing region 324, with the first bridge portion 360 spanning between the gingival tie wings 316 and the second bridge portion 361 spanning between the occlusal tie wings 318. It is appreciated that the first bridge portion 360 and/or the second bridge portion 361 may extend partially or entirely from the labial surface of the archwire slot to labial surface of the respective tie wings 316 and 318. In one specific example, the first and second bridge portions 360 and 362 extend from labial surface of the archwire slot up to the labial surfaces of the respective tie wings 316 and 318.

The body 312 may also include an interior slot for receiving an optional auxiliary wire, though not required. For example, the body 312 may include an interior vertical slot 325 that extends occlusally-gingivally (e.g., generally transverse to the archwire slot 320) through the body 312.

The locking clip 326 may be in the form of a generally U-Shaped spring element having a mesially-distally extending gingival head portion 328, a pair of oppositely directed arm portions 350 and 352, and in-turned free mesial and distal ends defining laterally spaced tails 332 and 334 extending respectively from arms 350 and 352 and free ends 358, therebetween. Each of the tails 332 and 334 is pivotally received within a respective bore 336 and 338 formed in the respective one of the occlusal tie wings 318. More particularly, the tails 332 and 334 are received within the respective bore 336 and 338 along the outer surface of the respective occlusal tie wing (e.g., the mesial side of the mesial-occlusal tie wing and the distal side of the distal-occlusal tie-wing 318). In this specific embodiment, the locking clip 326 may include a biasing member 370, which extends lingually from the head portion 328 to define a forwardly projecting labial hook 372 and a lingual guide portion 374.

The retaining member 327 may be provided in the first bridge portion 360 and desirably includes a first opening 364 in the labial face of the first bridge portion 360 and a second opening 366 in the gingival face of the first bridge portion 360. Desirably, the first opening 364 and the second opening 366 define a throughhole 362 therebetween for receiving the biasing member 370 to maintain the locking clip 326 in the closed position.

The second opening 366 on the gingival surface of the bridge portion 360 includes a lingual flange 368, which engages the labial hook 372 when the locking clip 326 is in the closed position. The engagement between the flange 368 and the labial hook 372 maintains the locking clip in the closed position while retaining the locking clip 326 against the archwire thereby inhibiting relative movement between the archwire and the body 312 of the orthodontic bracket 310. To close the orthodontic bracket 310, the locking clip 326 is pivoted about the tails 332 and 334 towards the first bridge portion 360. As the lingual guide 374 contacts the gingival edge 376 of the first opening 364, the biasing member deflects (e.g., biases) occlusally thereby allowing the lingual guide 374 into the throughhole 362.

Desirably, the lingual guide 374 is provided at the free end of the biasing member 370 and includes a portion that is configured to direct the biasing member 370 into the first opening 360 and into the throughhole 362. It is appreciated that the guide portion may be curved, arcuate, angled, flat, or otherwise shaped to aid in directing the biasing member 370 into the closed position.

The reaction force applied to the gingival edge 376 of the first opening 364 by the lingual guide 374 causes the biasing member 370 to deflect (e.g., occlusally) thereby allowing the labial hook 372 to pass through the first opening 364 and into the throughhole 362 between the open and closed positions. When the hook portion 372 is pivoted lingually beyond the flange 368 in the throughhole 362, the biasing member 370 snaps back towards its non-stressed state and the lingual hook 372 engages the flange 368 of the throughhole 362 to its closed position. The biasing member 370 in this condition (e.g., non-stressed state) inhibits the locking clip 326 from moving back towards the open position. In this way, the archwire slot 320 remains closed thereby securing the archwire in the archwire slot.

At least one labial face of the gingival tie wings 316 and the bridge portion 360 may include a groove 380 having a shape complementary for receiving a portion of the locking clip 326 (e.g., head portion 328) while in the closed position. It is contemplated that the groove 380 may be configured with an angled or curved portion to aid in guiding the lingual guide 374 of the biasing member 370 into the first opening 364. Desirably, the labial faces of the gingival tie wings 316 (along the archwire slot) and the bridge portion 360 extending therebetween include the groove 380 having a generally semi-circular cross-section.

To release the archwire, the lingual guide 374 is moved (e.g., pushed) generally occlusally through the second opening 366 and into the throughhole 362 so that the hook portion 372 moves occlusally beyond the flange 368 thereby disengaging the hook 374 from the flange 368. Thereafter, the biasing member 370 may be removed from the retaining member 327 through the first opening 364 and the locking clip 326 is free to pivot about the tails 332 and 334.

Referring now to FIGS. 28H-28I, another embodiment of a self-ligating orthodontic bracket is shown and is generally indicated to by reference numeral 410. In this embodiment, the bracket 410 may comprise a rectangular body 412, a base 414, and a locking mechanism including a locking clip 426 and a retaining member 427. The body 412 may include gingival tie wings 416 and occlusal tie wings 418 with a mesially-distally extending archwire slot 420 therebetween. A first bridge portion 460 and a second bridge portion 461 is provided in the interwing region 424, with the first bridge portion 460 spanning between the gingival tie wings 416 and the second bridge portion 461 spanning between the occlusal tie wings 418. More particularly, the first bridge portion 460 extends from labial surface of the archwire slot up to the labial surface of the gingival tie wings 416 while the second bridge portion 461 extends only partially to the labial surface of the occlusal tie wings 418.

The body 412 may further include an interior vertical slot 425 that extends occlusally-gingivally (e.g., generally transverse to the archwire slot 420) through the body 412.

The locking clip 426 may be in the form of a generally U-Shaped spring element having a mesially-distally extending gingival head portion 428, a pair of oppositely directed arm ends 458 and in-turned free mesial and distal ends defining laterally spaced tails 432 and 434 extending respectively from arms 450 and 452. Each of the tails is pivotally received within a respective bore 436 and 438 formed in the respective one of the occlusal tie wings 418. More particularly, the tails 432 and 434 are received within the respective bore 436 and 438 along the outer surface of the respective occlusal tie wing (e.g., the mesial side of the mesial-occlusal tie wing 418 and the distal side of the distal-occlusal tie-wing 418). In this embodiment, the locking clip 426 may include a pair of spacedly disposed biasing members 470a and 470b, which extend lingually from the head portion 428 to define respective mesially and distally projecting labial hooks 472a and 472b and respective lingual guide portions 474a and 474b.

The retaining member 427 is provided about the gingival tie wings 416. More particularly, each gingival tie wing 416 outwardly extends from the gingival surface of the body 412 to define a flange 468 which engages the respective labial hooks 472a and 472b when the locking clip 426 is in the closed position. The engagement between the flanges 468 and the labial hook 472a, 472b maintains the locking clip 426 in the closed position thereby retaining the locking clip 426 against the archwire so as to inhibit relative movement between the archwire and the body 412 of the orthodontic bracket 410.

To close the orthodontic bracket 410, the locking clip 426 is pivoted about the tails 432 and 434 towards the locking mechanism 427 about the gingival tie wings 416. The lingual guides 474a and 474b contact the labial surfaces of the respective gingival tie wings 416 so that the curved free ends 482 of the lingual guides 474a and 474b are guided inward along the respective inner surfaces of the gingival tie wings 416. In doing so, the biasing members 470a, 470b are deflected towards one another so that they can be positioned into the interwing region 424 between the gingival tie wings 416 as the locking clip 426 is pivoted towards the closed position. The lingual guides 474a and 474b continue to be guided along the inner surfaces of the gingival tie wings 416 until the labial hooks 472a and 472b are positioned below the flanges 468 of the locking mechanisms 427a and 427b. This allows the biasing members 470a and 470b to snap back into their non-stressed state so that the labial hooks 472a and 472b engage the flanges 468 thereby maintaining the locking clip 426 in the closed position.

More particularly, the reaction force applied to the labial and inner surfaces of the gingival tie wings 416 by the lingual guides 474a and 474b cause the biasing members 470a and 470b to deflect (e.g., mesially or distally inward) thereby allowing the labial hooks 472a and 472b to pass into the reduced opening 448 of the interwing region 424 between the open and closed positions. When the lingual guides 474a and 474b are pivoted lingually beyond the flanges 468, the biasing members 470a and 470b snap back towards their non-stressed state and the lingual hooks 472a and 472b engage the flanges 468 of the retaining members 427a and 427b to its closed position. The biasing members 470a and 470b in this condition inhibit the locking clip 426 from moving back towards the open position. In this way, the archwire slot 420 remains closed thereby securing the archwire in the archwire slot.

To release the archwire, the biasing members 470a and 470b (e.g., the lingual guide portions 474a and 474b) are pushed generally towards one another (e.g., mesially-distally) to disengage each labial hook 472a and 472b from the respective flange 468. Thereafter, the biasing members 470a and 470b may be removed (e.g., labially) from flanges 468 of the retaining member 427 so that the locking clip 426 is free to pivot about the tails 432 and 434.

In this specific embodiment, the head 428 of the locking clip 426 extend gingivally beyond the first bridge portion 460. The labial surface of the gingival tie wings 416 may include a groove 480 having a shape complementary for receiving a portion of the locking clip 426 (e.g., head portion 428) while in the closed position. It is contemplated that the groove 480 may be configured with an angled or curved portion to aid in maintaining the locking clip 426 in the closed position. Desirably, the labial faces of the gingival tie wings 316 include the groove 480 having a generally semi-circular cross-section, which may be complementary to the locking clip 426.

Referring now to FIGS. 28J-28K, another embodiment of a self-ligating orthodontic bracket is shown and is generally indicated to by reference numeral 510. The bracket 510 may comprise a body 512, a base 514, and a locking mechanism including a locking clip 526 and a retaining member 527. The body 512 may include gingival tie wings 516 and occlusal tie wings 518 with a mesially-distally extending archwire slot 520 therebetween. A first bridge portion 560 and a second bridge portion 561 is provided in the interwing region 524, with the first bridge portion 560 spanning between the gingival tie wings 516 and the second bridge portion 561 spanning between the occlusal tie wings 518. It is appreciated that the first and second bridge portions 560 and 561 may extend from labial surface of the archwire slot up to the labial surfaces of the respective tie wings 516 and 518 thereby defining a portion of the gingival and occlusal walls of the archwire slot between the respective gingival and occlusal tie-wings.

In this embodiment, the locking clip 526 is in the form of spring element having a generally cruciform outline. The locking clip 526 may include a gingival head 528 having a lingually-gingivally projecting hook 572 and a curved lingual guides 574. The head 528 may be interconnected with a pair of oppositely directed arms 550 and 552 (e.g., mesially and distally extending arm portions) which extend across the archwire slot 520 to arm free ends 558. It is appreciated, that the arms 550 and 552 may at least partially or substantially extend in a parallel manner with the archwire slot 520. Each arm 550 and 552 may form a generally U-shaped configuration having a gingival portion extending to an occlusal portion with the arm free end 558 therebetween.

The locking clip 526 may also include opposed free ends (e.g., extending generally mesial and distal, though not required) that are out-turned to define oppositely directed spaced apart tail ends 532 and 534 respectively. Each of the tail ends 532 and 534 is received in a respective bore 536 and 538 formed in one of the occlusal tie wings 518 at an occlusal opening 596 in a lingual portion of the body 512.

The retaining member 527 includes a mesially-distally directed labial member 590 that extends between the gingival tie wings 516 in a generally parallel relationship to the first bridge portion 560 to define a first opening 564. The labial member 590 includes a lingual flange 568 that engages the hook 572 when the locking clip 426 is in the closed position. The engagement between the flange 568 and the hook 572 maintains the locking clip 526 in the closed position so that the locking clip 526 is retained against the archwire thereby inhibiting relative movement between the archwire and the body 512 of the orthodontic bracket 510.

To close the orthodontic bracket 510, the locking clip 526 is pivoted about the tails 532 and 534 towards the locking mechanism 527 (e.g., labial member 590) about the gingival tie wings 516. The lingual guide 574 contacts the labial-occlusal surfaces of the labial member 590 so that the hook 572 is guided occlusally along the occlusal inner surface of the labial member 590. In doing so, the head 528 is deflected occlusally towards the first bridge portion 560 so that the head 528 can be positioned into the first opening 564 between the gingival tie wings 516 as the locking clip 526 is pivoted towards the closed position. The lingual, guide 574 is continually guided along the occlusal inner surface of the labial member 590 until the free end 584 of the hook 572 is positioned below the flange 468 of the labial member 590. This allows the biasing member 570 to snap back towards its non-stressed state so that the hook 572 engage the flange 568 thereby maintaining the locking clip 526 in the closed position.

More particularly, the reaction force applied to the occlusal-inner surface of the labial member 590 by the lingual guide 574 causes the head 528 to deflect (e.g., occlusally) thereby allowing the hook 572 to pass into the first opening 564 between the open and closed positions. When the lingual guide 574 is pivoted (lingually-gingivally) beyond the flange 568, the locking clip 526 snaps back towards its non-stressed state so that the hook 572 to engage the flanges 468 thereby preventing removal of the hook 572 from the flange 568 and the first opening 564 during its closed position. The head 528 in this condition inhibits the locking clip 526 from moving back towards the open position. In this way, the archwire slot 520 remains closed thereby securing the archwire in the archwire slot.

To release the archwire, the head 528 (e.g., the hook 572) is pushed lingually and occlusally to disengage the hook 572 from the labial member 590. Thereafter, the biasing members 570 may be removed from labial member 590 and the first opening 564 so that the locking clip 526 is free to pivot about the tails 532 and 534.

Optionally, the locking clip 26 may further include a cover portion 90 as shown in FIG. 29A. The cover portion 90 defines a generally oval shape and may include a labial surface 92 that extends generally the length and width of the archwire slot when included. The cover portion 90 may also include an attachment member 94 for connecting to the locking clip 26. It is appreciated that the attachment member 94 is positioned about the lingual surface 96 of the cover portion 90 and has a size and shape complementary to the clip opening 60. When included, the attachment member 94 engages the clip opening 60 of the locking clip 26 so that it is removable affixed thereto. While in the closed position, it is appreciated that the cover portion 90 substantially or entirely cover the archwire slot having the archwire therein so as to provide a more aesthetic look to the bracket. Furthermore, it is appreciated that the cover portion 90 may aid in preventing food and/or plague buildup in the bracket 10. As shown in the drawing the cover portion 90 may be a separate component of the locking clip 26, however it is appreciated that the cover portion 90 and the locking clip 26 may be an integral piece.

Optionally, the locking clip 326 may further include a cover portion 390a as shown in FIG. 29B. The cover portion 390a may define a generally flat and/or curved portion having an oval and/or rectangular shape and may include a labial surface 392a that extends generally the length and width of the archwire slot when included. The cover portion 390a may also include a plurality of attachment members 394a (e.g., deformable attachment members) for connecting to the locking clip 326. It is appreciated that the attachment members 394a may be positioned about the lingual surface 396a of the cover portion 390a at the respective corners thereof and may have a size and shape complementary to the thickness of the locking clip 326. When included, the attachment members 394a engage multiple portions of the locking clip 326 so that the cover portion 390a is removable affixed thereto. While in the closed position, it is appreciated that the cover portion 390a may substantially or entirely cover the archwire slot having the archwire therein so as to provide a more aesthetic look to the bracket. Furthermore, it is appreciated that the cover portion 390a may aid in preventing food and/or plague buildup in the bracket 310. As shown in the drawings, the cover portion 390a may be a separate component of the locking clip 326; however it is appreciated that the cover portion 390a and the locking clip 326 may be an integral piece.

Optionally, the locking clip 326b may further include a cover portion 390b as shown in FIG. 29C. The cover portion 390b may define a generally oval and/or rectangular shape and may include a labial surface 392b that extends generally the length and width of the archwire slot when included. The cover portion 390b may also include a first attachment member 394b and a second attachment member 395b (e.g., deformable attachment members) for connecting to the locking clip 326b. It is appreciated that the attachment member 394b may be positioned about the gingival free end 398b of the cover portion 390b and may include a tubular shape having a mesial-distal opening 399b along its entire length for receive the locking clip 326b. The attachment member 394b has a size and shape complementary to the thickness of the locking clip 326b. In this embodiment, the biasing member 370 (having a guide portion 374b and a hook portion 372b for engaging the retaining member) has been removed from the clip 326 so that the cover portion 390b further includes a biasing member 370b for engaging the flange 368 in the closed position. When included, the attachment members 394b (being deformable) snaps over the gingival portion of the locking clip 326b (the attachment member being generally tubular with a longitudinal opening for receiving a portion of the locking clip) so that the cover portion 390b is removable affixed thereto. While in the closed position, it is appreciated that the cover portion 390b may substantially or entirely cover the archwire slot having the archwire therein so as to provide a more aesthetic look to the bracket. Furthermore, it is appreciated that the cover portion 390b may aid in preventing food and/or plague buildup in the bracket 310. As shown in the drawings, the cover portion 390b may be a separate component of the locking clip 326b; however it is appreciated that the cover portion 390b and the locking clip 326b may be an integral piece.

FIGS. 30A-30D are various views of another alternate embodiment of the self-ligating bracket shown in FIG. 28E in which the bracket 210a may comprise a body 212a, a base 214a, and a locking mechanism including the locking clip 226a and a retaining member 227a. The body 212a may include gingival tie wings 216a and occlusal tie wings 218a with a mesially-distally extending archwire slot 220a therebetween. In this specific example, the body 212a has a rectangular-shaped body and includes a first bridge portion 260a in the interwing region 224a, which spans between the gingival tie wings 216a. The first bridge portion 260a extends from labial surface of the archwire slot 220a to the labial surface the gingival tie wings. The body 212a may also include a second bridge portion 261a in the interwing region 224a, which spans between the occlusal tie wings 218a. It is appreciated that the second bridge portion 261a extends partially from the labial surface of the archwire slot 220a to allow for rotation of the locking clip 226a.

The locking clip 226a may be in the form of a generally cross-shaped spring element having out-turned free mesial and distal ends defining laterally spaced tails 232a and 234a. Each of the tails is pivotally received within a respective bore 236a and 238a formed in the respective one of the occlusal tie wings 218a.

The retaining member 227a is provided in the first bridge portion 260a and may include sets of opposing stops 244a and 246a. More particularly, to close the orthodontic bracket 210a, the locking clip 226a may be pivoted about the tails 232a and 234a. As the locking clip 226a is pivoted, the clip arms 250a and 252a of the head portion 228a are pushed into the bridge portion 260a against the respective pairs of opposing stops 244a and 246a. The reaction force applied to the sets of opposing stops 244a and 246a by the clip arms 250a and 252a causes the clips arms 250a and 252a and/or the opposing stops 244a and 246a to deform thereby allowing the clip arms 250a and 252a to pass through reduced openings 248 between the open and closed positions. When the clip head 228a is pivoted beyond the sets of opposing stops 244a and 246a, the clip arms 250a and 252a, the opposing stops 244a and 246a, or a combination of both snap back into their non-stressed state and the head 226a is biased towards the labial surface 219a about the recesses 262a to its closed position below the respective sets of opposing stops 244a and 246a. The sets of opposing stops 244a and 246a in this condition (e.g., non-stressed state) inhibit the locking clip 226a from moving back towards the open position. In this way, the archwire slot 220a remains closed thereby securing the archwire (not shown) in the archwire slot 220a. Furthermore, the archwire slot may include a generally non-flat mesially-distally extending portion (e.g., a curved portion such as a concave portion or a convex portion and/or an angled portion). For example, a labially positioned bracket may include an archwire slot having a lingually directed base surface thereby forming a generally convexed portion of the archwire slot or a lingually positioned bracket may include an archwire slot having a labially directed base surface thereby forming a generally concaved portion of the archwire slot, though not required. More particularly, the archwire slot may include a lingually directed portion that also extends along the mesially-distally direction to define at least one non-flat portion of the archwire slot. Desirably, a curved and/or angled archwire 720a with a curved and/or angled labial surface 721a may provide for a more aesthetic looking bracket having a low profile.

Referring now to FIGS. 30E-30L, additional embodiments of a self-ligating orthodontic bracket are shown and are generally indicated to by reference numeral 710 (710a, 710b, 710c, and 710d). The orthodontic brackets 710a and 710b being generally similar to the embodiment of FIGS. 28A-28B, while the orthodontic brackets 710c and 710d being generally similar to the embodiment of FIGS. 28H-28I. However, these embodiments are not limiting and it is appreciated that any of the brackets described herein or otherwise may include an archwire slot having a generally non-flat mesially-distally extending portion (e.g., a curved portion such as a concave portion or a convex portion and/or an angled portion). For example, a labially positioned bracket may include an archwire slot having a lingually directed base surface thereby forming a generally convexed portion of the archwire slot or a lingually positioned bracket may include an archwire slot having a labially directed base surface thereby forming a generally concaved portion of the archwire slot, though not required.

More particularly, the archwire slot may include a lingually directed portion that also extends along the mesially-distally direction to define at least one non-flat portion of the archwire slot. Desirably, a curved and/or angled archwire 720 with a curved and/or angled labial surface 721 may provide for a more aesthetic looking bracket having a low profile with vertical slot 725 (FIGS. 30E-30F and 30I-30J or a very low profile without the vertical slot 725 (FIGS. 30G-30H and 30K-30L). It is appreciated that the archwire slot may extend mesially-distally in a generally parallel manner relative to the lingual surface of the base, the labial surface of the base, the labial surface of the tooth, or otherwise, though not required.

A portion of the archwire slot may be lingually directed towards the base 714 relative to at least one labially directed portion of the archwire slot. More particularly, the at least one labially directed portion may include an apex portion 796 that is labially offset or displaced relative to at least one other mesially-distally located portion of the archwire slot (e.g., mesial and distal ends 794 of the arch wire slot 720). It is appreciated that the archwire slot may include a constant curve radius or taper along its mesial-distal length; however, a variable curve radius or variable taper is also contemplated. Desirably, the apex portion 796 may be provided in a central portion of the arch wire slot (e.g., interwing region 724). Preferably, the apex portion 796 is provided midway of the archwire slot, such that the arch wire slot is symmetrical as shown in the cross-sections of FIGS. 30F, 30H, 30J, and 30L. However, it is appreciated that the apex portion 796 may be provided at various locations along the archwire slot from the mesial end to the distal end or may be provided at one of the mesial and distal ends 794. Furthermore, it is also appreciated that the archwire slot may include a generally flat portion in the interwing region while having lingually directed end portions that may be angled and/or curved relative to the central (e.g., midway) flat portion.

As mentioned above, the base surface of the archwire slot may also include a concaved portion. When included, a portion of the archwire slot base surface may be labially directed away from the base of the bracket relative to another portion of the archwire slot base surface. This may be accomplished along a curvature or in an angled manner. Furthermore, as discussed above, any curved and/or angled portion of the archwire slot base surface may be positioned along one or more portions along the base of the archwire slot (e.g., at an edge portion, at the opposing edge portion, at a central portion, or in between or elsewhere along the base surface of the arch wire slot.

FIGS. 31A-31D are various views of an alternate embodiment of the self-ligating dental bracket shown in FIGS. 9A-9G in which the lingual free end 1028s pivotally engages a lingual opening 1064s formed in the lingual portion of the open stop groove 1042s. In this specific embodiment, the locking clip 1026s may include a generally J-shaped configuration and include deformable fingers 1062s having flange portions 1066. Once received in the lingual cavity, the deformable fingers may remain in a partially stressed state due to active engagement of the outer edges 1070s of the flange portions with the respective interior mesial and distal side walls 1136s of the occlusal tie wings 1018s to aid in suppressing movement (e.g., twisting, mesial-distal movement, and/or otherwise) of the locking clip 1026s while in the closed position. Additionally, this active engagement further allows for rotation of the locking and/or securement of the locking clip to the bracket body.

It is appreciated that the locking clips described herein may be formed of a superelastic member such as a nickel-titanium alloy, even if the locking member has been deformed relatively greatly, there is no large variation of the load, and the arch wire can be pressed down moderately under the superelasticity. Additionally, favorable operating efficiency in the treatment operation can be maintained. For example, wires ranging from a narrow round wire to a full-sized square wire can be pressed into the slot with a virtually equivalent load, and three-dimensional control becomes possible starting from an early period of treatment with an optimum force in the living body. In addition to the restoring force of the wire, the correcting force is also produced by the force with which the locking member presses down the arch wire, and treatment of higher dimensionality becomes possible.

In one specific example, the locking clip may be formed of an alloy comprising 35-55 (e.g., 40-50) wt % Co, 10-30 (e.g., 15-25) wt % Ni, 10-30 (e.g., 15-25) wt % Cr, 0.5-15 (e.g., 1-10) wt % Fe, 0.01-15 (e.g., 0.1-10) wt % W, 0.01-15 (e.g., 0.1-10) wt % Mo, and/or 0.01-10 (e.g., 0.1-5) wt % Ti.

It is appreciated that the present invention may include one or more of the following features: the base may include an 80 gauge micro-mesh pad for optimal bonding/de-bonding; the body may be in the form of a rhomboid, square, or oval-shaped body design; the locking clip may be metal, plastic or a composite; the locking clip may be in the form of a wire configuration; the locking clip may be formed by utilizing wire-bending or similar manufacturing processes; the locking clip may exhibit optimum balance between force applied to secure the arch wire in the slot to motivate tooth movement and maintaining flexibility of the wire properties in the locking clip to apply rotational control of the arch wire; the edges of the locking clip may maintain enough elasticity to be assembled or disassembled by the user by either an inner or outer hinge design; the locking clip may be inserted or removed by simply squeezing the lower bars (e.g., with tweezers) to allow compression and expansion of the locking clip; the locking clip may open and/or close by rotation on the hinged-axis; the locking clip may be locked into position by any of the following methods 1) push-lock design that locks the locking clip into place by utilizing the elasticity of locking clip around side bevels in the body of bracket, 2) push-lock design that locks the locking clip into place by utilizing the elasticity of locking clip around a top bevel in the body of bracket that exhibits a downward force on the locking clip, 3) push-lock design that locks the locking clip into place by utilizing the cavity in the body of the bracket that holds the locking clip into place, 4) snap-fit design with a centrally located locking mechanism that compresses when pushed into the slot of the body before expanding into locked position in the open cavity of the body and 5) snap-fit design with two laterally located locking mechanisms that compresses when pushed into the bevels before expanding into locked position when the mechanism clears the bevel; optimum rotational control of the arch wire as the locking clip can be extended as far mesially or distally as necessary without affecting the mechanism of the locking clip/body assembly; the locking clip spans over the entire width (e.g., of the archwire slot) of the bracket base while engaging the wire, thus providing maximum torque possible; low friction in system as there will be two points of contact between the locking clip and arch wire (gingival and occlusal corners at mesial and distal ends of the archwire) as opposed to continuous line of contact along only gingival portions or occlusal portions of the archwire; the archwire slot may be designed with at least one bump (e.g., a plurality of bumps) and/or at least one groove (e.g., a plurality of grooves) in the bottom and/or side walls to minimize the contact area between the archwire and archwire slot, (to optionally express the built-in torque at any wire size); the locking clip may be designed with at least one bump (e.g., a plurality of bumps) and/or at least one groove (e.g., a plurality of grooves) to reduce the contact area between the archwire and archwire slot, (to optionally express the built-in torque at any wire size); the locking clip may be interchangeable with any type of body regardless of material (metal, ceramic, plastic, etc.) to keep the in-out dimensions of the system consistent; the open/close mechanism in this application may be a freely rotating hinge; upon removal of the locking clip, the self-ligating bracket may be utilized as a conventional (twin) bracket; the tie wings may be used for ligation; the tie wings may be flared out to provide maximum torque; direct translation of forces occur from the locking clip to the archwire, to a force point on the bracket and to a Facial Axis (FA) point on tooth; the locking clip may engage the archwire at both the gingival and occlusal corners and translate directly to the FA point on the tooth to optimize treatment time of the patient; the locking clip may be over-molded or insert-molded with plastic for aesthetic purposes; the material used for forming the locking clip and/or bracket may be plastic, which may be of any color as indicated by the patient; low friction characteristics of system may still be maintained since there may be no or substantially no contact between the molded plastic and arch wire; the base and the body may be coated with aesthetic material, antibiofilm material or both (for example, silver nanoparticles, PEG); the body of bracket may be interchangeable with either a rhomboid, square, or oval shaped body; the base may be contoured to marginal ridge for increased accuracy in placement and aesthetics (applicable to molar and bicuspids); the body may be over-molded with a soft plastic material (desirably in central and lateral brackets) to reduce chipping of upper incisal edge; a cap and/or cover portion formed of a soft plastic material may be attached to the bracket to reduce/eliminate chipping of upper incisal edge, the cap and/or cover portion may be removed after first phase of treatment; and any combination thereof.

It will be further appreciated that functions or structures of a plurality of components or steps may be combined into a single component or step, or the functions or structures of one-step or component may be split among plural steps or components. The present invention contemplates all of these combinations. Dimensions and geometries of the various structures depicted herein are not intended to be restrictive of the invention, and other dimensions or geometries are possible. References to directions are intended to clarify the description and do not in any way limit the scope of the invention. In other embodiments, the reference directions may be other than are shown, disclosed, or arranged differently. Also, it is to be understood that the phraseology and terminology used herein is for the purpose of description and should not be regarded as limiting. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention. The present invention also encompasses intermediate and end products resulting from the practice of the methods herein. The use of "comprising" or "including" also contemplates embodiments that "consist essentially of" or "consist of" the recited feature.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

The invention claimed is:

1. A self-ligating orthodontic bracket comprising:
a mounting pad adapted to engage the tooth surface;
a bracket body having a base portion secured to the mounting pad; the bracket body having an arch wire slot which extends in a mesiodistal direction formed therein;
at least one pair of occlusal and gingival tie wings; and
a generally U shaped, locking clip wherein the clip allows placement and removal of the arch wire when in the open position and prevents the displacement of the arch wire from the bracket member when in the closed position, the locking clip having a labial free end portion for engagement with the at least one pair of occlusal and gingival tie wings and a lingual base side portion having flange portions extending therefrom;
wherein the mounting pad and the base portion of the body define a lingual cavity for securement of the lingual base side portion of the clip to the bracket, the lingual cavity having a lingual opening for allowing the slideable movement of the locking clip between the open and closed positions; and
wherein the lingual opening includes a smaller width in the mesiodistal direction than the lingual cavity and the flange portions extend mesiodistally from the lingual base side portion within the lingual cavity such the flange portions have a larger width in the mesiodistial direction than the lingual opening to prevent the flange portions of the lingual base side portion from passing through the lingual opening thereby maintaining the flange portions of the lingual base side portion within the lingual cavity while securing the locking clip to the bracket.

2. The orthodontic bracket according to claim 1, wherein the facial surface of the clip includes an aperture to allow a standard dental instrument to mate for opening the clip in the occlusal direction.

3. The orthodontic bracket according to claim 2, wherein in the body includes an entry groove to guide the standard dental instruments on a plane parallel to the aperture on the clip.

4. The orthodontic bracket according to claim 1, further comprising at least one receiving area formed about at least one of a mesially side and a distally side of the bracket body, the at least one receiving area being defined by a receiving member.

5. The orthodontic bracket according to claim 4, wherein the receiving member is selected from the group consisting of:
 a. a labial hood;
 b. a lingual ledge;
 c. an end wall extending between a labial hood and a lingual ledge, and opposingly spaced from the body thereby enclosing at least a portion of the receiving area; and
 d. a c-shaped member
 e.

6. The orthodontic bracket according to claim 4, wherein mesial and distal portions of a labial free end of the clip prongs extend beyond the body and arch-wire slot and a ledge has been added as a separate artifact as mesial, the retaining member is selected from the group consisting of:
 a) distal extensions from the body to provide a positive seat for the labial free end of the clip in the closed position;
 b) extended mesial-distal ledges from the body have a cover that protects the mesial and distal edges of the labial free end of the clip in the closed position;
 c) extended mesial-distal ledges from the body have enclosed pockets that protects the mesial, distal, and gingival edges of the labial free end of the clip in the closed position; and
 d) extended mesial-distal ledges from the body have open pockets in the form of a "C-cup" that protects the gingival edges of the labial free end of the clip in the closed position.

7. The orthodontic bracket according to claim 4, wherein the receiving member includes a continuous channel extends in the gingival-occlusal direction through the lingual cavity and the lingual opening of the body to facilitate the cleaning of entrapped calculus and/or tartar.

8. The orthodontic bracket according to claim 7, wherein the depth of the continuous channel that travels mesial-distally in the clip resting closed position has been reduced to a thickness less than the thickness of the archwire such that the smallest possible arch wire does not get entrapped during treatment.

9. The orthodontic bracket according to claim 1, wherein the archwire slot defines a lingually directed, mesially-distally extending curved portion or profile.

10. The orthodontic bracket according to claim 1, wherein the archwire slot defines a lingually directed, mesially-distally extending angled portion or profile.

11. The orthodontic bracket according to claim 1, wherein the flange portions extend mesiodistally from the lingual base side portion for a generally T-shaped free end of the lingual base side portion in the mesiodistal direction.

12. The orthodontic bracket according to claim 1, wherein the lingual cavity is free of a throughhole extending in gingival-occlusal direction from the lingual opening.

* * * * *